(12) United States Patent
Karoyan

(10) Patent No.: US 11,306,124 B2
(45) Date of Patent: Apr. 19, 2022

(54) AGONIST AGENTS OF CD47 INDUCING PROGRAMMED CELL DEATH AND THEIR USE IN THE TREATMENTS OF DISEASES ASSOCIATED WITH DEFECTS IN PROGRAMMED CELL DEATH

(71) Applicants: SORBONNE UNIVERSITE, Paris (FR); Centre National de la Recherche Scientifique, Paris (FR)

(72) Inventor: Philippe Karoyan, Paris (FR)

(73) Assignees: Sorbonne Universite, Paris (FR); Centre National De La Recherche Scientifique, Paris (FR)

( * ) Notice: Subject to any disclaimer, the term of this patent is extended or adjusted under 35 U.S.C. 154(b) by 0 days.

(21) Appl. No.: 16/099,997

(22) PCT Filed: May 10, 2017

(86) PCT No.: PCT/EP2017/061233
§ 371 (c)(1),
(2) Date: Nov. 8, 2018

(87) PCT Pub. No.: WO2017/194634
PCT Pub. Date: Nov. 16, 2017

(65) Prior Publication Data
US 2019/0135865 A1    May 9, 2019

(30) Foreign Application Priority Data
May 10, 2016 (EP) .................... 16305543

(51) Int. Cl.
| | |
|---|---|
| *C07K 7/50* | (2006.01) |
| *C07K 7/64* | (2006.01) |
| *A61P 37/06* | (2006.01) |
| *A61P 29/00* | (2006.01) |
| *A61K 38/00* | (2006.01) |
| *C07K 14/47* | (2006.01) |
| *C07K 14/705* | (2006.01) |

(52) U.S. Cl.
CPC ............... *C07K 7/50* (2013.01); *A61P 29/00* (2018.01); *A61P 37/06* (2018.01); *C07K 7/64* (2013.01); *C07K 14/4705* (2013.01); *C07K 14/70596* (2013.01); *A61K 38/00* (2013.01)

(58) Field of Classification Search
None
See application file for complete search history.

(56) References Cited

FOREIGN PATENT DOCUMENTS

WO    2013/182650 A1    12/2013

OTHER PUBLICATIONS

International Search Report dated Aug. 22, 2017, issued in corresponding International Application No. PCT/EP2017/061233, filed May 10, 2017, 3 pages.
Written Opinion dated Aug. 22, 2017, issued in corresponding International Application No. PCT/EP2017/061233, filed May 10, 2017, 6 pages.
Chan, L.Y., et al., "Cyclic Thrombospondin-1 Mimetics: Grafting of a Thrombospondin Sequence Into Circular Disulfide-Rich Frameworks to Inhibit Endothelial Cell Migration," Bioscience Reports 35, 2015, pp. 1-12.
Martinez-Torres, A.-C., et al., "CD47 Agonist Peptides Induce Programmed Cell Death in Refractory Chronic Lymphocytic Leukemia B Cells Via PLCγ1 Activation: Evidence From Mice and Humans," PLoS Medicine 12(3): e1001796, 2015, 37 pages.
Wang, S., et al., "Development of a Prosaposin-Derived Therapeutic Cyclic Peptide That Targets Ovarian Cancer Via the Tumor Microenvironment," Science Translational Medicine 8(329), Mar. 2016, 12 pages.

*Primary Examiner* — Thomas S Heard
(74) *Attorney, Agent, or Firm* — Christensen O'Connor Johnson Kindless PLLC

(57) ABSTRACT

The present invention relates to cyclic peptides mimetics of the C-terminal binding domain of TSP-1. The present invention also relates to the use of these cyclic peptides as agonists of CD47 and their ability to trigger programmed cell death (PCD). The present invention further relate to a pharmaceutical composition for use in the treatment of diseases associated with defects in PCD such as cancers and immunological disorders (including chronic inflammation) and comprising at least one cyclic peptide according to the invention.

9 Claims, 20 Drawing Sheets
Specification includes a Sequence Listing.

PKT16 VS MB 1600nM

PKTD1

PKTD10

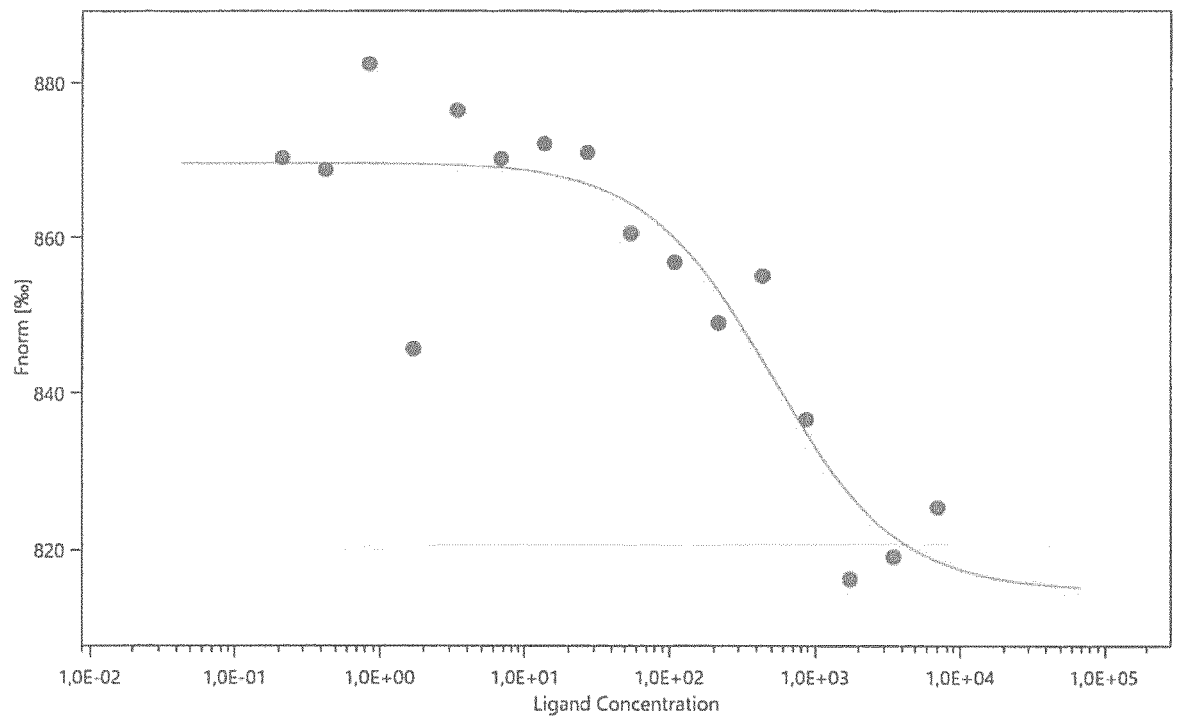
Figure 6C - PKTD10-1
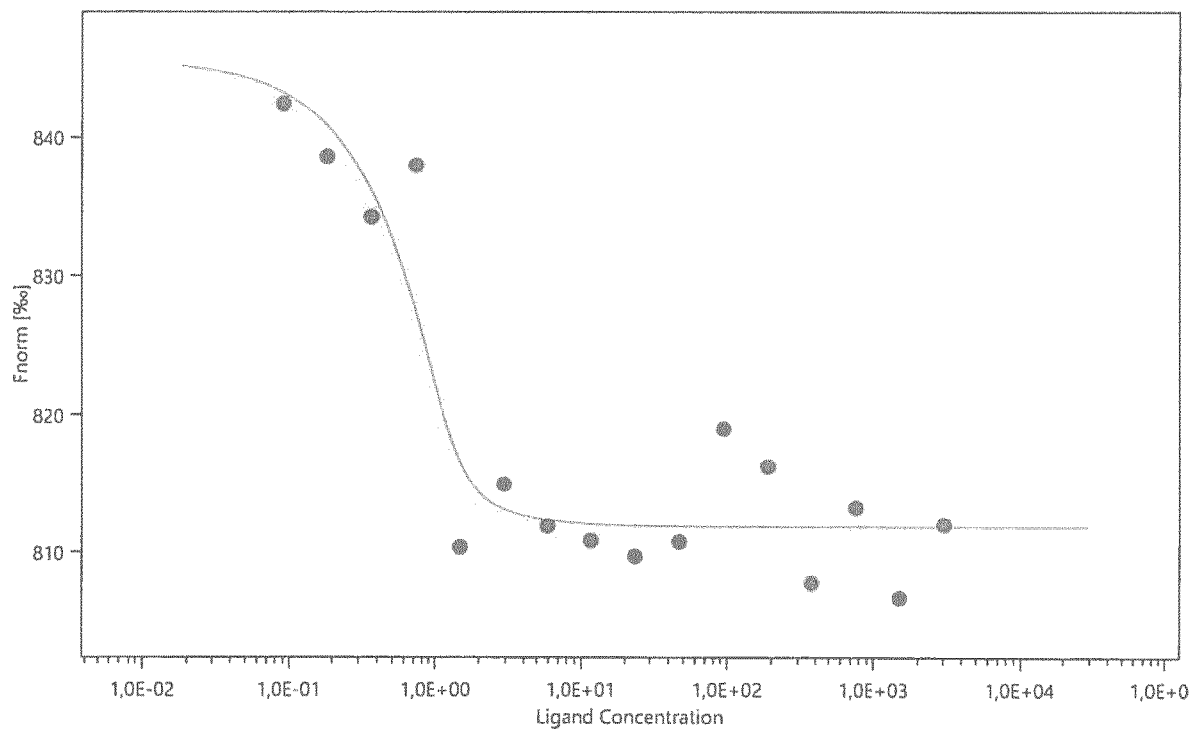
Figure 6D - PKTD10-3

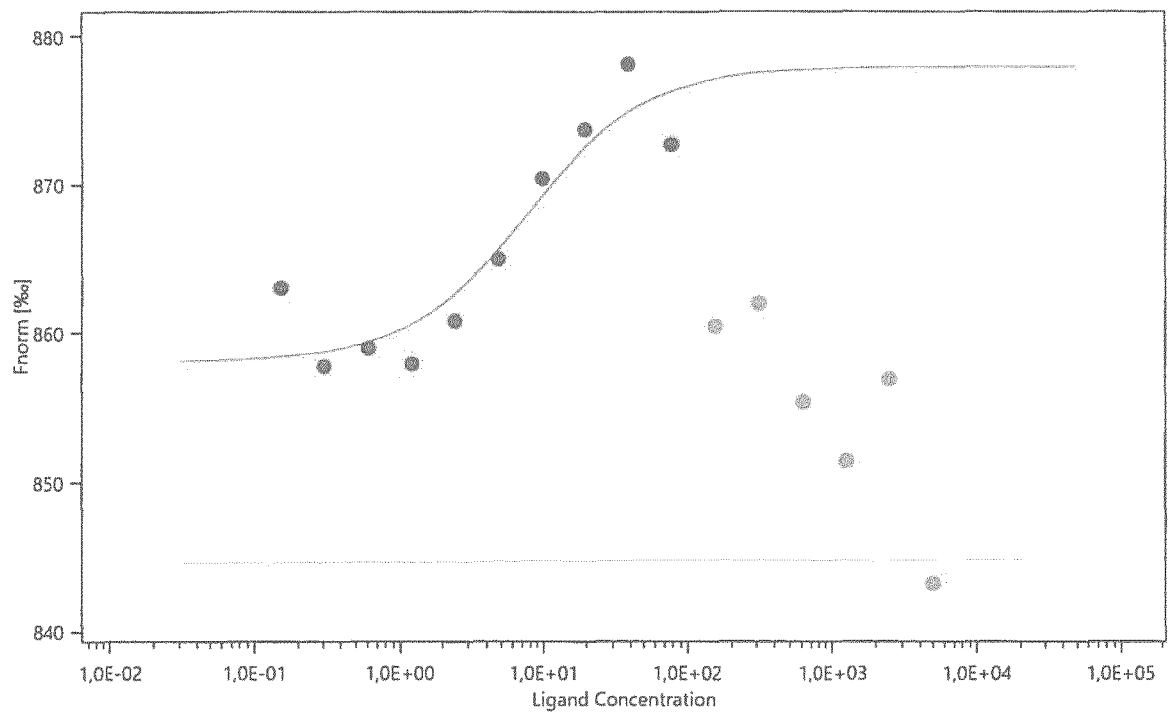
Figure 6E - PKTD10-4
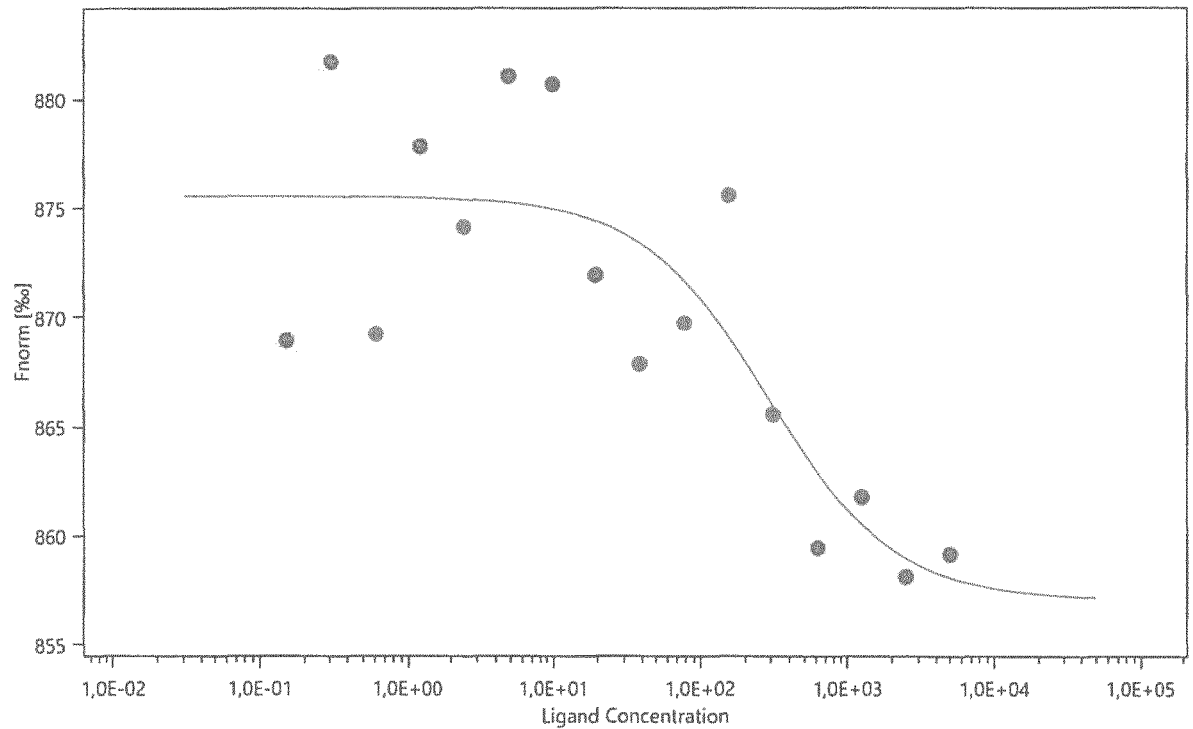
Figure 6F - PKTD10-5

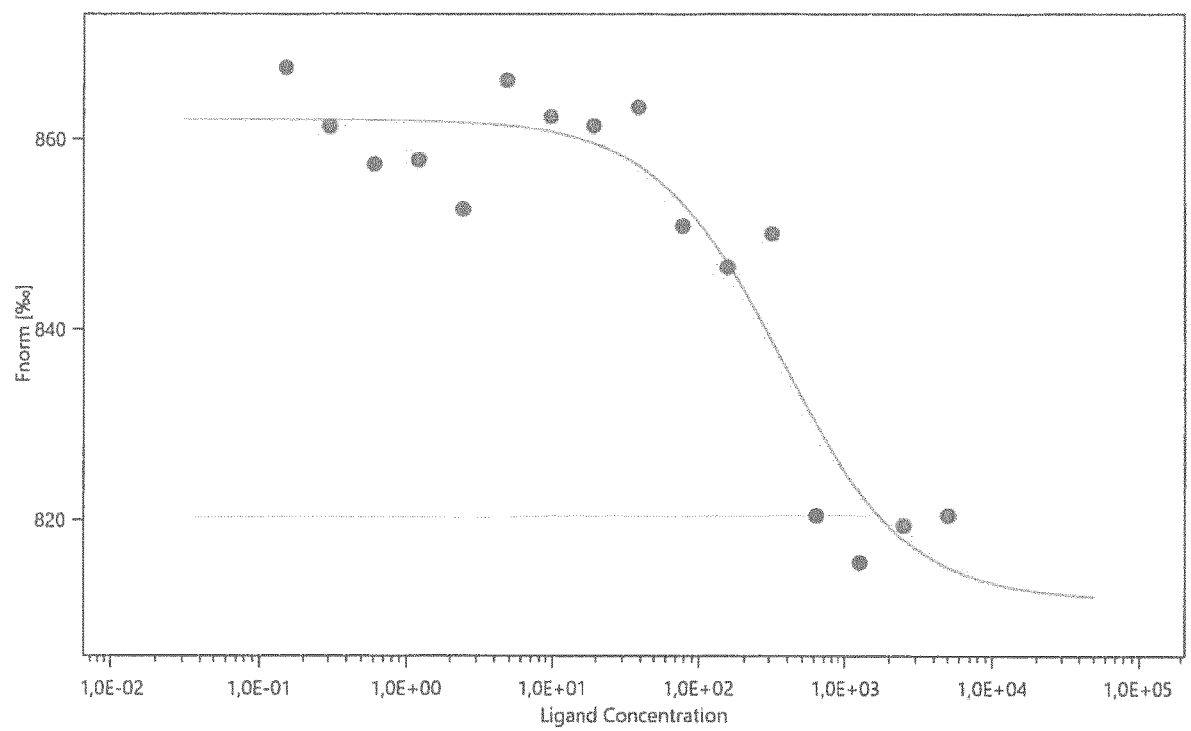
Figure 6G - PKTD10-7
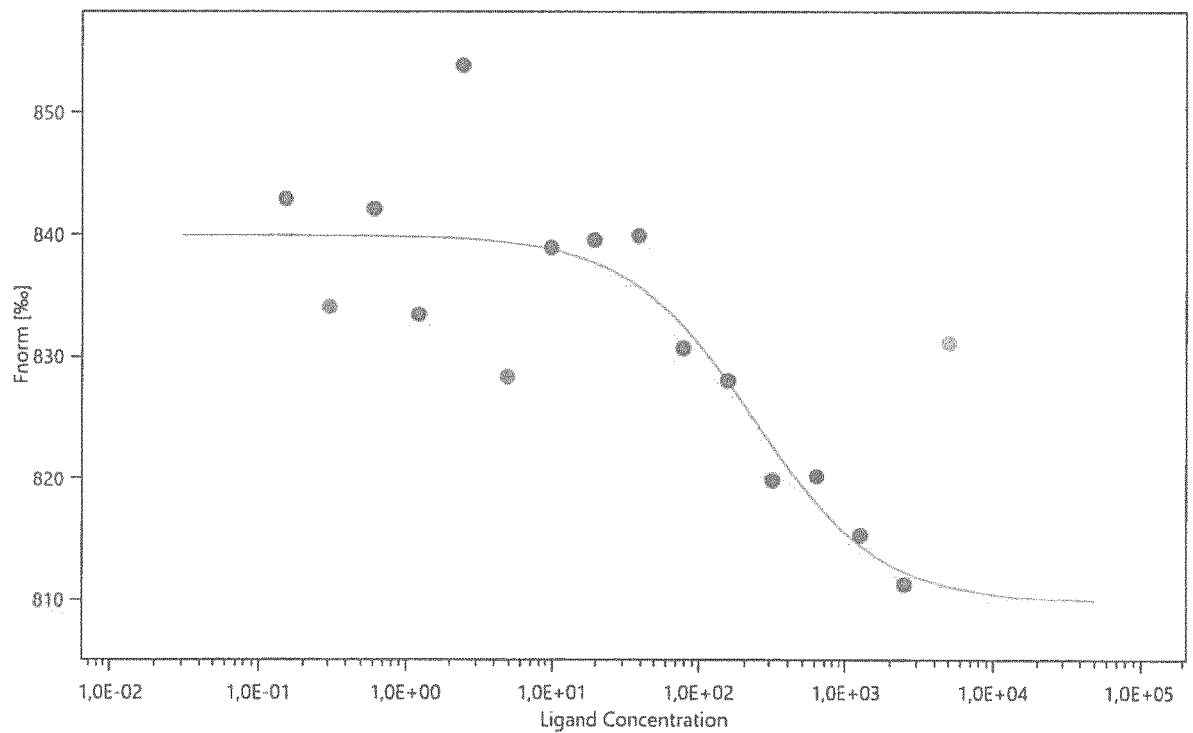
Figure 6H - PKTD10-8

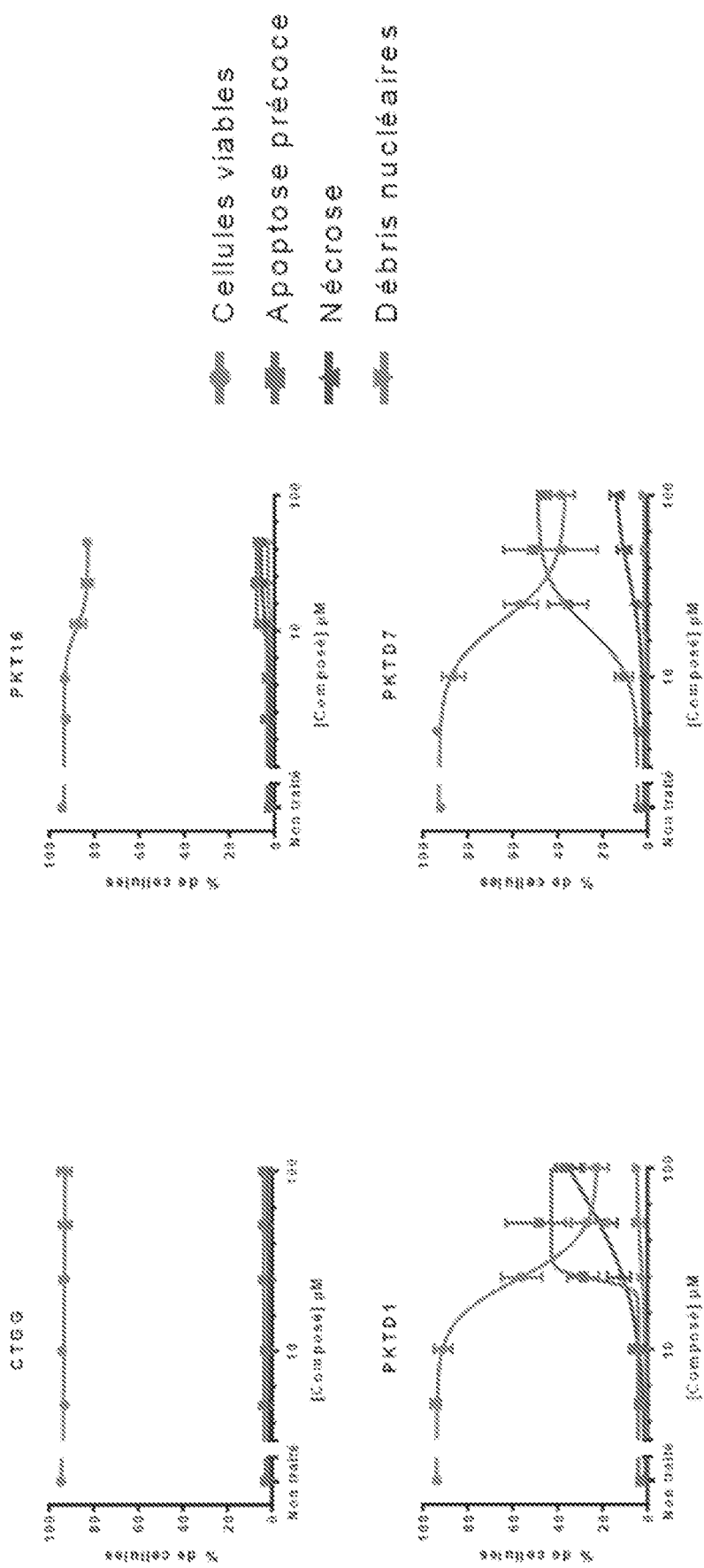
Assays on HTC-116
Figure 7A(1)

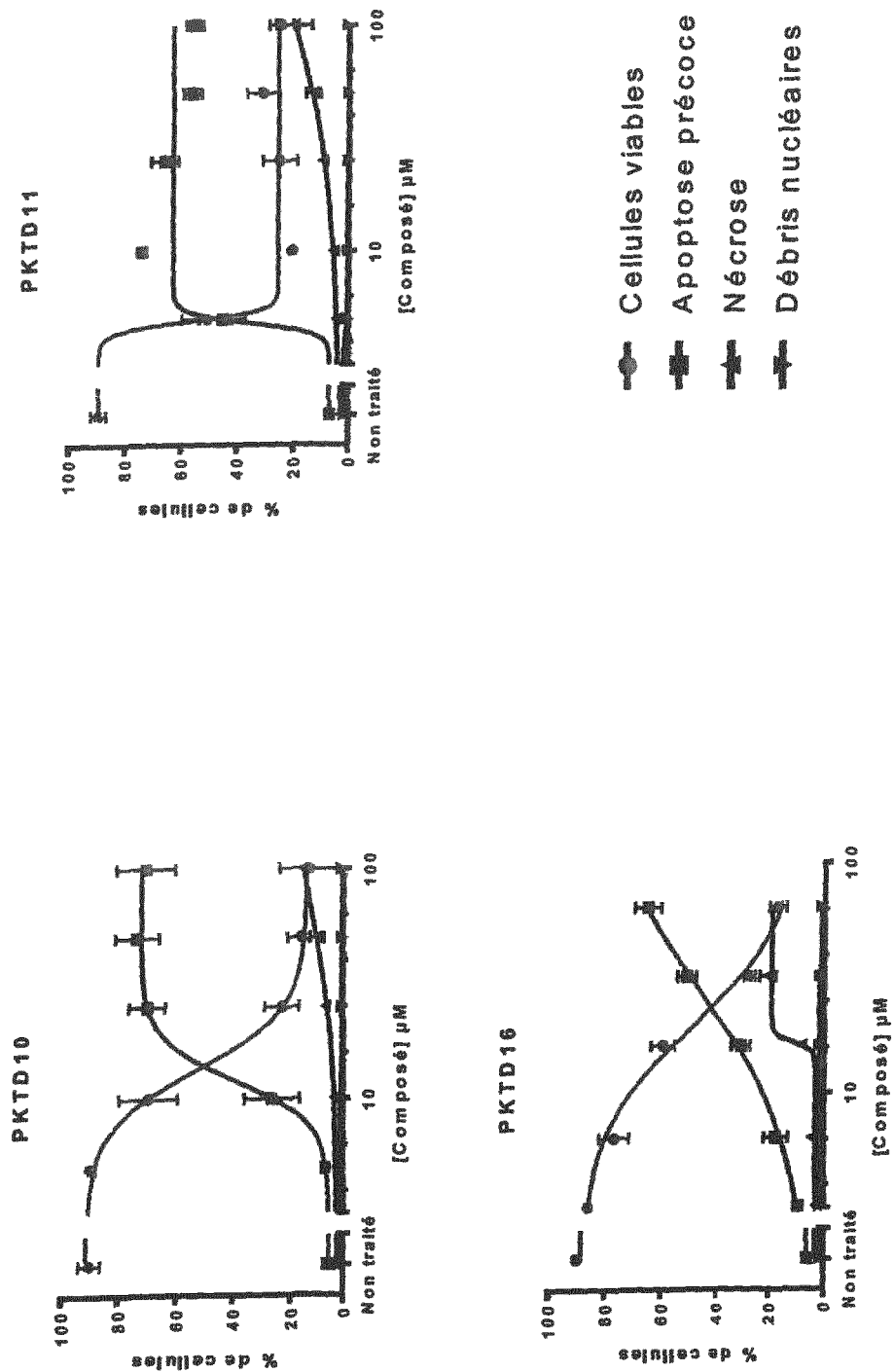
Assays on HTC-116
Figure 7A(2)

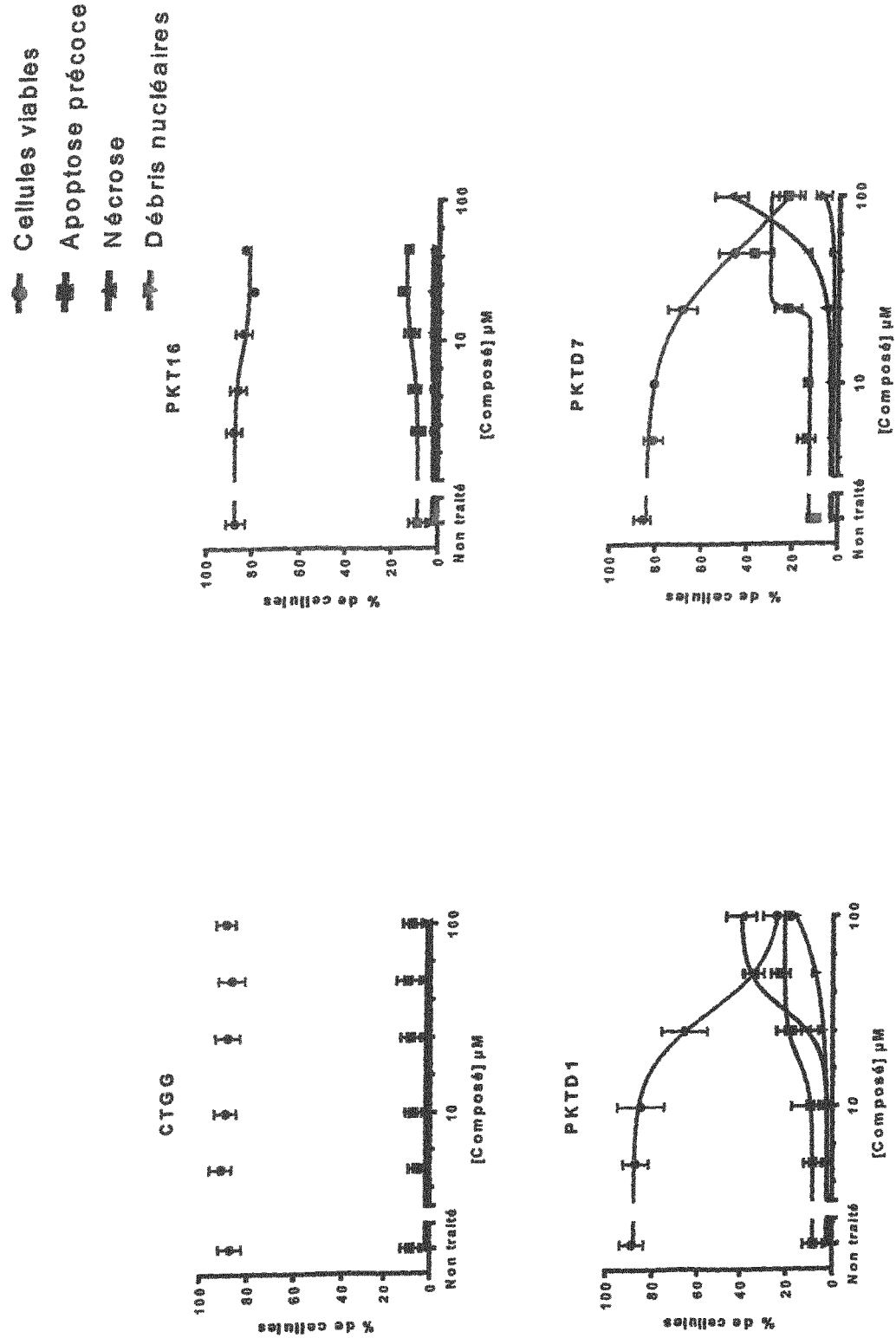
Assays on A549
Figure 7B(1)

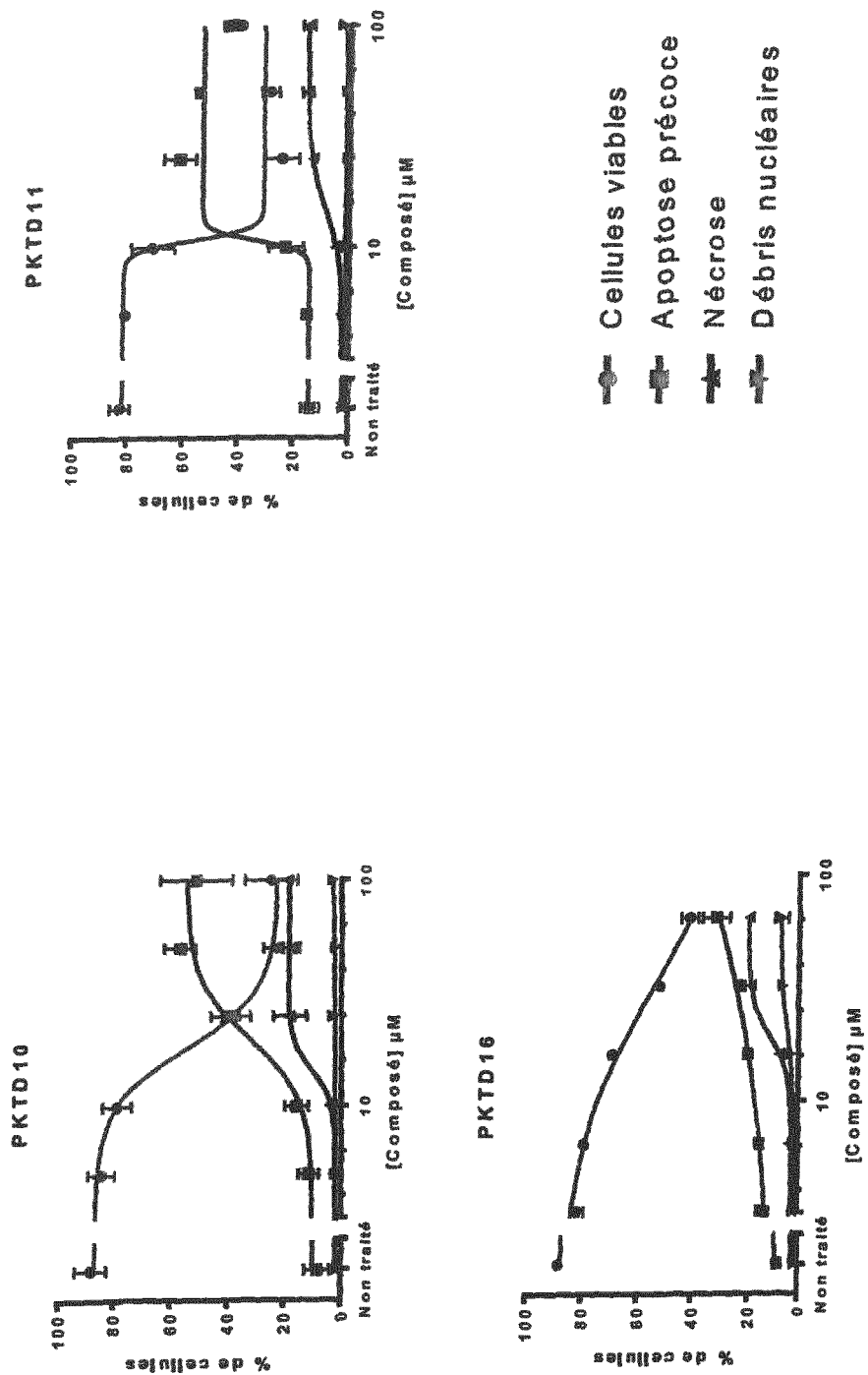
Assays on A549
Figure 7B(2)

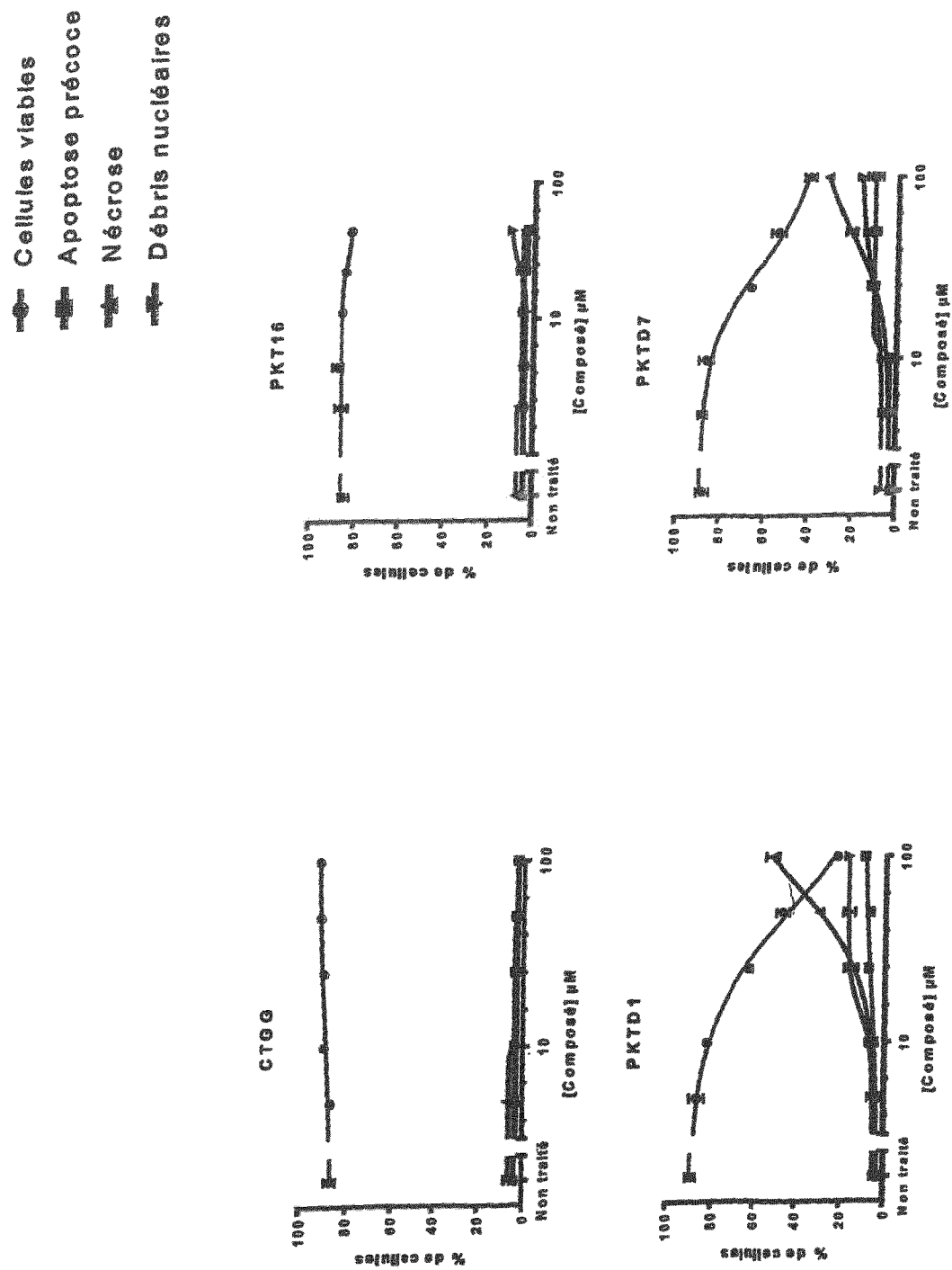
Assays on BxPC3
Figure 7C(1)

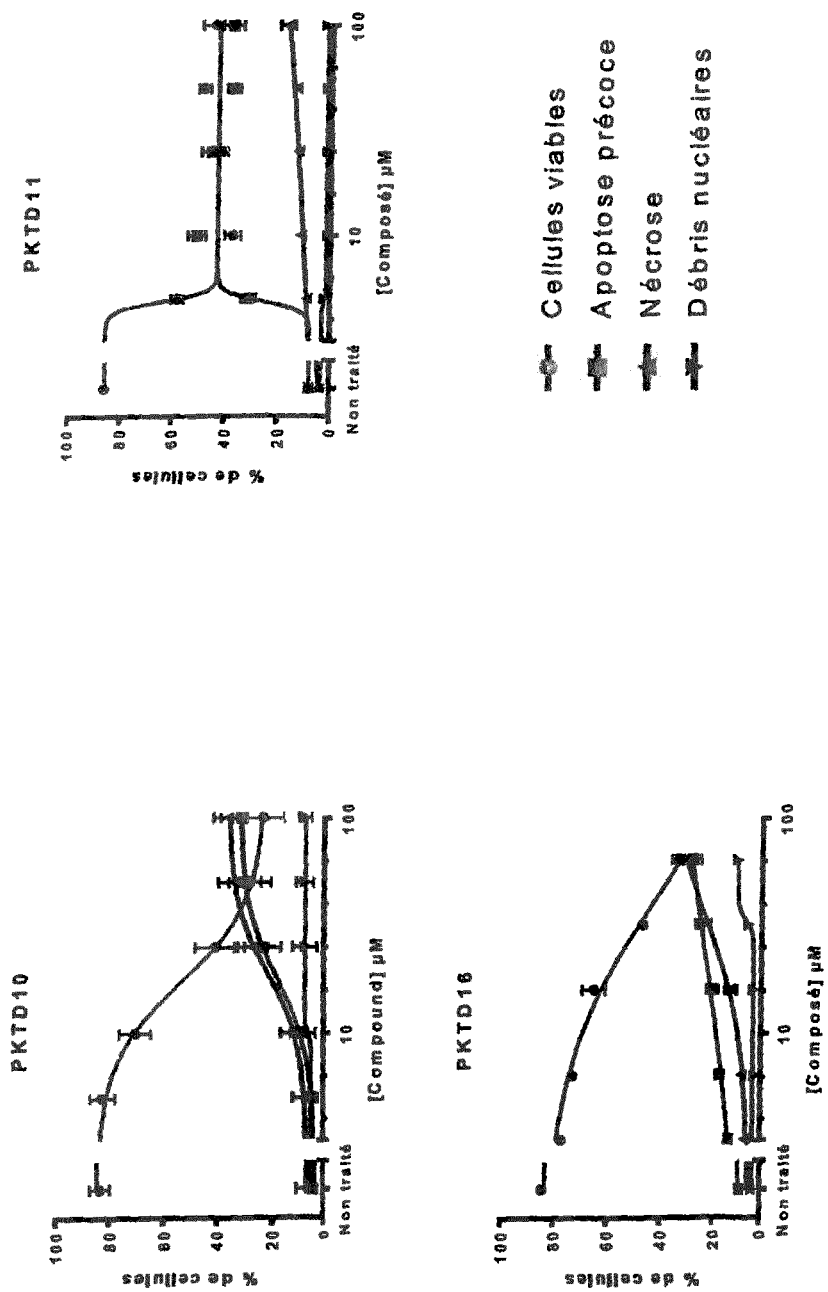
Assays on BxPC3
Figure 7C(2)

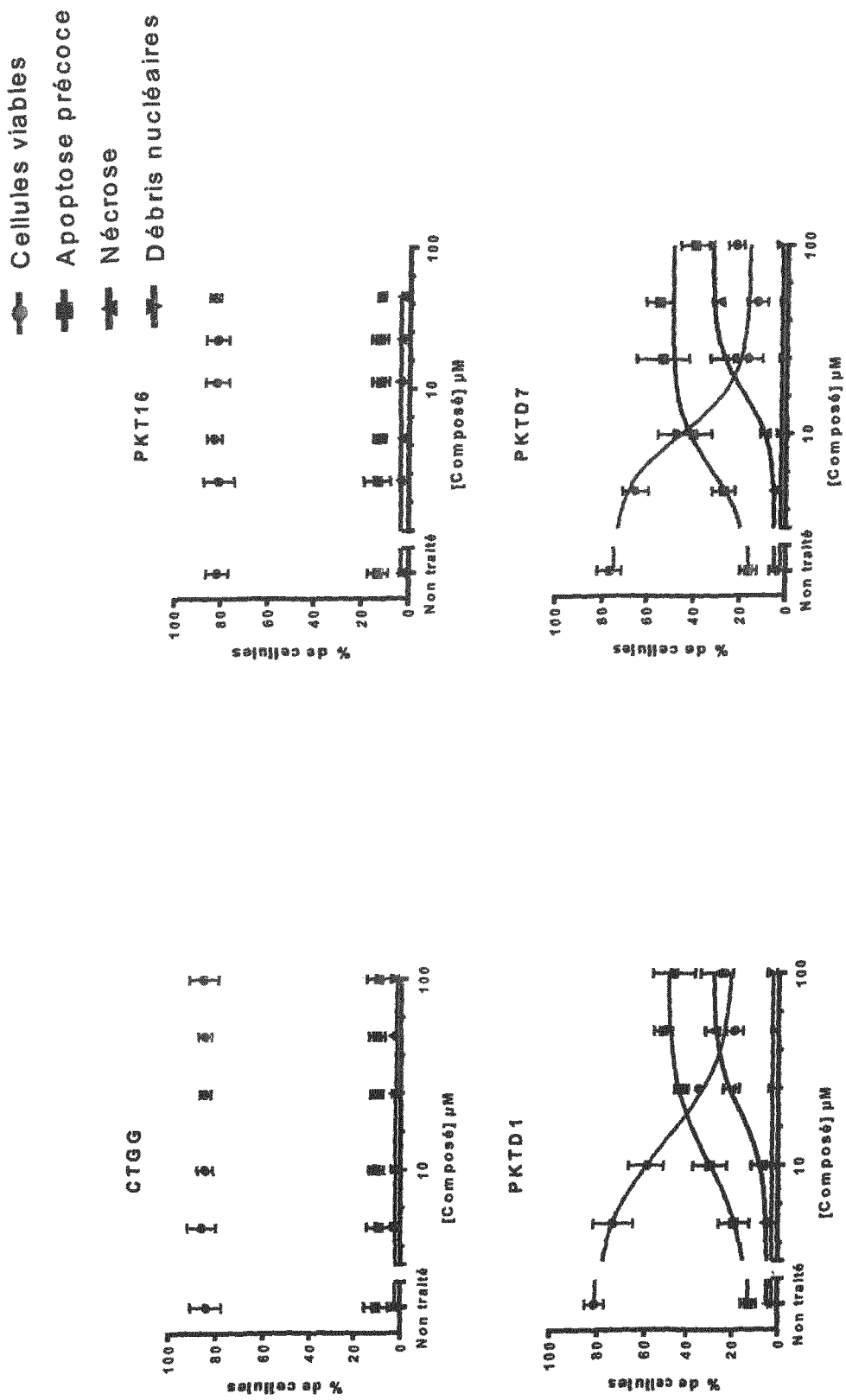
Assays on MCF7
Figure 7D(1)

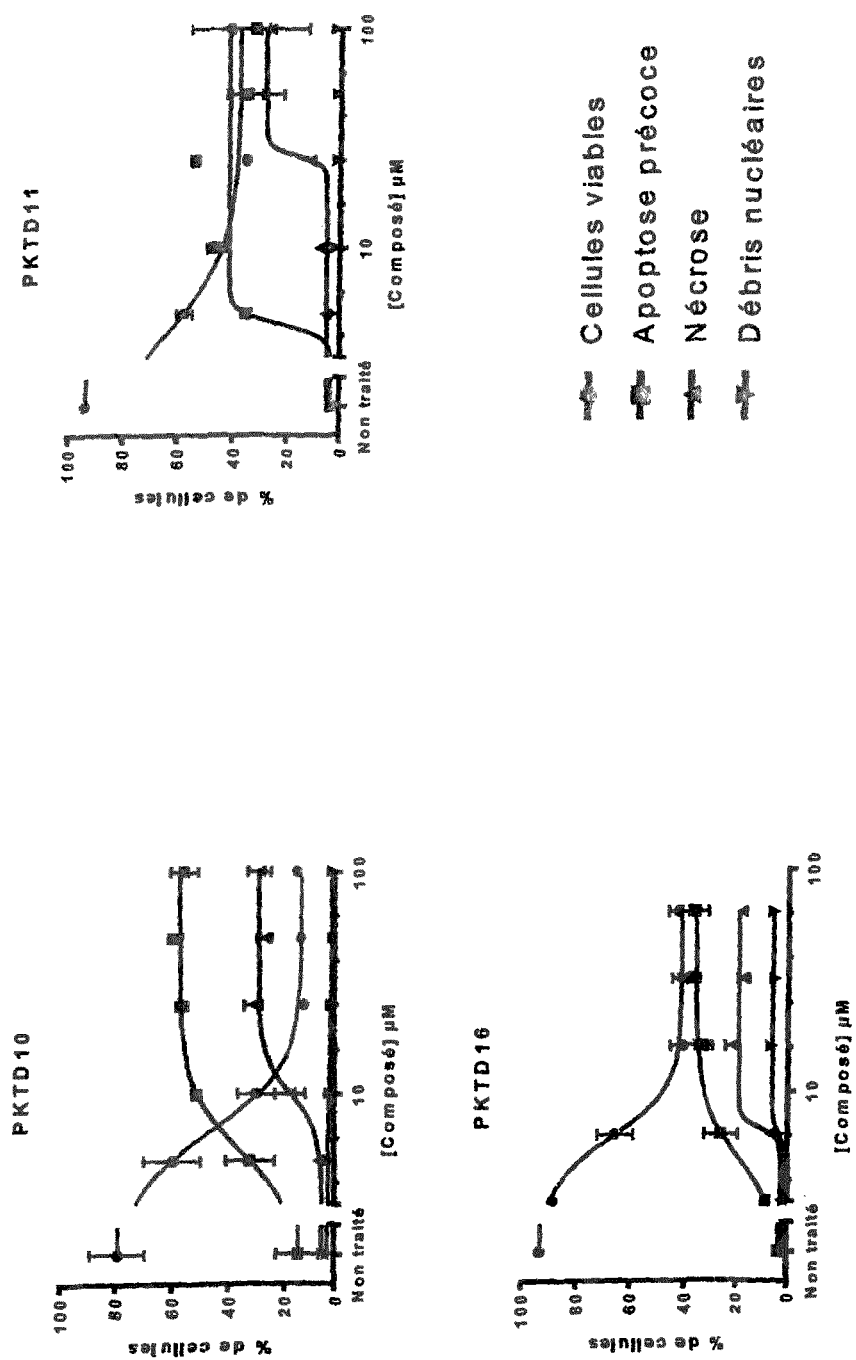
Assays on MCF7
Figure 7D(2)

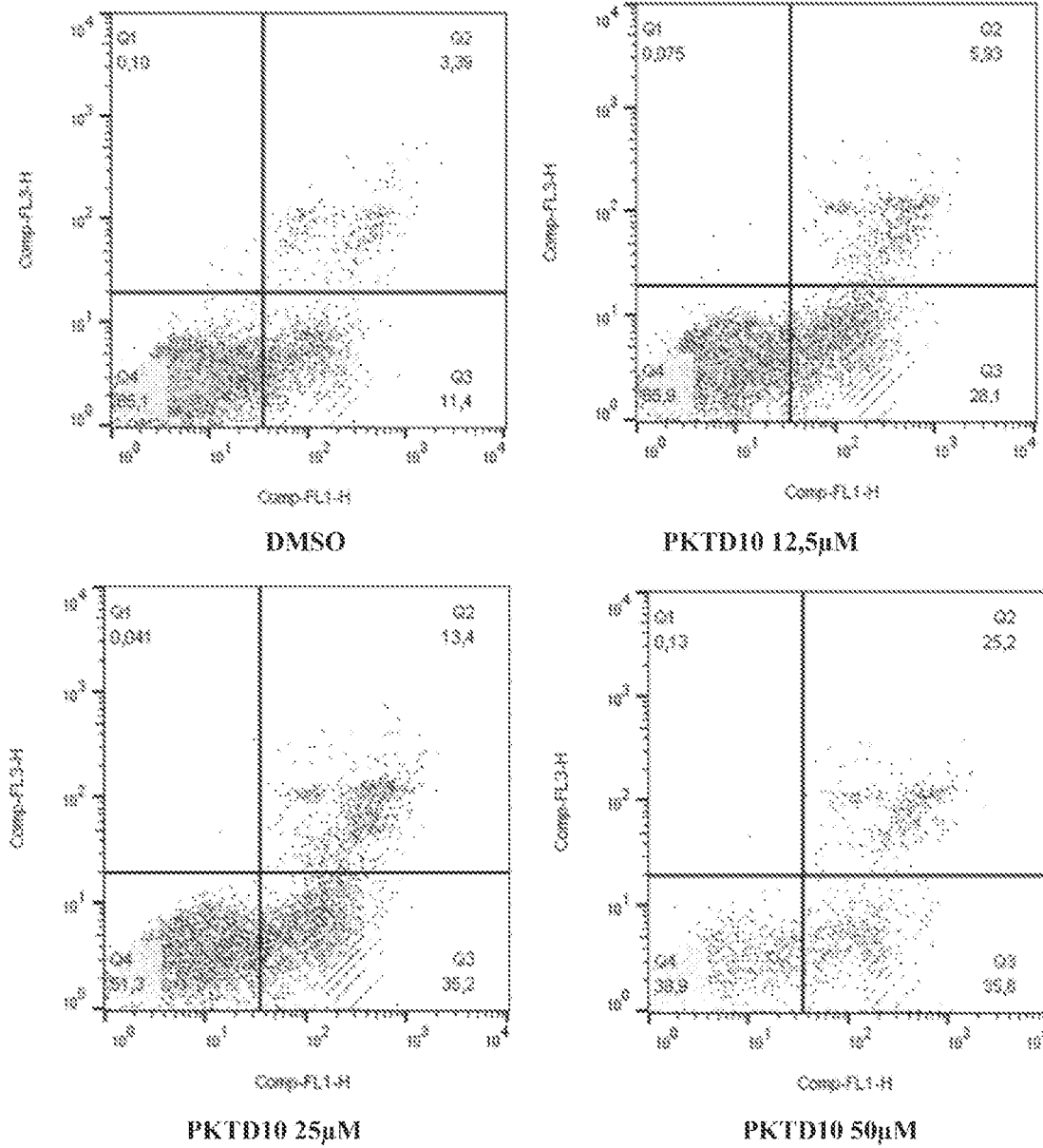
Figure 7E(1)

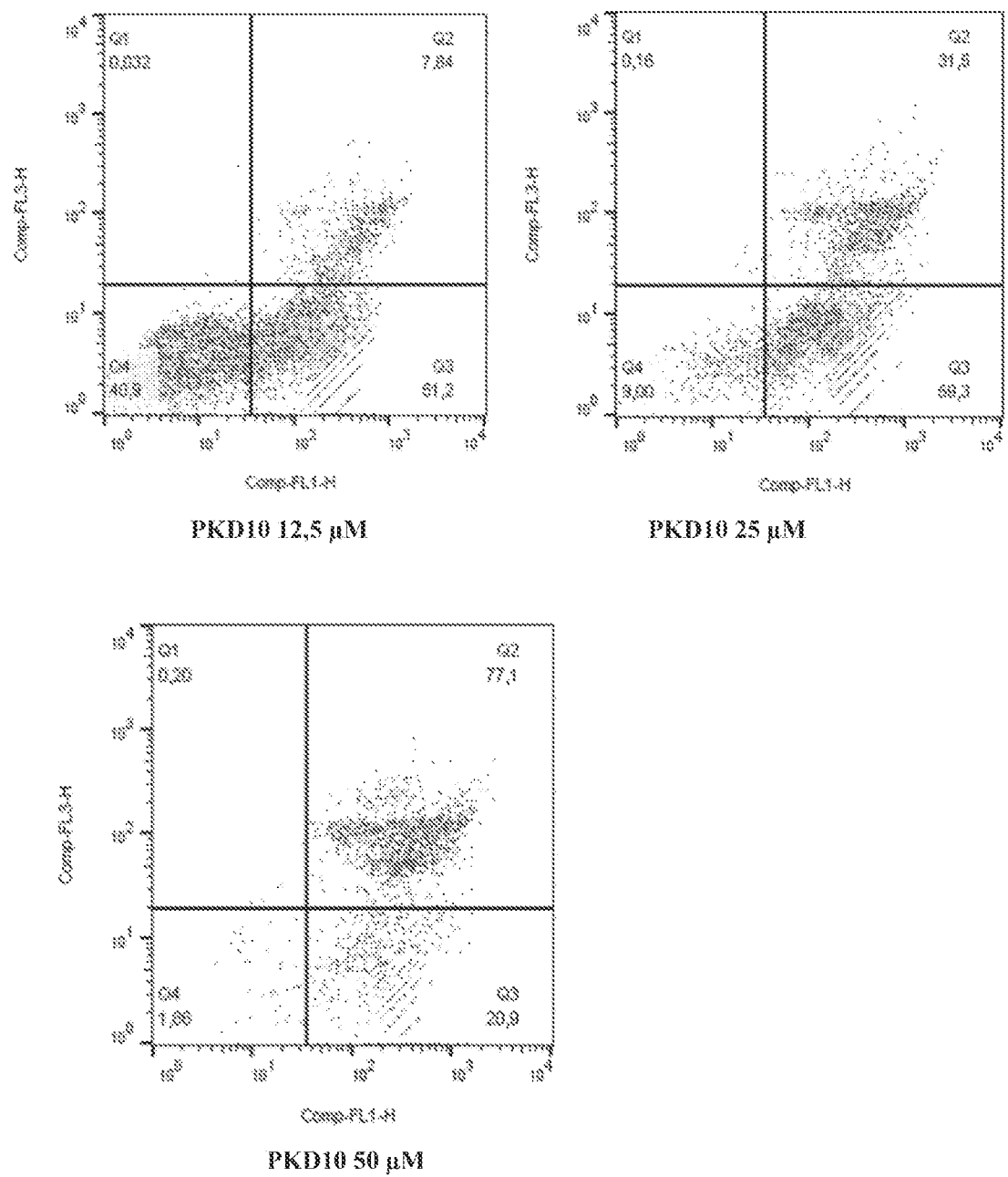
Figure 7E(2)

SEQUENCE LISTING

```
<160> NUMBER OF SEQ ID NOS: 66

<210> SEQ ID NO 1
<211> LENGTH: 6
<212> TYPE: PRT
<213> ORGANISM: Homo sapiens

<400> SEQUENCE: 1

Tyr Ala Gly Phe Val Phe
1               5

<210> SEQ ID NO 2
<211> LENGTH: 10
<212> TYPE: PRT
<213> ORGANISM: Artificial Sequence
<220> FEATURE:
<223> OTHER INFORMATION: derived from homo sapiens
<220> FEATURE:
<221> NAME/KEY: VARIANT
<222> LOCATION: (1)..(1)
<223> OTHER INFORMATION: replace: nothing or glycine or alanine or
      threonine or amino acid with similar properties
<220> FEATURE:
<221> NAME/KEY: VARIANT
<222> LOCATION: (2)..(2)
<223> OTHER INFORMATION: replace: nothing or homoarginine, lysine,
      ornithine, phenylalanine, naphtylalanine, N-methyl arginine or
      homophnylalanine or other ring substituted analogues in ortho,
      meta or para position
<220> FEATURE:
<221> NAME/KEY: VARIANT
<222> LOCATION: (3)..(3)
<223> OTHER INFORMATION: replace: naphtylalanine, homophenylalanine or
      other ring substituted analogues in ortho, meta or para position
      such as para-fluoro-phenylalanine, para-amino-phenylalanine or
      para-nitro-phenylalanine; tyrosine or amino acid with aromatic
<220> FEATURE:
<221> NAME/KEY: VARIANT
<222> LOCATION: (4)..(4)
<223> OTHER INFORMATION: replace: amino acid with aromatic side chains
      or phenylalanine or amino acid with similar properties including
      naphtylalanine, homophenylalanine or other ring substituted
      analogues in ortho, meta or para position
<220> FEATURE:
<221> NAME/KEY: VARIANT
<222> LOCATION: (5)..(5)
<223> OTHER INFORMATION: replace: leucine or isoleucine or terleucine or
      methionine or amino acid with similar properties
<220> FEATURE:
<221> NAME/KEY: VARIANT
<222> LOCATION: (6)..(6)
<223> OTHER INFORMATION: replace: leucine or isoleucine or terleucine or
      methionine or amino acid with similar properties
```

```
<220> FEATURE:
<221> NAME/KEY: VARIANT
<222> LOCATION: (7)..(7)
<223> OTHER INFORMATION: replace: valine or methionine or norleucine or
      leucine or isoleucine or lysine or terleucine or amino acid with
      similar properties
<220> FEATURE:
<221> NAME/KEY: VARIANT
<222> LOCATION: (8)..(8)
<223> OTHER INFORMATION: replace: tyrosine or phenylalanine or naphthyl-
      alanine or para-fluoro-phenylalanine or para-amino-phenylalanine
      or para-nitro-phenylalanine or D-prolino-tryptophane
<220> FEATURE:
<221> NAME/KEY: VARIANT
<222> LOCATION: (9)..(9)
<223> OTHER INFORMATION: replace: nothing or arginine or homoarginine or
      ornithine or phenylalanine or naphtylalanine or N-methyl arginine
      or homophnylalanine or other ring substituted analogues in ortho,
      meta or para position or histidine
<220> FEATURE:
<221> NAME/KEY: VARIANT
<222> LOCATION: (10)..(10)
<223> OTHER INFORMATION: replace: nothing or asparagine or or alanine or
      amino acid with similar properties

<400> SEQUENCE: 2

Ser Arg Phe Tyr Val Val Met Trp Lys Gln
1               5                   10

<210> SEQ ID NO 3
<211> LENGTH: 8
<212> TYPE: PRT
<213> ORGANISM: Homo sapiens

<400> SEQUENCE: 3

Arg Phe Tyr Val Val Met Trp Lys
1               5

<210> SEQ ID NO 4
<211> LENGTH: 9
<212> TYPE: PRT
<213> ORGANISM: Homo sapiens

<400> SEQUENCE: 4

Gly Leu Ser Val Lys Val Val Asn Ser
1               5

<210> SEQ ID NO 5
<211> LENGTH: 7
<212> TYPE: PRT
<213> ORGANISM: Artificial Sequence
<220> FEATURE:
<223> OTHER INFORMATION: homo sapiens

<400> SEQUENCE: 5

Tyr Ala Gly Phe Val Phe Gly
1               5

<210> SEQ ID NO 6
<211> LENGTH: 10
<212> TYPE: PRT
<213> ORGANISM: Homo sapiens
<220> FEATURE:
<221> NAME/KEY: VARIANT
<222> LOCATION: (1)..(1)
<223> OTHER INFORMATION: replace: nothing or glutamic acid or amino acid
      with similar properties
<220> FEATURE:
<221> NAME/KEY: VARIANT
<222> LOCATION: (9)..(9)
<223> OTHER INFORMATION: replace: nothing or amino acid with aromatic
```

```
      side chains
<220> FEATURE:
<221> NAME/KEY: VARIANT
<222> LOCATION: (10)..(10)
<223> OTHER INFORMATION: replace: nothing or glycine or amino acid with
      similar properties

<400> SEQUENCE: 6

Asp Tyr Ala Gly Phe Val Phe Gly Tyr Ser
1               5                   10

<210> SEQ ID NO 7
<211> LENGTH: 9
<212> TYPE: PRT
<213> ORGANISM: Homo sapiens
<220> FEATURE:
<221> NAME/KEY: VARIANT
<222> LOCATION: (1)..(1)
<223> OTHER INFORMATION: replace: nothing or serine or amino acid with
      similar properties
<220> FEATURE:
<221> NAME/KEY: VARIANT
<222> LOCATION: (2)..(2)
<223> OTHER INFORMATION: replace: leucine, terleucine, valine,
      methionine or any amino acid with similar properties
<220> FEATURE:
<221> NAME/KEY: VARIANT
<222> LOCATION: (5)..(5)
<223> OTHER INFORMATION: replace: arginine, homoarginine, lysine,
      ornithine, phenylalanine, naphtylalanine, N-methyl arginine or
      homophnylalanine or other ring substituted analogues (ortho,
      meta, para), histidine, methionine, valine, leucine, isoleucine,
<220> FEATURE:
<221> NAME/KEY: VARIANT
<222> LOCATION: (8)..(8)
<223> OTHER INFORMATION: replace: glutamine, lysine arginine,
      homoarginine, lysine, ornithine, phenylalanine, naphtylalanine,
      N-methyl arginine, homophnylalanine or any other ring substituted
      analogues (ortho, meta, para), histidine
<220> FEATURE:
<221> NAME/KEY: VARIANT
<222> LOCATION: (9)..(9)
<223> OTHER INFORMATION: replace: nothing or glycine

<400> SEQUENCE: 7

Gly Ile Ser Val Lys Val Val Asn Ser
1               5

<210> SEQ ID NO 8
<211> LENGTH: 8
<212> TYPE: PRT
<213> ORGANISM: Homo sapiens
<220> FEATURE:
<221> NAME/KEY: MISC_FEATURE
<222> LOCATION: (1)..(8)
<223> OTHER INFORMATION: cyclic peptide

<400> SEQUENCE: 8

Arg Phe Tyr Val Val Met Trp Lys
1               5

<210> SEQ ID NO 9
<211> LENGTH: 20
<212> TYPE: PRT
<213> ORGANISM: Homo sapiens
<220> FEATURE:
<221> NAME/KEY: MISC_FEATURE
<222> LOCATION: (1)..(20)
<223> OTHER INFORMATION: cyclic peptide
<220> FEATURE:
<221> NAME/KEY: VARIANT
<222> LOCATION: (10)..(10)
<223> OTHER INFORMATION: D-proline
```

```
<400> SEQUENCE: 9

Ser Arg Phe Tyr Val Val Met Trp Lys Pro Pro Gly Ile Ser Val Lys
1               5                   10                  15

Val Val Lys Ser
            20

<210> SEQ ID NO 10
<211> LENGTH: 20
<212> TYPE: PRT
<213> ORGANISM: Homo sapiens
<220> FEATURE:
<221> NAME/KEY: MISC_FEATURE
<222> LOCATION: (1)..(20)
<223> OTHER INFORMATION: cyclic peptide
<220> FEATURE:
<221> NAME/KEY: VARIANT
<222> LOCATION: (10)..(10)
<223> OTHER INFORMATION: D-proline

<400> SEQUENCE: 10

Ser Arg Phe Tyr Val Val Met Trp Lys Pro Pro Gly Ile Ser Ala Lys
1               5                   10                  15

Val Val Lys Ser
            20

<210> SEQ ID NO 11
<211> LENGTH: 20
<212> TYPE: PRT
<213> ORGANISM: Homo sapiens
<220> FEATURE:
<221> NAME/KEY: MISC_FEATURE
<222> LOCATION: (1)..(20)
<223> OTHER INFORMATION: cyclic peptide
<220> FEATURE:
<221> NAME/KEY: VARIANT
<222> LOCATION: (10)..(10)
<223> OTHER INFORMATION: D-proline

<400> SEQUENCE: 11

Asp Tyr Ala Gly Phe Val Phe Gly Tyr Pro Pro Arg Phe Tyr Val Val
1               5                   10                  15

Met Trp Lys Gln
            20

<210> SEQ ID NO 12
<211> LENGTH: 18
<212> TYPE: PRT
<213> ORGANISM: Homo sapiens
<220> FEATURE:
<221> NAME/KEY: MISC_FEATURE
<222> LOCATION: (1)..(18)
<223> OTHER INFORMATION: cyclic peptide
<220> FEATURE:
<221> NAME/KEY: VARIANT
<222> LOCATION: (9)..(9)
<223> OTHER INFORMATION: D-proline

<400> SEQUENCE: 12

Tyr Ala Gly Phe Val Phe Gly Tyr Pro Pro Arg Phe Tyr Val Val Met
1               5                   10                  15

Trp Lys

<210> SEQ ID NO 13
<211> LENGTH: 20
<212> TYPE: PRT
<213> ORGANISM: Homo sapiens
```

```
<220> FEATURE:
<221> NAME/KEY: MISC_FEATURE
<222> LOCATION: (1)..(20)
<223> OTHER INFORMATION: cyclic peptide
<220> FEATURE:
<221> NAME/KEY: VARIANT
<222> LOCATION: (10)..(10)
<223> OTHER INFORMATION: D-proline

<400> SEQUENCE: 13

Ser Arg Phe Tyr Val Val Met Trp Lys Pro Pro Gly Ile Ser Val Lys
1               5                   10                  15

Val Val Asn Ser
            20

<210> SEQ ID NO 14
<211> LENGTH: 18
<212> TYPE: PRT
<213> ORGANISM: Homo sapiens
<220> FEATURE:
<221> NAME/KEY: MISC_FEATURE
<222> LOCATION: (1)..(18)
<223> OTHER INFORMATION: cyclic peptide
<220> FEATURE:
<221> NAME/KEY: VARIANT
<222> LOCATION: (9)..(9)
<223> OTHER INFORMATION: D-proline

<400> SEQUENCE: 14

Arg Phe Tyr Val Val Met Trp Lys Pro Pro Gly Ile Ser Val Lys Val
1               5                   10                  15

Val Asn

<210> SEQ ID NO 15
<211> LENGTH: 22
<212> TYPE: PRT
<213> ORGANISM: Homo sapiens
<220> FEATURE:
<221> NAME/KEY: MISC_FEATURE
<222> LOCATION: (1)..(22)
<223> OTHER INFORMATION: cyclic peptide
<220> FEATURE:
<221> NAME/KEY: VARIANT
<222> LOCATION: (11)..(11)
<223> OTHER INFORMATION: D-proline

<400> SEQUENCE: 15

Asp Tyr Ala Gly Phe Val Phe Gly Tyr Gln Pro Pro Ser Arg Phe Tyr
1               5                   10                  15

Val Val Met Trp Lys Gln
            20

<210> SEQ ID NO 16
<211> LENGTH: 20
<212> TYPE: PRT
<213> ORGANISM: Homo sapiens
<220> FEATURE:
<221> NAME/KEY: MISC_FEATURE
<222> LOCATION: (1)..(20)
<223> OTHER INFORMATION: cyclic peptide
<220> FEATURE:
<221> NAME/KEY: VARIANT
<222> LOCATION: (10)..(10)
<223> OTHER INFORMATION: D-proline

<400> SEQUENCE: 16

Tyr Ala Gly Phe Val Phe Gly Tyr Gln Pro Pro Ser Arg Phe Tyr Val
1               5                   10                  15
```

Val Met Trp Lys
            20

<210> SEQ ID NO 17
<211> LENGTH: 20
<212> TYPE: PRT
<213> ORGANISM: Homo sapiens
<220> FEATURE:
<221> NAME/KEY: MISC_FEATURE
<222> LOCATION: (1)..(20)
<223> OTHER INFORMATION: cyclic peptide
<220> FEATURE:
<221> NAME/KEY: VARIANT
<222> LOCATION: (10)..(10)
<223> OTHER INFORMATION: D-proline

<400> SEQUENCE: 17

Ser Arg Phe Tyr Val Val Met Trp Lys Pro Pro Gly Leu Ser Val Lys
1               5                   10                  15

Val Val Asn Ser
            20

<210> SEQ ID NO 18
<211> LENGTH: 20
<212> TYPE: PRT
<213> ORGANISM: Homo sapiens
<220> FEATURE:
<221> NAME/KEY: MISC_FEATURE
<222> LOCATION: (1)..(20)
<223> OTHER INFORMATION: cyclic peptide
<220> FEATURE:
<221> NAME/KEY: VARIANT
<222> LOCATION: (10)..(10)
<223> OTHER INFORMATION: D-proline

<400> SEQUENCE: 18

Ser Arg Phe Tyr Val Val Met Trp Lys Pro Pro Ala Leu Ser Val Lys
1               5                   10                  15

Val Val Asn Ser
            20

<210> SEQ ID NO 19
<211> LENGTH: 20
<212> TYPE: PRT
<213> ORGANISM: Homo sapiens
<220> FEATURE:
<221> NAME/KEY: MISC_FEATURE
<222> LOCATION: (1)..(20)
<223> OTHER INFORMATION: cyclic peptide
<220> FEATURE:
<221> NAME/KEY: VARIANT
<222> LOCATION: (10)..(10)
<223> OTHER INFORMATION: D-proline

<400> SEQUENCE: 19

Ser Arg Phe Tyr Val Val Met Trp Lys Pro Pro Gly Ala Ser Val Lys
1               5                   10                  15

Val Val Asn Ser
            20

<210> SEQ ID NO 20
<211> LENGTH: 20
<212> TYPE: PRT
<213> ORGANISM: Homo sapiens
<220> FEATURE:
<221> NAME/KEY: MISC_FEATURE
<222> LOCATION: (1)..(20)
<223> OTHER INFORMATION: cyclic peptide
<220> FEATURE:

```
<221> NAME/KEY: VARIANT
<222> LOCATION: (10)..(10)
<223> OTHER INFORMATION: D-proline

<400> SEQUENCE: 20

Ser Arg Phe Tyr Val Val Met Trp Lys Pro Pro Gly Leu Ala Val Lys
1               5                   10                  15

Val Val Asn Ser
            20

<210> SEQ ID NO 21
<211> LENGTH: 20
<212> TYPE: PRT
<213> ORGANISM: Homo sapiens
<220> FEATURE:
<221> NAME/KEY: MISC_FEATURE
<222> LOCATION: (1)..(20)
<223> OTHER INFORMATION: cyclic peptide
<220> FEATURE:
<221> NAME/KEY: VARIANT
<222> LOCATION: (10)..(10)
<223> OTHER INFORMATION: D-proline

<400> SEQUENCE: 21

Ser Arg Phe Tyr Val Val Met Trp Lys Pro Pro Gly Leu Ser Ala Lys
1               5                   10                  15

Val Val Asn Ser
            20

<210> SEQ ID NO 22
<211> LENGTH: 20
<212> TYPE: PRT
<213> ORGANISM: Homo sapiens
<220> FEATURE:
<221> NAME/KEY: MISC_FEATURE
<222> LOCATION: (1)..(20)
<223> OTHER INFORMATION: cyclic peptide
<220> FEATURE:
<221> NAME/KEY: VARIANT
<222> LOCATION: (10)..(10)
<223> OTHER INFORMATION: D-proline

<400> SEQUENCE: 22

Ser Arg Phe Tyr Val Val Met Trp Lys Pro Pro Gly Leu Ser Val Ala
1               5                   10                  15

Val Val Asn Ser
            20

<210> SEQ ID NO 23
<211> LENGTH: 20
<212> TYPE: PRT
<213> ORGANISM: Homo sapiens
<220> FEATURE:
<221> NAME/KEY: MISC_FEATURE
<222> LOCATION: (1)..(20)
<223> OTHER INFORMATION: cyclic peptide
<220> FEATURE:
<221> NAME/KEY: VARIANT
<222> LOCATION: (10)..(10)
<223> OTHER INFORMATION: D-proline

<400> SEQUENCE: 23

Ser Arg Phe Tyr Val Val Met Trp Lys Pro Pro Gly Leu Ser Val Lys
1               5                   10                  15

Ala Val Asn Ser
            20
```

```
<210> SEQ ID NO 24
<211> LENGTH: 20
<212> TYPE: PRT
<213> ORGANISM: Homo sapiens
<220> FEATURE:
<221> NAME/KEY: MISC_FEATURE
<222> LOCATION: (1)..(20)
<223> OTHER INFORMATION: cyclic peptide
<220> FEATURE:
<221> NAME/KEY: VARIANT
<222> LOCATION: (10)..(10)
<223> OTHER INFORMATION: D-proline

<400> SEQUENCE: 24

Ser Arg Phe Tyr Val Val Met Trp Lys Pro Pro Gly Leu Ser Val Lys
1               5                   10                  15

Val Ala Asn Ser
            20

<210> SEQ ID NO 25
<211> LENGTH: 20
<212> TYPE: PRT
<213> ORGANISM: Homo sapiens
<220> FEATURE:
<221> NAME/KEY: MISC_FEATURE
<222> LOCATION: (1)..(20)
<223> OTHER INFORMATION: cyclic peptide
<220> FEATURE:
<221> NAME/KEY: VARIANT
<222> LOCATION: (10)..(10)
<223> OTHER INFORMATION: D-proline

<400> SEQUENCE: 25

Ser Arg Phe Tyr Val Val Met Trp Lys Pro Pro Gly Leu Ser Val Lys
1               5                   10                  15

Val Val Ala Ser
            20

<210> SEQ ID NO 26
<211> LENGTH: 20
<212> TYPE: PRT
<213> ORGANISM: Homo sapiens
<220> FEATURE:
<221> NAME/KEY: MISC_FEATURE
<222> LOCATION: (1)..(20)
<223> OTHER INFORMATION: cyclic peptide
<220> FEATURE:
<221> NAME/KEY: VARIANT
<222> LOCATION: (10)..(10)
<223> OTHER INFORMATION: D-proline

<400> SEQUENCE: 26

Ser Arg Phe Tyr Val Val Met Trp Lys Pro Pro Gly Leu Ser Val Lys
1               5                   10                  15

Val Val Asn Ala
            20

<210> SEQ ID NO 27
<211> LENGTH: 20
<212> TYPE: PRT
<213> ORGANISM: Homo sapiens
<220> FEATURE:
<221> NAME/KEY: MISC_FEATURE
<222> LOCATION: (1)..(20)
<223> OTHER INFORMATION: cyclic peptide
<220> FEATURE:
<221> NAME/KEY: VARIANT
<222> LOCATION: (10)..(10)
<223> OTHER INFORMATION: D-proline
```

<400> SEQUENCE: 27

Ser Arg Phe Ala Val Val Met Trp Lys Pro Pro Gly Leu Ser Val Lys
1               5                   10                  15

Val Val Asn Ser
            20

<210> SEQ ID NO 28
<211> LENGTH: 22
<212> TYPE: PRT
<213> ORGANISM: Homo sapiens
<220> FEATURE:
<221> NAME/KEY: MISC_FEATURE
<222> LOCATION: (1)..(21)
<223> OTHER INFORMATION: cyclic peptide
<220> FEATURE:
<221> NAME/KEY: MISC_FEATURE
<222> LOCATION: (1)..(22)
<223> OTHER INFORMATION: cyclic peptide
<220> FEATURE:
<221> NAME/KEY: VARIANT
<222> LOCATION: (11)..(11)
<223> OTHER INFORMATION: D-proline

<400> SEQUENCE: 28

Ser Arg Phe Tyr Val Val Met Trp Lys Gln Pro Pro Ser Gly Leu Ser
1               5                   10                  15

Val Lys Val Val Asn Ser
            20

<210> SEQ ID NO 29
<211> LENGTH: 20
<212> TYPE: PRT
<213> ORGANISM: Homo sapiens
<220> FEATURE:
<221> NAME/KEY: MISC_FEATURE
<222> LOCATION: (1)..(20)
<223> OTHER INFORMATION: cyclic peptide
<220> FEATURE:
<221> NAME/KEY: VARIANT
<222> LOCATION: (10)..(10)
<223> OTHER INFORMATION: D-proline

<400> SEQUENCE: 29

Arg Phe Tyr Val Val Met Trp Lys Gln Pro Pro Ser Gly Leu Ser Val
1               5                   10                  15

Lys Val Val Asn
            20

<210> SEQ ID NO 30
<211> LENGTH: 18
<212> TYPE: PRT
<213> ORGANISM: Homo sapiens
<220> FEATURE:
<221> NAME/KEY: MISC_FEATURE
<222> LOCATION: (1)..(18)
<223> OTHER INFORMATION: cyclic peptide
<220> FEATURE:
<221> NAME/KEY: VARIANT
<222> LOCATION: (8)..(8)
<223> OTHER INFORMATION: D-proline

<400> SEQUENCE: 30

Tyr Ala Gly Phe Val Phe Gly Pro Pro Arg Phe Tyr Val Val Met Trp
1               5                   10                  15

Lys Gln

<210> SEQ ID NO 31

```
<211> LENGTH: 18
<212> TYPE: PRT
<213> ORGANISM: Homo sapiens
<220> FEATURE:
<221> NAME/KEY: MISC_FEATURE
<222> LOCATION: (1)..(18)
<223> OTHER INFORMATION: cyclic peptide
<220> FEATURE:
<221> NAME/KEY: VARIANT
<222> LOCATION: (9)..(9)
<223> OTHER INFORMATION: D-proline

<400> SEQUENCE: 31

Arg Phe Tyr Val Val Met Trp Lys Pro Pro Gly Leu Ser Val Met Val
1               5                   10                  15

Val Asn

<210> SEQ ID NO 32
<211> LENGTH: 18
<212> TYPE: PRT
<213> ORGANISM: Homo sapiens
<220> FEATURE:
<221> NAME/KEY: MISC_FEATURE
<222> LOCATION: (1)..(18)
<223> OTHER INFORMATION: cyclic peptide
<220> FEATURE:
<221> NAME/KEY: VARIANT
<222> LOCATION: (9)..(9)
<223> OTHER INFORMATION: D-proline

<400> SEQUENCE: 32

Arg Phe Tyr Val Val Met Trp Lys Pro Pro Gly Leu Ser Val Lys Val
1               5                   10                  15

Val Asn

<210> SEQ ID NO 33
<211> LENGTH: 20
<212> TYPE: PRT
<213> ORGANISM: Homo sapiens
<220> FEATURE:
<221> NAME/KEY: MISC_FEATURE
<222> LOCATION: (1)..(20)
<223> OTHER INFORMATION: cyclic peptide
<220> FEATURE:
<221> NAME/KEY: VARIANT
<222> LOCATION: (10)..(10)
<223> OTHER INFORMATION: D-proline

<400> SEQUENCE: 33

Ser Arg Phe Tyr Val Val Met Trp Lys Pro Pro Ser Arg Phe Tyr Val
1               5                   10                  15

Val Met Trp Lys
            20

<210> SEQ ID NO 34
<211> LENGTH: 18
<212> TYPE: PRT
<213> ORGANISM: Homo sapiens
<220> FEATURE:
<221> NAME/KEY: MISC_FEATURE
<222> LOCATION: (1)..(18)
<223> OTHER INFORMATION: cyclic peptide
<220> FEATURE:
<221> NAME/KEY: VARIANT
<222> LOCATION: (9)..(9)
<223> OTHER INFORMATION: D-proline

<400> SEQUENCE: 34

Arg Phe Tyr Val Val Met Trp Lys Pro Pro Arg Phe Tyr Val Val Met
```

```
1               5                   10                  15

Trp Lys

<210> SEQ ID NO 35
<211> LENGTH: 20
<212> TYPE: PRT
<213> ORGANISM: Homo sapiens
<220> FEATURE:
<221> NAME/KEY: MISC_FEATURE
<222> LOCATION: (1)..(20)
<223> OTHER INFORMATION: cyclic peptide
<220> FEATURE:
<221> NAME/KEY: VARIANT
<222> LOCATION: (10)..(10)
<223> OTHER INFORMATION: D-proline

<400> SEQUENCE: 35

Ser Arg Phe Tyr Val Val Met Trp Lys Pro Pro Gly Leu Ser Val Lys
1               5                   10                  15

Val Val Asn Gly
            20

<210> SEQ ID NO 36
<211> LENGTH: 10
<212> TYPE: PRT
<213> ORGANISM: Artificial sequence
<220> FEATURE:
<223> OTHER INFORMATION: derived from homo sapiens
<220> FEATURE:
<221> NAME/KEY: VARIANT
<222> LOCATION: (1)..(1)
<223> OTHER INFORMATION: replace: nothing or alanine or amino acid with
      similar properties
<220> FEATURE:
<221> NAME/KEY: VARIANT
<222> LOCATION: (2)..(2)
<223> OTHER INFORMATION: replace: nothing or alanine or amino acid with
      similar properties
<220> FEATURE:
<221> NAME/KEY: VARIANT
<222> LOCATION: (3)..(3)
<223> OTHER INFORMATION: replace: leucine or alanine or amino acid with
      similar properties
<220> FEATURE:
<221> NAME/KEY: VARIANT
<222> LOCATION: (4)..(4)
<223> OTHER INFORMATION: replace: alanine or amino acid with similar
      properties
<220> FEATURE:
<221> NAME/KEY: VARIANT
<222> LOCATION: (5)..(5)
<223> OTHER INFORMATION: replace: alanine or amino acid with similar
      properties
<220> FEATURE:
<221> NAME/KEY: VARIANT
<222> LOCATION: (6)..(6)
<223> OTHER INFORMATION: replace: alanine or amino acid with similar
      properties
<220> FEATURE:
<221> NAME/KEY: VARIANT
<222> LOCATION: (7)..(7)
<223> OTHER INFORMATION: replace: alanine or amino acid with similar
      properties
<220> FEATURE:
<221> NAME/KEY: VARIANT
<222> LOCATION: (8)..(8)
<223> OTHER INFORMATION: replace: alanine or amino acid with similar
      properties
<220> FEATURE:
<221> NAME/KEY: VARIANT
<222> LOCATION: (9)..(9)
<223> OTHER INFORMATION: replace: alanine or amino acid with similar
      properties
<220> FEATURE:
```

<221> NAME/KEY: VARIANT
<222> LOCATION: (10)..(10)
<223> OTHER INFORMATION: replace: nothing or glycine or amino acid with
      similar properties

<400> SEQUENCE: 36

Ser Gly Ile Ser Val Lys Val Val Asn Ser
1               5                   10

<210> SEQ ID NO 37
<211> LENGTH: 6
<212> TYPE: PRT
<213> ORGANISM: Homo sapiens

<400> SEQUENCE: 37

Phe Tyr Val Val Met Trp
1               5

<210> SEQ ID NO 38
<211> LENGTH: 6
<212> TYPE: PRT
<213> ORGANISM: homo sapiens

<400> SEQUENCE: 38

Leu Ser Val Lys Val Val
1               5

<210> SEQ ID NO 39
<211> LENGTH: 12
<212> TYPE: PRT
<213> ORGANISM: homo sapiens
<220> FEATURE:
<221> NAME/KEY: MISC_FEATURE
<223> OTHER INFORMATION: cyclic peptide

<400> SEQUENCE: 39

Phe Tyr Val Val Met Trp Leu Ser Val Lys Val Val
1               5                   10

<210> SEQ ID NO 40
<211> LENGTH: 12
<212> TYPE: PRT
<213> ORGANISM: homo sapiens
<220> FEATURE:
<221> NAME/KEY: MISC_FEATURE
<223> OTHER INFORMATION: cyclic peptide
<220> FEATURE:
<221> NAME/KEY: variant
<222> LOCATION: (6)..(6)
<223> OTHER INFORMATION: replace: D-prolino-tryptophane

<400> SEQUENCE: 40

Phe Tyr Val Val Met Xaa Leu Ser Val Lys Val Val
1               5                   10

<210> SEQ ID NO 41
<211> LENGTH: 14
<212> TYPE: PRT
<213> ORGANISM: homo sapiens
<220> FEATURE:
<221> NAME/KEY: MISC_FEATURE
<223> OTHER INFORMATION: cyclic peptide
<220> FEATURE:
<221> NAME/KEY: variant
<222> LOCATION: (7)..(7)
<223> OTHER INFORMATION: replace: D-proline

<400> SEQUENCE: 41

```
Phe Tyr Val Val Met Trp Pro Pro Leu Ser Val Lys Val Val
1               5                   10

<210> SEQ ID NO 42
<211> LENGTH: 14
<212> TYPE: PRT
<213> ORGANISM: homo sapiens
<220> FEATURE:
<221> NAME/KEY: MISC_FEATURE
<223> OTHER INFORMATION: cyclic peptide
<220> FEATURE:
<221> NAME/KEY: variant
<222> LOCATION: (7)..(7)
<223> OTHER INFORMATION: replace: D-proline

<400> SEQUENCE: 42

Phe Phe Val Val Met Trp Pro Pro Leu Ser Val Lys Val Val
1               5                   10

<210> SEQ ID NO 43
<211> LENGTH: 14
<212> TYPE: PRT
<213> ORGANISM: homo sapiens
<220> FEATURE:
<221> NAME/KEY: MISC_FEATURE
<223> OTHER INFORMATION: cyclic peptide
<220> FEATURE:
<221> NAME/KEY: VARIANT
<222> LOCATION: (5)..(5)
<223> OTHER INFORMATION: replace: norleucine
<220> FEATURE:
<221> NAME/KEY: VARIANT
<222> LOCATION: (7)..(7)
<223> OTHER INFORMATION: replace: D-proline

<400> SEQUENCE: 43

Phe Tyr Val Val Xaa Trp Pro Pro Leu Ser Val Lys Val Val
1               5                   10

<210> SEQ ID NO 44
<211> LENGTH: 14
<212> TYPE: PRT
<213> ORGANISM: homo sapiens
<220> FEATURE:
<221> NAME/KEY: MISC_FEATURE
<223> OTHER INFORMATION: cyclic peptide
<220> FEATURE:
<221> NAME/KEY: variant
<222> LOCATION: (7)..(7)
<223> OTHER INFORMATION: replace: D-proline

<400> SEQUENCE: 44

Phe Tyr Val Val Lys Trp Pro Pro Leu Ser Val Lys Val Val
1               5                   10

<210> SEQ ID NO 45
<211> LENGTH: 14
<212> TYPE: PRT
<213> ORGANISM: homo sapiens
<220> FEATURE:
<221> NAME/KEY: MISC_FEATURE
<223> OTHER INFORMATION: cyclic peptide
<220> FEATURE:
<221> NAME/KEY: variant
<222> LOCATION: (7)..(7)
<223> OTHER INFORMATION: replace: D-proline

<400> SEQUENCE: 45

Phe Phe Val Val Lys Trp Pro Pro Leu Ser Val Lys Val Val
1               5                   10
```

```
<210> SEQ ID NO 46
<211> LENGTH: 14
<212> TYPE: PRT
<213> ORGANISM: homo sapiens
<220> FEATURE:
<221> NAME/KEY: MISC_FEATURE
<223> OTHER INFORMATION: cyclic peptide
<220> FEATURE:
<221> NAME/KEY: variant
<222> LOCATION: (1)..(1)
<223> OTHER INFORMATION: replace: D-proline

<400> SEQUENCE: 46

Pro Pro Phe Tyr Val Val Met Trp Leu Ser Val Lys Val Val
1               5                   10

<210> SEQ ID NO 47
<211> LENGTH: 16
<212> TYPE: PRT
<213> ORGANISM: homo sapiens
<220> FEATURE:
<221> NAME/KEY: MISC_FEATURE
<223> OTHER INFORMATION: cyclic peptide
<220> FEATURE:
<221> NAME/KEY: variant
<222> LOCATION: (8)..(8)
<223> OTHER INFORMATION: replace: D-proline

<400> SEQUENCE: 47

Arg Phe Tyr Val Val Met Trp Pro Pro Leu Ser Val Lys Val Val Asn
1               5                   10                  15

<210> SEQ ID NO 48
<211> LENGTH: 16
<212> TYPE: PRT
<213> ORGANISM: homo sapiens
<220> FEATURE:
<221> NAME/KEY: MISC_FEATURE
<223> OTHER INFORMATION: cyclic peptide
<220> FEATURE:
<221> NAME/KEY: variant
<222> LOCATION: (1)..(1)
<223> OTHER INFORMATION: replace: N-Methyl arginine
<220> FEATURE:
<221> NAME/KEY: variant
<222> LOCATION: (8)..(8)
<223> OTHER INFORMATION: replace: D-proline

<400> SEQUENCE: 48

Arg Phe Tyr Val Val Met Trp Pro Pro Leu Ser Val Lys Val Val Asn
1               5                   10                  15

<210> SEQ ID NO 49
<211> LENGTH: 16
<212> TYPE: PRT
<213> ORGANISM: homo sapiens
<220> FEATURE:
<221> NAME/KEY: MISC_FEATURE
<223> OTHER INFORMATION: cyclic peptide
<220> FEATURE:
<221> NAME/KEY: variant
<222> LOCATION: (8)..(8)
<223> OTHER INFORMATION: replace: D-proline

<400> SEQUENCE: 49

Arg Phe Tyr Val Val Met Trp Pro Pro Ile Ser Val Lys Val Val Lys
1               5                   10                  15

<210> SEQ ID NO 50
<211> LENGTH: 16
```

```
<212> TYPE: PRT
<213> ORGANISM: homo sapiens
<220> FEATURE:
<221> NAME/KEY: MISC_FEATURE
<223> OTHER INFORMATION: cyclic peptide
<220> FEATURE:
<221> NAME/KEY: variant
<222> LOCATION: (1)..(1)
<223> OTHER INFORMATION: replace: N-methyl-arginine
<220> FEATURE:
<221> NAME/KEY: variant
<222> LOCATION: (8)..(8)
<223> OTHER INFORMATION: replace: D-proline

<400> SEQUENCE: 50

Arg Phe Tyr Val Val Met Trp Pro Pro Ile Ser Val Lys Val Val Lys
1               5                   10                  15

<210> SEQ ID NO 51
<211> LENGTH: 16
<212> TYPE: PRT
<213> ORGANISM: homo sapiens
<220> FEATURE:
<221> NAME/KEY: MISC_FEATURE
<223> OTHER INFORMATION: cyclic peptide
<220> FEATURE:
<221> NAME/KEY: variant
<222> LOCATION: (1)..(1)
<223> OTHER INFORMATION: replace: D-proline

<400> SEQUENCE: 51

Pro Pro Phe Tyr Val Val Met Trp Lys Gly Leu Ser Val Lys Val Val
1               5                   10                  15

<210> SEQ ID NO 52
<211> LENGTH: 16
<212> TYPE: PRT
<213> ORGANISM: homo sapiens
<220> FEATURE:
<221> NAME/KEY: MISC_FEATURE
<223> OTHER INFORMATION: cyclic peptide
<220> FEATURE:
<221> NAME/KEY: variant
<222> LOCATION: (1)..(1)
<223> OTHER INFORMATION: replace: D-proline

<400> SEQUENCE: 52

Pro Pro Arg Phe Tyr Val Val Met Trp Leu Ser Val Lys Val Val Asn
1               5                   10                  15

<210> SEQ ID NO 53
<211> LENGTH: 18
<212> TYPE: PRT
<213> ORGANISM: homo sapiens
<220> FEATURE:
<221> NAME/KEY: MISC_FEATURE
<223> OTHER INFORMATION: cyclic peptide
<220> FEATURE:
<221> NAME/KEY: variant
<222> LOCATION: (1)..(1)
<223> OTHER INFORMATION: replace: D-proline

<400> SEQUENCE: 53

Pro Pro Arg Phe Tyr Val Val Met Trp Lys Gly Leu Ser Val Lys Val
1               5                   10                  15

Val Asn

<210> SEQ ID NO 54
<211> LENGTH: 20
<212> TYPE: PRT
```

```
<213> ORGANISM: homo sapiens
<220> FEATURE:
<221> NAME/KEY: MISC_FEATURE
<223> OTHER INFORMATION: cyclic peptide
<220> FEATURE:
<221> NAME/KEY: variant
<222> LOCATION: (2)..(2)
<223> OTHER INFORMATION: replace: N-methyl-arginine
<220> FEATURE:
<221> NAME/KEY: variant
<222> LOCATION: (10)..(10)
<223> OTHER INFORMATION: replace: D-proline

<400> SEQUENCE: 54

Ser Arg Phe Tyr Val Val Met Trp Lys Pro Pro Gly Leu Ser Val Lys
1               5                   10                  15

Val Val Asn Ser
            20

<210> SEQ ID NO 55
<211> LENGTH: 20
<212> TYPE: PRT
<213> ORGANISM: homo sapiens
<220> FEATURE:
<221> NAME/KEY: MISC_FEATURE
<223> OTHER INFORMATION: cyclic peptide
<220> FEATURE:
<221> NAME/KEY: variant
<222> LOCATION: (2)..(2)
<223> OTHER INFORMATION: replace: N-methyl-arginine
<220> FEATURE:
<221> NAME/KEY: variant
<222> LOCATION: (7)..(7)
<223> OTHER INFORMATION: replace: norleucine
<220> FEATURE:
<221> NAME/KEY: variant
<222> LOCATION: (10)..(10)
<223> OTHER INFORMATION: replace: D-proline

<400> SEQUENCE: 55

Ser Arg Phe Tyr Val Val Xaa Trp Lys Pro Pro Gly Leu Ser Val Lys
1               5                   10                  15

Val Val Asn Ser
            20

<210> SEQ ID NO 56
<211> LENGTH: 20
<212> TYPE: PRT
<213> ORGANISM: homo sapiens
<220> FEATURE:
<221> NAME/KEY: MISC_FEATURE
<223> OTHER INFORMATION: cyclic peptide
<220> FEATURE:
<221> NAME/KEY: variant
<222> LOCATION: (2)..(2)
<223> OTHER INFORMATION: replace: N-methyl-arginine
<220> FEATURE:
<221> NAME/KEY: variant
<222> LOCATION: (7)..(7)
<223> OTHER INFORMATION: replace: norleucine
<220> FEATURE:
<221> NAME/KEY: variant
<222> LOCATION: (10)..(10)
<223> OTHER INFORMATION: replace: D-proline

<400> SEQUENCE: 56

Ser Arg Phe Tyr Val Val Xaa Trp Lys Pro Pro Gly Leu Ala Val Lys
1               5                   10                  15

Val Val Asn Ser
            20
```

<210> SEQ ID NO 57
<211> LENGTH: 20
<212> TYPE: PRT
<213> ORGANISM: homo sapiens
<220> FEATURE:
<221> NAME/KEY: MISC_FEATURE
<223> OTHER INFORMATION: cyclic peptide
<220> FEATURE:
<221> NAME/KEY: variant
<222> LOCATION: (1)..(1)
<223> OTHER INFORMATION: replace: D-proline

<400> SEQUENCE: 57

Pro Pro Ser Arg Phe Tyr Val Val Met Trp Lys Gly Leu Ser Val Lys
1               5                   10                  15

Val Val Asn Ser
            20

<210> SEQ ID NO 58
<211> LENGTH: 22
<212> TYPE: PRT
<213> ORGANISM: homo sapiens
<220> FEATURE:
<221> NAME/KEY: MISC_FEATURE
<223> OTHER INFORMATION: cyclic peptide
<220> FEATURE:
<221> NAME/KEY: MISC_FEATURE
<222> LOCATION: (11)..(11)
<223> OTHER INFORMATION: replace: D-proline

<400> SEQUENCE: 58

Ser Arg Phe Tyr Val Val Met Trp Lys Ala Pro Pro Ser Gly Leu Ser
1               5                   10                  15

Val Lys Val Val Asn Ser
            20

<210> SEQ ID NO 59
<211> LENGTH: 22
<212> TYPE: PRT
<213> ORGANISM: homo sapiens
<220> FEATURE:
<221> NAME/KEY: MISC_FEATURE
<223> OTHER INFORMATION: cyclic peptide
<220> FEATURE:
<221> NAME/KEY: variant
<222> LOCATION: (11)..(11)
<223> OTHER INFORMATION: replace: D-proline

<400> SEQUENCE: 59

Ser Arg Phe Tyr Val Val Met Trp Lys Gln Pro Pro Ala Gly Leu Ser
1               5                   10                  15

Val Lys Val Val Asn Ser
            20

<210> SEQ ID NO 60
<211> LENGTH: 22
<212> TYPE: PRT
<213> ORGANISM: homo sapiens
<220> FEATURE:
<221> NAME/KEY: MISC_FEATURE
<223> OTHER INFORMATION: cyclic peptide
<220> FEATURE:
<221> NAME/KEY: variant
<222> LOCATION: (2)..(2)
<223> OTHER INFORMATION: replace: N-methyl-arginine
<220> FEATURE:
<221> NAME/KEY: variant
<222> LOCATION: (11)..(11)
<223> OTHER INFORMATION: replace: D-proline -continued

<400> SEQUENCE: 60

Ser Arg Phe Tyr Val Val Met Trp Lys Gln Pro Ser Gly Leu Ser
1               5                   10                  15

Val Lys Val Val Asn Ser
            20

<210> SEQ ID NO 61
<211> LENGTH: 22
<212> TYPE: PRT
<213> ORGANISM: homo sapiens
<220> FEATURE:
<221> NAME/KEY: MISC_FEATURE
<223> OTHER INFORMATION: cyclic peptide
<220> FEATURE:
<221> NAME/KEY: variant
<222> LOCATION: (2)..(2)
<223> OTHER INFORMATION: replace: N-methyl-arginine
<220> FEATURE:
<221> NAME/KEY: variant
<222> LOCATION: (7)..(7)
<223> OTHER INFORMATION: replace: norleucine
<220> FEATURE:
<221> NAME/KEY: variant
<222> LOCATION: (11)..(11)
<223> OTHER INFORMATION: replace: D-proline

<400> SEQUENCE: 61

Ser Arg Phe Tyr Val Val Xaa Trp Lys Gln Pro Ser Gly Leu Ser
1               5                   10                  15

Val Lys Val Val Asn Ser
            20

<210> SEQ ID NO 62
<211> LENGTH: 11
<212> TYPE: PRT
<213> ORGANISM: Homo sapiens

<400> SEQUENCE: 62

Phe Ile Arg Val Val Met Tyr Glu Gly Lys Lys
1               5                   10

<210> SEQ ID NO 63
<211> LENGTH: 10
<212> TYPE: PRT
<213> ORGANISM: Homo sapiens

<400> SEQUENCE: 63

Lys Arg Phe Tyr Val Val Met Trp Lys Lys
1               5                   10

<210> SEQ ID NO 64
<211> LENGTH: 9
<212> TYPE: PRT
<213> ORGANISM: Homo sapiens

<400> SEQUENCE: 64

Lys Arg Phe Tyr Val Val Met Trp Lys
1               5

<210> SEQ ID NO 65
<211> LENGTH: 58
<212> TYPE: PRT
<213> ORGANISM: Homo sapiens

<400> SEQUENCE: 65

```
Lys Arg Phe Lys Gln Asp Gly Gly Trp Ser His Trp Ser Pro Trp Cys
1               5                   10                  15

Ser Val Thr Cys Gly Asp Gly Val Ile Thr Arg Ile Arg Leu Cys Asn
            20              25                  30

Ser Pro Ser Gln Met Asn Gly Lys Pro Cys Glu Gly Glu Ala Arg Glu
            35              40                  45

Thr Lys Ala Cys Lys Lys Asp Ala Cys Pro
    50              55
```

<210> SEQ ID NO 66
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Wherein the Arg at position 2 is methylated
<220> FEATURE:
<221> NAME/KEY: MISC_FEATURE
<222> LOCATION: (7)..(7)
<223> OTHER INFORMATION: Wherein the X at position 7 is defined as
      Norleucine (Nle)

<400> SEQUENCE: 66

```
Lys Arg Phe Tyr Val Val Xaa Trp Lys Lys
1               5                   10
```

AGONIST AGENTS OF CD47 INDUCING PROGRAMMED CELL DEATH AND THEIR USE IN THE TREATMENTS OF DISEASES ASSOCIATED WITH DEFECTS IN PROGRAMMED CELL DEATH

FIELD OF THE INVENTION

The present invention relates to cyclic peptides mimetics of the C-terminal binding domain of TSP-1.

The present invention also relates to the use of these cyclic peptides as agonists of CD47 and their ability to trigger programmed cell death (PCD).

The present invention also relate to a pharmaceutical composition for use in the treatment of diseases associated with defects in PCD such as cancers and immunological disorders (including chronic inflammation) and comprising at least one cyclic peptide according to the invention.

STATEMENT REGARDING SEQUENCE LISTING

The sequence listing associated with this application is provided in text format in lieu of a paper copy and is hereby incorporated by reference into the specification. The name of the text file containing the sequence listing is 2095-P183USPNP_Seq_List_FINAL_20211007_ST25.txt. The text file is 27 KB; was created on Oct. 7, 2021; and is being submitted via EFS-Web with the filing of the substitute specification.

BACKGROUND OF THE INVENTION

1—Role of PCD in Diseases

Programmed Cell Death (PCD) plays a fundamental role in development and regulation of tissue homeostasis such as sculpting structures and driving morphogenesis, regulating cell number, eliminating unwanted and potentially dangerous cells.[i]

Abnormal regulation of this process (i.e. excess or defect in PCD) is associated with a wide variety of human diseases, including development and immunological disorders, neurodegeneration and cancers.

Remarkable progresses have been made since 20 years to unravel, at the molecular level, the mechanisms by which an abnormal cell can escape PCD. Two pathways, i.e. the intrinsic and the extrinsic pathways, can trigger PCD in normal cell. Both pathways involve a cascade of protein-protein interactions (PPIs) and activations that results in a large variety of Programmed Cell Death types (see FIGS. 1 and 2). An imbalance in the anti- and pro-cell death protein interactions will lead to failure of cell death homeostasis, failure resulting in many diseases with excess or defect in PCD, such as at least cancers and immunological disorders.[ii]

2—Cancers and PCD Defects

Cancers are diseases characterized by an imbalance between cell division and cell death.[iii]

In cancer cells, the PCD blockage is mainly caused either by cytogenetic abnormalities leading to over-expression of anti-cell death proteins or down-regulation of pro-cell death proteins. More than 50,000 chromosomal aberrations (gains or losses) have been reported to date.[iv] Although focus has been on caspase-dependent apoptotic death pathways, it is known that non-apoptotic PCD also form an important barrier against tumor initiation and progression.[v] Akin to the earlier landmark discoveries that lead to the identification of the major cancer-related proteins like p53, c-Myc and Bcl-2 as controllers of spontaneous and therapy-induced apoptosis, numerous proteins with properties of tumor suppressors and onco-proteins have been identified as key regulators of alternative death programs. The emerging data on the molecular mechanisms regulating non-apoptotic PCD will have potent therapeutic consequences.[vi]

Carcinogenesis is also associated with inflammation that is a defensive process against tissue injury (Zenaida Lopez-Dee, Kenneth Pidcock, and Linda S. Gutierrez in "Thrombospondin-1: Multiple Path to inflammation, Mediators of Inflammation, Volume 2011, Article ID 296069, 10 pages doi:10.1155/2011/296069). Once this self-protective strategy is initiated, an effective resolution of the process is crucial to avoid major and unnecessary tissue damage. If the underlying event inducing inflammation is not addressed and homeostasis is not restored, the inflammation process become chronic and lead to angiogenesis, carcinogenesis and diseases associated with chronic inflammation, such as for example, multiple sclerosis, Crohn disease, psoriasis, ulcerative colitis, arthritis and asthma, that are autoimmune diseases.[vii]

3—Immunological Disorders, Autoimmune Diseases and Defects in PCD

A common feature of autoimmune diseases is altered tolerance to self-antigens and generation of autoantibodies Immune homeostasis and maintenance of immune tolerance are strongly dependent on apoptosis. A large number of evidence support the idea that defective apoptosis of immune cells leads to autoimmune disease. Lpr and gld mice defective for the Fas signaling pathway develop lymphoadenopathy and splenomegaly and produce a large number of autoantibodies developing a disease that resembles human systemic lupus erythematosus (SLE), clearly demonstrating an essential role for the extrinsic apoptotic pathway in controlling auto-reactive T and B cells and the fact that alteration in apoptosis can strongly contribute to autoimmune diseases pathogenesis.[viii] In humans defects of the Fas signaling pathway lead to the autoimmune lymphoproliferative syndrome (ALPS) characterized by non-malignant lymphoproliferation and autoimmunity and have increased incidence of malignancies. 70% of these patients carry germline heterozygous FAS mutations, while the rest have somatic FAS mutations or mutations of FAS ligand, caspase 10 and caspase 8. In most cases mutations function as dominant negatives inhibiting also the function of the wild type protein.[ix]

While defects in the extrinsic pathway seem to play a major role in the immune system it is becoming clear that also the intrinsic pathway participates and its alterations can contribute to autoimmune disease pathogenesis.[x] As an example Bim KO mice have been shown to accumulate lymphoid and myeloid cells and develop an autoimmune disease.[xi] While no mutations of the BH3 only proteins have been described in patients with autoimmune diseases, reduced levels of Bim were reported in a patient with ALPS and over-expression of pro-survival members of the bcl2 family have been reported in SLE.[xii]

In view of these elements, identifying highly efficient ingredients able to trigger Programmed Cell Death in diseases associated more specifically with defects in PCD and unwanted cell proliferation is crucial.

4—State of the Art

Thanks to the X-Ray resolution of the crystal structure of the proteins involved in the PCD regulation, many small molecules have been designed to target protein-protein interactions (PPI) and to restore PCD. Some key examples are the Nutlins, which target the p53-MDM2 complex,[xiii] Navitoclax,[xiv] a BH3 mimetic targeting anti-apoptotic proteins of the BCl-2 family, or the inhibitors of the SMAC/XIAP interaction.[xv] In the case of the p53-MDM2 complex, many peptides and peptide mimics of p53 3D structure, which are able to interact with MDM2, have also been designed as disrupters of PPI with a great in vitro success. However, as peptides and mimics usually exhibit poor cell permeability, it will now be interesting to see whether such peptides display a similar p53-MDM2 disrupting activity in vivo.[xvi] Of note, both small molecules and peptide approaches remain ineffective to trigger PCD in case of TP53 deletion, a frequent cytogenetic alteration that is associated with poor prognosis.[xvii] Most of all, decoding the human protein-protein interactome network over recent years highlighted the limit of therapeutic agents designed to interact with a single pathway, inevitably resulting in the activation of compensatory mechanisms which allow PCD escape and restore disease progression.[xviii] Be that as it may, a peptide approach would be more relevant by addressing an extracellular target to answer the membrane permeability problem. Moreover, to overcome the compensatory mechanism, addressing a target located upstream of a signaling pathway and able to irreversibly trigger PCD might be more efficient.

As mentioned above, identifying highly efficient ingredients able to trigger Programmed Cell Death in diseases associated more specifically with defects in PCD and unwanted cell proliferation is crucial. This objective is reached by the present invention since the inventors have surprisingly demonstrated that TSP-1 cyclic agonist peptides trigger PCD of cancer cells with high efficiency.

5—Thrombospondins and TSP-1

TSP-1 is a matricellular protein of 450 kD that was first isolated in activated platelets and described as a glycoprotein by Lawler and al in 1978.[xix] In 1994 and 1996, Gao and coworkers have described the TSP-1 as an endogenous ligand for CD47[xx, xxi] TSP-1 belongs to a family of multi-domains calcium-binding glycoproteins composed of five different members.

TSP-1 has several domains that bind to different cell membrane receptors or extracellular matrix, which mediates cell-cell and cell-extracellular matrix interactions. It contains an N-terminal globular domain, three disulfide-linked chains (the type I (properdin-like repeats), type II (epidermal growth factor-like), and type III (calcium binding) repeats) and a C-terminal globular domain. The N-terminal domain interacts with low-density lipoprotein receptor-related protein, heparin and several integrins. Type I repeats or thrombospondin structural homology repeats (TSRs), bind CD36, collagen type V, fibronectin, and heparan sulfate proteoglycans. The type III repeats are calcium-binding domains that bind to β3 integrins through an RGD motif on TSP-1 411. Finally, the C-terminal domain of TSP-1 binds to CD47 (see Gao and Frazier).

Using overlapping peptides synthesized from the C-terminal cell-binding domain (CBD) of the TSP-1, Gao and Frazier found two homologous cell-binding sequences that contained the VVM motif, and they found this site essential for TSP-1/CD47 binding.[xxii] This discovery resulted in the development of short peptides corresponding to the sequences of the TSP-1 with the VVM motif, including in the peptides 7N3 (1102-FIRVVMYEGKK-1112) (SEQ ID NO: 62) and 4N1 (1016-RFYVVMWK-1024) (SEQ ID NO: 3). The 4N1K peptide (K-RFYVVMWK-K) SEQ ID NO: 63) was developed later in order to improve 4N1 solubility without affecting CD47-binding.

6—TSP1/CD47 Interaction

Binding of TSP-1 to CD47 influences several fundamental cellular functions including cell migration and adhesion, cell proliferation or apoptosis and plays a role in the regulation of angiogenesis and inflammation.[xxiii]

To date the TSP-1/CD47 complex has not been resolved by X-ray structure. A molecular modeling study has been realized by Floquet et al. (see FIG. 3 drawn according to the drawing of Floquet et al.).[xxiv] In this study, the 4N1 sequence is described as hidden within a hydrophobic pocket of the TSP1, preventing any interaction with CD47. However when it is in close proximity to CD47 and the phospholipid bilayer, the hydrophobic cleft opens permitting the 4N1 recognition.

The biological consequences of CD47/TSP-1 ligation are very vast and depend of cell types, association with other molecules, conformation, distribution on the cell surface, the mode of engagement and the particular situation in which these points occur.

These roles are key in the regulation of the homeostasis of the organism and TSP1/CD47 interaction play a wide range of functions. Among them, one of potential therapeutic interest is the ability to induce cell death and exemplified here with cancer cells.

CD47-Mediated Programmed Cell Death

Intense research performed within the last years has demonstrated that several CD47 monoclonal antibodies (mAbs), and the C-terminal domain of the TSP-1 can induce CD47-mediated PCD in different cell types. Importantly, although SIRP-alpha soluble Fc fusion protein does not induce CD47-dependent cell death,[xxv] however one report stated that SIRP-α and γ bound onto the surface of beads could induce CD47-mediated PCD in two tumor cell lines.[xxvi] Of notice, CD47 was also found to associate with Fas through its extracellular IgV domain leading to the augmentation of Fas-mediated apoptosis.[xxvii]

The first studies describing CD47-mediated PCD were done in 1999, when it was found that CD47 engagement could induce cell death in primary chronic lymphocytic leukemia cells,[xxviii] acute T cell leukemia-derived cell line (Jurkat), and activated T cells.[xxix] However, this process was found to be very complex, as both groups found PCD-induction by the stimulation of CD47, but using different inductors. While Mateo and collaborators used coated B6H12 mAb, TSP-1 and the 4N1K peptide to induce PCD, Pettersen and coworkers used only soluble anti-CD47 mAbs, and they found that the Ad22 and 1F7 (but not B6H12 nor 2D3) mAbs induce cell death in Jurkat cells. Still, both groups found that soluble B6H12 was unable to induce cell death. This data denoted the importance of a complex regulation between the mode of CD47 engagement and cell death induction. These results were rapidly followed by the assessment of CD47-mediated PCD induction in other cell types. These assessments included different antiCD47 mAbs, TSP1, TSP1 C-term derived peptides (4N1 and 4N1K) and recombinant proteins (T3C1), used in soluble or coated forms.

CD47-Mediated PCD in Cancer Cells

CD47-mediated cell death induction was observed in multiple tumor cells such as acute lymphoblastic leukemia cells (CCRF-CEM cell line),[xxx] breast tumor cells (MCF-7 cell line),[xxxi] multiple myeloma cells (KPMM2 cell line),[xxxii] acute promyelocytic leukemia cells (NB4 and the ATRA-refractory NB4-LR1 cell line),[xxxiii] and histiocytic lymphoma cells (U937 cell line).[xxxiv] Moreover, the studies done in acute T-cell leukemia cells (jurkat)[xxxv,xxxvi,xxxvii] and primary CLL cells were intensified.[xxxviii,xxxix,xl,xli]

Most information about CD47-mediated PCD comes from cancer cells, principally Jurkat and CLL cells. The main characteristics of CD47-mediated PCD in cancer cells are: 1) fast process; 2) caspase-independent; 3) Mitochondria membrane depolarization without the release of proapoptotic proteins (cytochrome C, AIF, Smac/Diablo, Omi/Htra2, endonuclease G (EndoG)); 4) reactive oxygen species (ROS) production; 5) Phosphatidylserine exposure; 6) Plasma membrane permeabilization; 7) Absence of DNA fragmentation nor chromatin condensation.

CD47 as a Target to Eliminate Tumor Cells

CD47 was shown to be overexpressed in multiple types of cancer. Moreover, it has multiple roles in immune system evasion, migration, adhesion, proliferation, and cell death, so CD47 can be exploited as a key target for cancer therapy, in multiple forms as illustrated in FIG. 4: phagocytosis, stimulation of antitumor adaptative immune response, antibody dependent cellular cytotoxicity (ADCC), inhibition of CD47-dependent cellular functions and CD47-mediated PCD induction.

7—TSP-1 CBD Mimetics and their Use to Induce PCD and to Treat Diseases Associated with Defects in PCD In WO 2013/182650, it was demonstrated that 4N1K, a soluble decapeptide that mimics the C-terminal domain of TSP-1, induces caspase-independent PCD in B-chronic lymphocytic leukemia (CLL) primary cells by ligation with CD47. It was further demonstrated that, contrary to the anti-CD47 mAb which needs to be immobilized to induce PCD, the soluble 4N1K peptide does not need to be coated on plastic to induce caspase-independent PCD. It was found that a negative control peptide 4NGG (4N1K mutated in two amino acids) is unable to induce PCD, signifying the specificity of the 4N1K PCD induction. Moreover, It was discovered that CD47 ligation by 4N1K and its derivative PKHB1 specifically eliminates leukemic B-cells, and not healthy B-lymphocytes or resting normal B-cells from CLL patients and thus represents a better means of inducing death than caspase-dependent PCD (this form of death is effective even in CLL cells from drug refractory individuals bearing deletion on 17p13 or I lq22-q23: ATM/TP53 inactivated). In vivo mouse studies fully confirmed the specificity of this peptide strategy in inducing PCD in leukemic cells. Therefore, this invention is related to a soluble peptide comprising the amino acids sequence: KRFYVVMWK (SEQ ID NO: 64) or a function-conservative variant thereof for use in the treatment of cancer.

However, and although WO 2013/182650 enabled to specifically identify peptide sequences for use in the treatment of cancer, the peptides described in WO 2013/182650 cannot be used for therapeutic purposes since their potency remain very slow and require high peptide concentration to trigger PCD (around 200 μM for the most potent peptide described in WO 2013/182650). So, there is still a need to identify more potent compounds which present CD47 ligation properties with high affinity and high potency in triggering PCD, specifically for diseases associated with defects in PCD such as cancers and immunological disorders including chronic inflammation.

The present invention answers this first need by the design of cyclic mimetics of the TSP-1 C-terminal binding domain with high affinity (in the nanomolar range) and potency in triggering PCD (in the microM range). Surprisingly, the Inventors have observed that these cyclic peptides are 100 to 1000 times more potent than those described in WO 2013/182650 (see FIGS. 6 and 7).

SUMMARY OF THE INVENTION

The Inventors have now prepared new cyclic peptides derived from the C-terminal domain of TSP-1 including the sequence involved in the beta-sheets No 7 or in beta-sheets No 7 and 8 or in the beta-sheets No 6 and 7 (beta-sheets numbering according to the EMBO Journal (2004) 23, 1223-1233).

Surprisingly, these cyclic peptides are able to induce apoptosis of cancer cell lines with high efficiency.

In contrast to known linear peptides targeting CD47, these cyclic peptides have high binding affinities (with Kd in the nanomolar range compared to affinities in the micromolar range for the best linear peptides described to date, PKT16, see part 3 of the examples) and are efficient at lower concentration to induce apoptosis (1 microM compared to 100 microM for the best linear derivatives, PKT16, see part 2 of the examples).

The present invention thus provides an isolated cyclic peptide derived from the C-terminal domain of TSP-1 or a biologically active derivative thereof; the present invention also relates to the use of said cyclic peptides as agonist of CD47 for treating diseases associated with defects in PCD such as cancer and immunological disorders.

BRIEF DESCRIPTION OF THE FIGURES

FIG. 5 and FIG. 6. Binding curve measured by MST. The measurement method is based on the directed movement of molecules along a temperature gradient, an effect termed "thermophoresis". A local temperature difference ΔT leads to a local change in molecule concentration (depletion or enrichment), quantified by the Soret coefficient $S_T$: $c_{hot}/c_{cold}=\exp(-S_T \Delta T)$. Jurkat or Mec-1 cell membrane preparations are labeled using the Nanotemper NT-647 labeling kit as described elsewhere.xliv The labeled preparation is eluted with PBS and stored at 4° C. A stock solution of each peptide is prepared in DMSO (5 mM) and then diluted with PBS. For the peptides evaluated by MST, we have kept the concentration of the NT.115-labeled membrane constant, while the concentration of the ligand (peptide) was varied. After a short incubation the samples were loaded into MST premium glass capillaries and the MST analysis was performed using the Monolith NT.115-pico. FIG. 5: MST curve observed for PKT16 [(D)Lys-(N-Me)Arg-Phe-Tyr-Val-Val-Nle-Trp-Lys-(D)Lys] (SEQ ID NO: 66) a linear peptide derived from the C-terminal binding domain of TSP-1. The Kd=1600 nM. FIG. 6A to 6H: MST curves observed for PKTD1, PKTD10, PKTD10-1, PKTD10-3, PKTD10-4, PKTD10-5, PKTD10-8 [see structures and sequences in Table I] cyclic peptide analogues of the C-terminal binding domain of TSP-1. The Kd (1.9 and 49 nM respectively). The Kd ratio between PKT16 and PKTD1 or PKTD10 for example highlights the fact that these cyclic analogues (i.e. PKTD1 or PKTD10) are much more efficient in CD47 ligation. Such affinities of the linear peptide analogues develop to date have never been reached.

FIG. 7A to 7F. Those Figures show results of the effects of several cyclic peptides of the invention (PKTD1, PKTD7, PKTD10, PKTD11, PKTD16, PKD10 and PKD10-FF) in comparison with a linear analog (PKT16) on the viability of tumor cells that were evaluated on 5 cell lines (MCF-7, human breast cancer cells; HCT-116, human colon cancer cells; BxPC3, human pancreas cancer cells; A549 and human lung cancer cells) by cytotoxic assay and by counting directly the number of cells. Noticeably, PKT16, the linear analogue is not efficient at 100 microM on these cancer cell lines whereas the cyclic analogues designed to mimic a hairpin involving the beta strands 6 and 7, or 7 and 8, of the C-terminal binding domain of TSP-1 (such as PKTD1, PKTD7, PKTD9, PKTD10, PKTD10-X-NMe, PKTD11, PKTD11-NMe, PKTD18, PKD8 and PKD10 for example among others) are efficient in inducing cell death on these cancer cell lines. Of importance, the simple cyclisation of the beta strand number 7 (4N1 binding epitope of TSP-1) is not sufficient to improve the peptide efficiency since the cyclisation of the 4N1 sequence (peptide PKC1) led to a cyclic analogue that has no potency in inducing cell death.

DETAILED DESCRIPTION OF THE INVENTION

Isolated Cyclic Peptides

Figure 1:
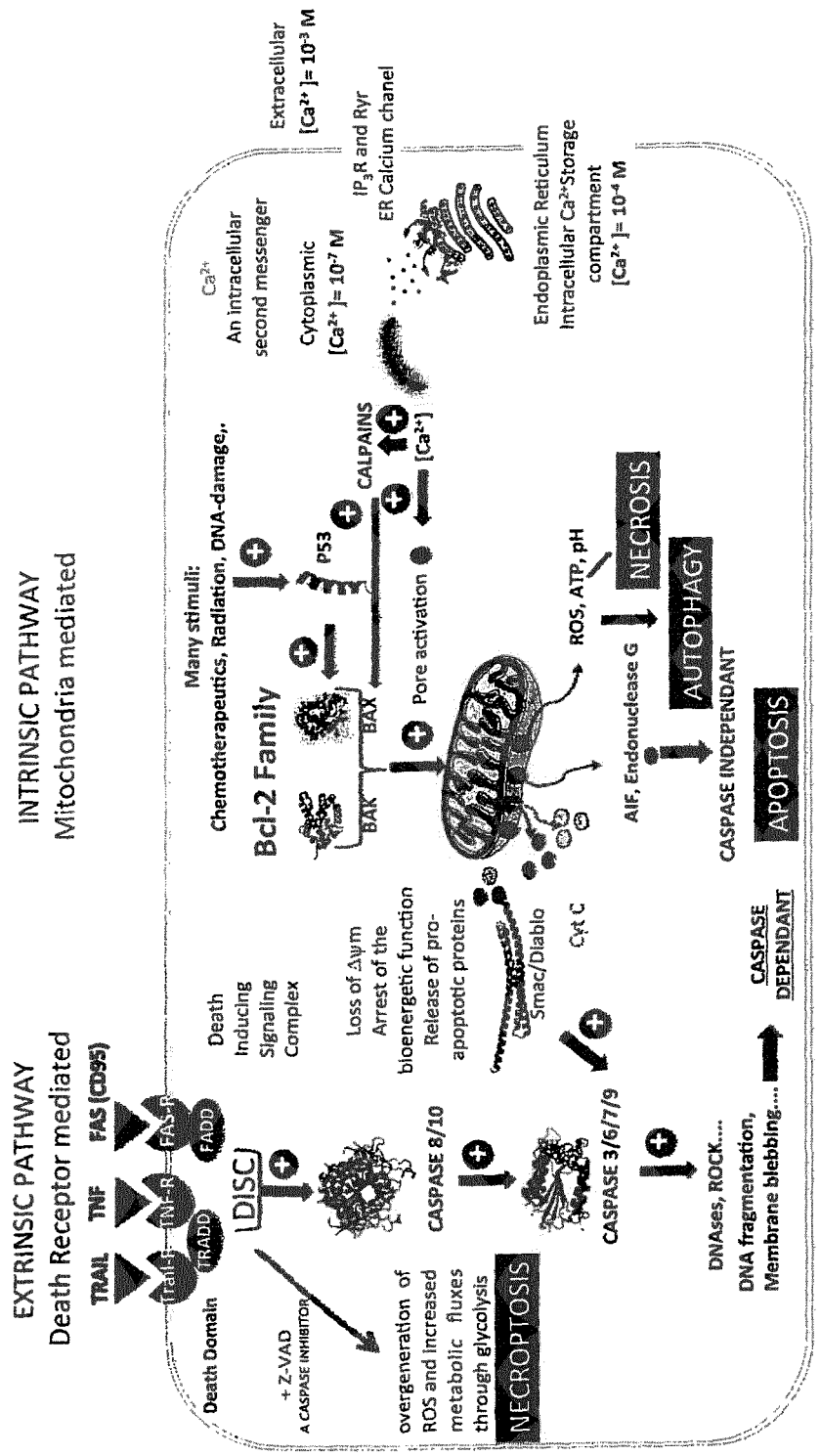
FIGS. 1 and 2. Two pathways closely connected leading to different types of PCD showing that PCD is a complex network and highly regulated process.
Figure 2:
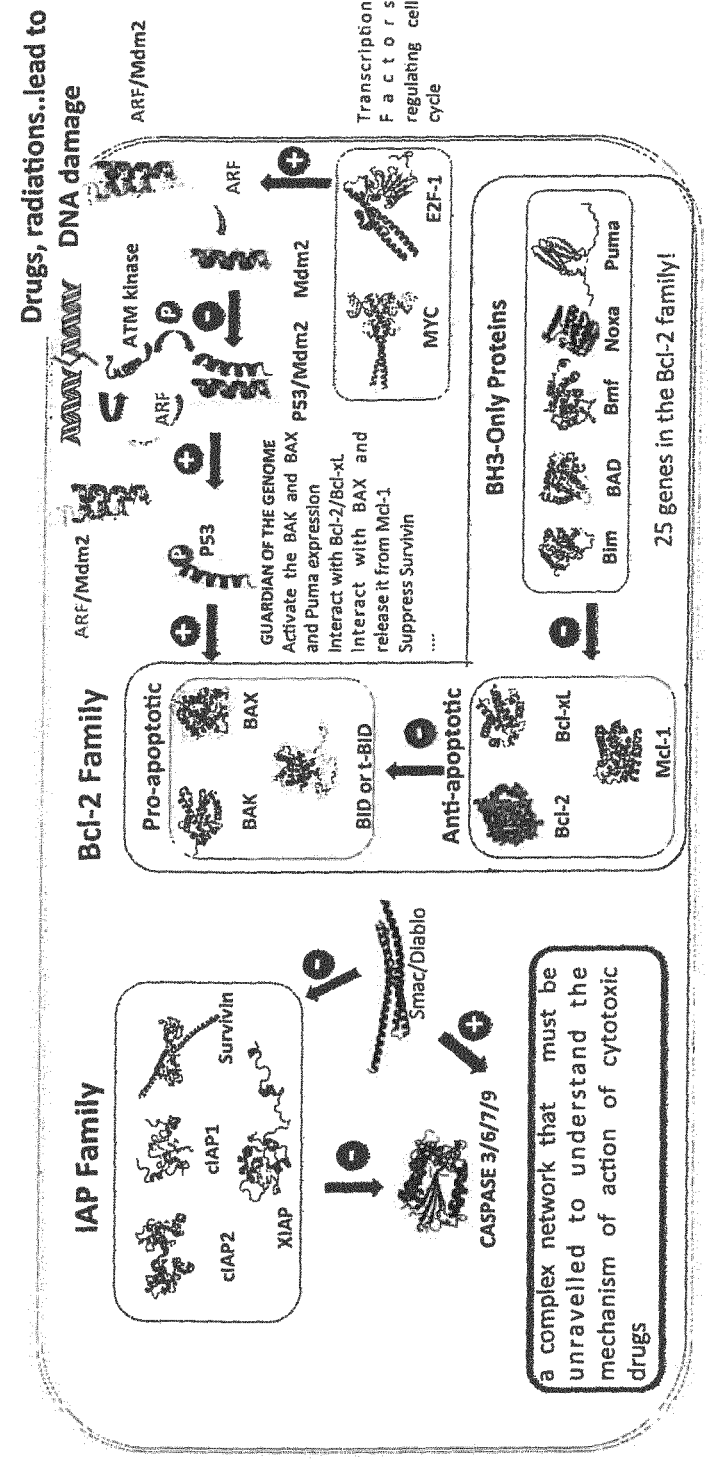
Figure 3A:
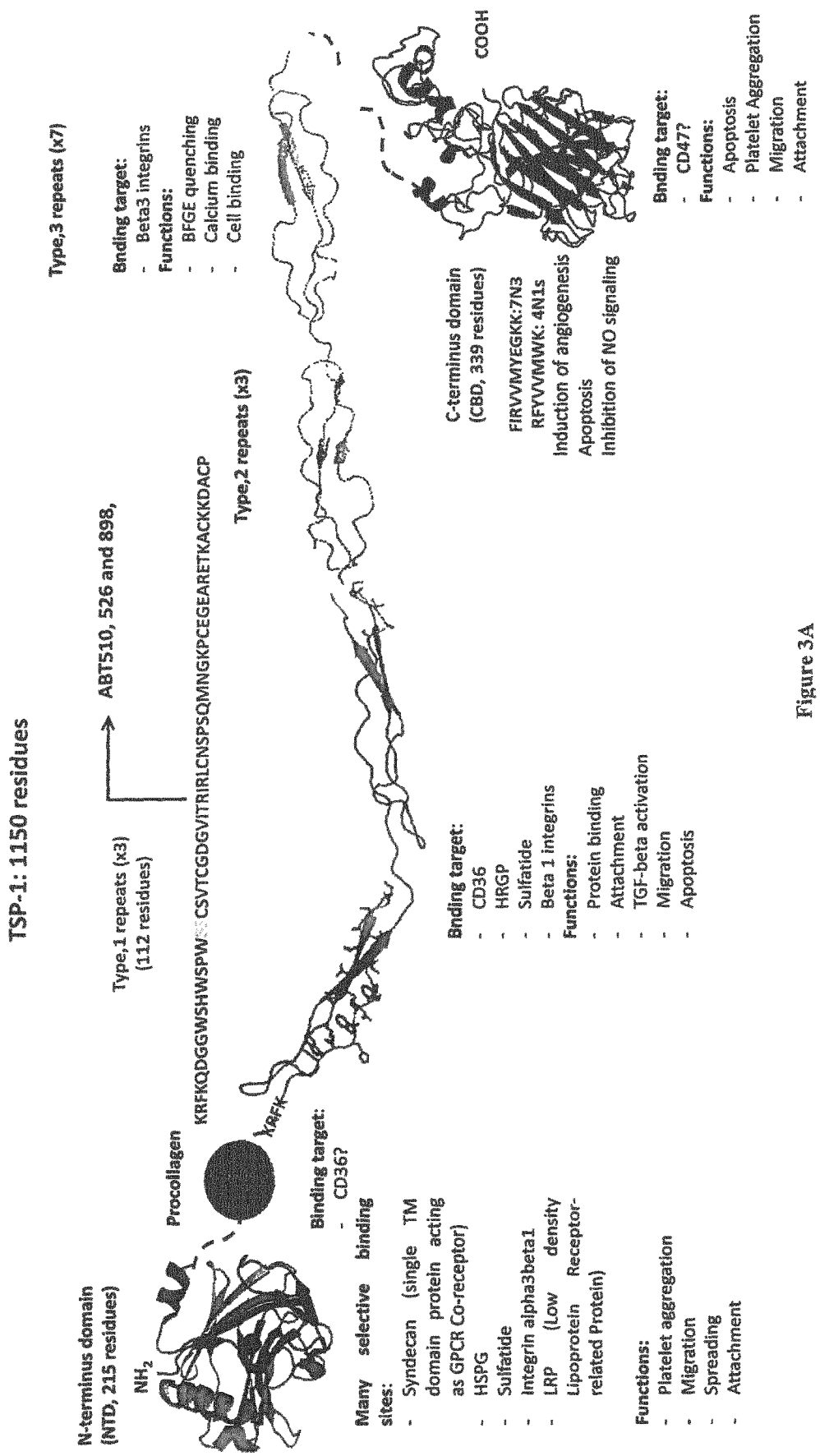
FIG. 3. A. TSP-1 is a multidomain protein, each domain involved in biological function: the heparin-binding domain (HBD), the von Willebrand C domain (vWCD), three type 1 properdin repeats, three type 2 EGFlike repeats, seven type 3 calcium-binding repeats and the C-terminal CBD. Some of the domains interact with extracellular matrix components or membrane receptors (arrows). Key amino acid sequences responsible for TSP-1 ligation to integrins (RGD) and CD47 (RFYVVMWK) (SEQ ID NO: 3) are indicated. Additional illustrated sequences are set forth as SEQ ID NOS: 65 and 62. 3B. This figure shows the CD47 and 4N1 interaction. The open conformation of the TSP-1 C-terminal domain (MRMS=2 Å) was used for protein-protein docking experiments against a homology model of the extracellular part of the CD47receptor. Two putative TSP-1:CD47 interaction regions [(1) and (2), respectively] were proposed by molecular modeling (see Floquet et al, 2008).[xlii]
Figure 3B:
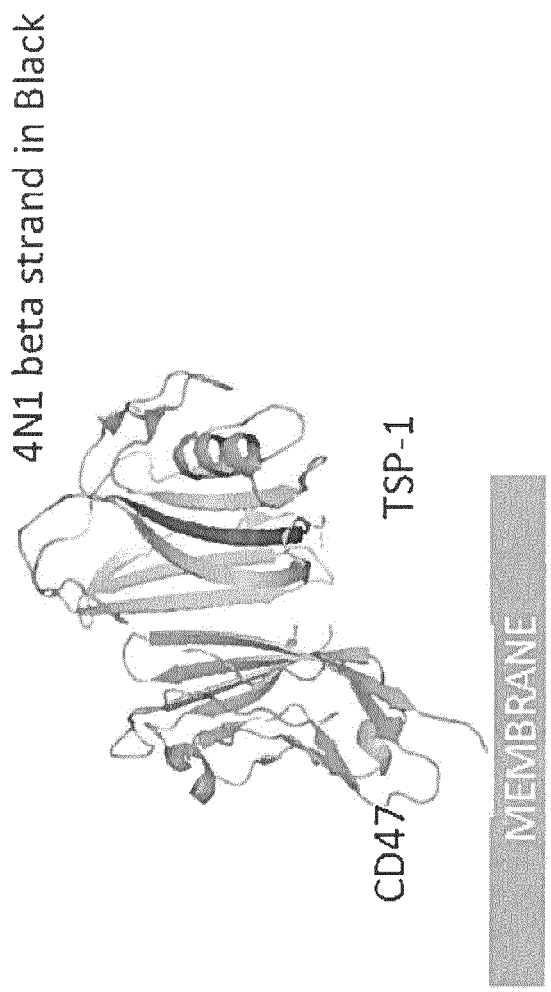
Figure 4:
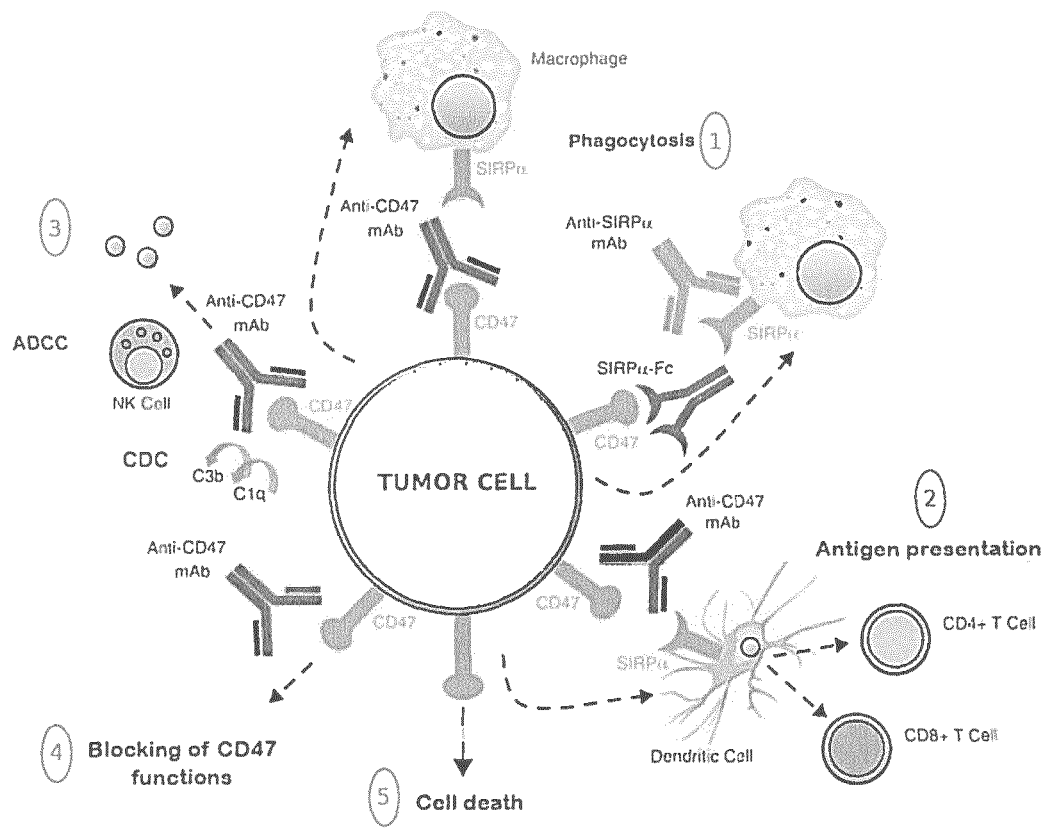
FIG. 4. CD47 is used as a target to eliminate cancer cells. Therapeutic targeting of CD47 using monoclonal antibodies (mAb) can induce the elimination of cancer cells through multiple mechanisms. 1) Through phagocytic uptake of tumor cells by macrophages: by inhibiting the CD47-SIRPα interaction with a blocking anti-CD47 mAb, a blocking anti-SIRPα mAb, or a recombinant SIRPα protein (shown as a bivalent Fc-fusion protein). 2) Anti-CD47 antibodies can stimulate an anti-tumor adaptive immune response leading to the phagocytic uptake of tumor cells by DCs and subsequent antigen presentation to CD4 and CD8 T cells. 3) By NK cell-mediated ADCC and CDC induction and tumor cell elimination: an anti-CD47 antibody can eliminate tumor cells through antibody Fc-dependent mechanisms. 4) Function blocking of CD47 may also promote tumor reduction by blocking several of its actions in tumor cells. 5) Finally, CD47 stimulation can induce direct cell death induction. Modified from[xliii].

The present invention relates to an isolated cyclic peptide of general formula (I):

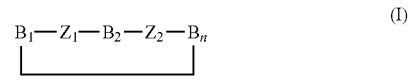

or a pharmacologically acceptable salt or a biologically active derivative thereof, wherein:

$B_1$ is nothing or a peptidic sequence comprising between 6 and 10 amino acids derived from the beta-strand No 6 of TSP-1 of sequence YAGVF (SEQ ID NO: 1);

$Z_1$ is nothing or an heterochiral sequence D-Pro-L-Pro (also designated p-P, p being a D-proline and P a L-proline) or any sequence of two amino acids or analogs of amino acid able to mimic said heterochiral sequence or mimic a beta turn, example of amino acids or analogs of amino acid of said sequence are nipecotic acid, isonipecotic acid, piperidine carboxylic acid, silaproline, thioproline and any other substituted derivative thereof (fluoro, methyl, bromo etc), pseudo proline, substituted proline, N-methyl amino acids, cyclopropyl amino acids (see Karoyan et al. Target in heterocyclic system, 2004 and Karoyan et al. ChemBioChem (2011), 12(7), 1039-1042 and Larregola et al. Journal of Peptide Science (2011), 17(9), 632-643) or biaryl amino acids templates; with the proviso that $Z_1$ is nothing if $B_1$ is nothing; in a preferred embodiment, $Z_1$ is D-Pro-L-Pro;

$B_2$ represents the peptidic sequence $X_1$-$X_2$-$X_3$-$X_4$-$X_5$-$X_6$-$X_7$-$X_8$-$X_9$-$X_{10}$ (SEQ ID NO: 2) is derived from the beta-strand No 7 of TSP-1 (of sequence RFYVVMWK, SEQ ID NO: 3) wherein:

$X_1$ refers to nothing or serine or any amino acid with similar properties such as glycine or alanine or threonine;

$X_2$ refers to nothing or arginine or any amino acid with similar properties such as homoarginine, lysine, ornithine, phenylalanine, naphtylalanine, N-methyl arginine or homophenylalanine or any other ring substituted analogues in ortho, meta or para position; for example for arginine, derivatives include any other side chain involving a guanido function and/or one or more than one amine function;

$X_3$ refers to phenylalanine or any amino acid with similar properties including naphtylalanine, homophenylalanine or any other ring substituted analogues in ortho, meta or para position such as para-fluoro-phenylalanine, para-amino-phenylalanine or para-nitro-phenylalanine; tyrosine or any amino acid with aromatic side chains;

$X_4$ refers to tyrosine or any amino acid with aromatic side chains, phenylalanine or any amino acid with similar properties including naphtylalanine, homophenylalanine or any other ring substituted analogues in ortho, meta or para position such as para-fluoro-phenylalanine, para-amino-phenylalanine or para-nitro-phenylalanine;

$X_5$ refers to valine or any amino acid with similar properties including leucine, isoleucine, terleucine, methionine;

$X_6$ refers to valine or any amino acid with similar properties including leucine, isoleucine, terleucine, methionine;

$X_7$ refers to methionine or lysine or any amino acid with similar properties including valine, methionine, norleucine, leucine or isoleucine or terleucine;

$X_8$ refers to tryptophan, tyrosine, phenylalanine, naphthyl-alanine, para-fluoro-phenylalanine, para-amino-phenylalanine, para-nitro-phenylalanine, D-prolino-tryptophane or D-prolino-homotryptophane;

$X_9$ refers to nothing or lysine or any amino acid with similar properties including arginine, homoarginine, ornithine, phenylalanine, naphtylalanine, N-methyl arginine or homophenylalanine or any other ring substituted analogues in ortho, meta or para position or histidine;

$X_{10}$ refers to nothing or glutamine or alanine or any amino acid with similar properties including asparagine;

$Z_2$ is nothing or an heterochiral sequence D-Pro-L-Pro (also designated p-P) or any sequence of two amino acids or analogs of amino acid able to mimic said heterochiral sequence or mimic a beta turn, example of amino acids or analogs of amino acid of said sequence are nipecotic acid, isonipecotic acid, piperidine carboxylic acid, silaproline, thioproline and any other substituted derivative thereof (fluoro, methyl, bromo etc), pseudo proline, substituted proline, N-methyl amino acids, cyclopropyl amino acids (Karoyan et al. Target in heterocyclic system, 2004 and Karoyan et al. ChemBioChem (2011), 12(7), 1039-1042 and Larregola et al. Journal of Peptide Science (2011), 17(9), 632-643) or biaryl amino acids templates; with the proviso that $Z_2$ is nothing if $B_3$ is nothing; in a preferred embodiment, $Z_2$ is D-Pro-L-Pro;

$B_n$ represents $B_2$ or $B_3$;

$B_3$ is nothing or a peptidic sequence comprising between 6 and 10 amino acids derived from the beta-strand No 8 of TSP-1 (of sequence GLSVKVVNS, SEQ ID NO: 4); with the proviso that if $B_1$ is a peptidic sequence comprising between 6 and 10 amino acids residues derived from the beta-strand No 6 of TSP-1 then $B_n$ is nothing and if $B_n$ is $B_2$ or $B_3$ (that is to say a peptidic sequence) then $B_1$ is nothing; and wherein said isolated cyclic peptide comprises between 8 and 26 amino acids, preferably between 14 and 22 amino acids; according to an other embodiment, isolated cyclic peptide comprises between 18 and 22 amino acids.

Except when explicitly mentioned, all amino acids are indifferently of the (D) or (L) configuration.

The present invention thus encompasses cyclic peptides of formula $B_1$-$Z_1$-$B_2$, $B_1$-$B_2$, $B_2$-$Z_2$-$B_3$, $B_2$-$B_3$, $B_2$-$B_2$ (each $B_2$ being identical or different), $B_2$-$Z_2$-$B_2$ (each $B_2$ being identical or different) and $B_2$.

In an embodiment, $B_1$ comprises the following sequence: YAGFVFG (SEQ ID NO: 5).

In another embodiment, $B_1$ comprises the following sequence: -$X_{11}$-Y-A-G-F-V-F-G-$X_{12}$-$X_{13}$- (SEQ ID NO: 6) wherein:

$X_{11}$ is nothing or aspartic acid or any amino acid with similar properties including glutamic acid;

$X_{12}$ is nothing or tyrosine or any amino acid with aromatic side chains and $X_{13}$ is nothing or serine or any amino acid with similar properties including glycine.

In an embodiment, $B_3$ comprises the following sequence: -$X_{19}$-$X_{14}$-$X_{15}$-$X_{20}$-$X_{21}$-$X_{16}$-$X_{22}$-$X_{23}$-$X_{17}$-$X_{18}$- (SEQ ID NO: 36); preferably, $B_3$ comprises the following sequence -$X_{19}$-$X_{14}$-$X_{15}$-S-V-$X_{16}$-V-V-$X_{17}$-$X_{18}$- wherein:

$X_{14}$ is nothing or glycine or alanine or any amino acid with similar properties including serine;

$X_{15}$ is isoleucine or leucine or alanine or any amino acid with similar properties including terleucine, valine, methionine;

$X_{16}$ is lysine or alanine or any amino acid with similar properties including arginine, homoarginine, lysine, ornithine, phenylalanine, naphtylalanine, N-methyl arginine or homophenylalanine or any other ring substituted analogues (ortho, meta, para), histidine, or methionine or any amino acid with similar properties including valine, leucine, isoleucine, terleucine;

$X_{17}$ is nothing or asparagine or alanine or any amino acid with similar properties including glutamine or lysine or any amino acid with similar properties including arginine, homoarginine, lysine, ornithine, phenylalanine, naphtylalanine, N-methyl arginine or homophenylalanine or any other ring substituted analogues (ortho, meta, para), histidine;

$X_{18}$ is nothing, serine or glycine or any amino acid with similar properties;

$X_{19}$ is nothing or serine or alanine or any amino acid with similar properties;

$X_{20}$ is serine or alanine or any amino acid with similar properties including leucine, isoleucine, terleucine;

$X_{21}$ is valine or alanine or any amino acid with similar properties including leucine, isoleucine, terleucine;

$X_{22}$ is valine or alanine or any amino acid with similar properties including leucine, isoleucine, terleucine; and $X_{23}$ is valine or alanine or any amino acid with similar properties including leucine, isoleucine, terleucine.

The isolated cyclic peptide of general formula (I) of the invention yet comprises at least parts of the beta-sheet No 7, of the beta-sheets No 7 and 8 or at least parts of the beta-sheets No 6 and 7 of the C-terminal domain of the TSP-1 but cannot be the entire sequence of the C-terminal domain of the TSP-1 (as described by Kosfeld M D, Frazier W A (1993) Identification of a new cell adhesion motif in two homologous peptides from the COOH-terminal cell binding domain of human thrombospondin. J Biol Chem 268: 8806-8814), because this domain has not the same biologic activity as cyclic peptides of the invention.

According to a specific embodiment, the present invention relates to an isolated cyclic peptide of general formula (Ia):

(Ia)

or a pharmacologically acceptable salt or a biologically active derivative thereof, wherein:

$Z_1$ is nothing or an heterochiral sequence D-Pro-L-Pro (also designated p-P, p being a D-proline and P a L-proline) or any sequence of two amino acids or analogs of amino acid able to mimic said heterochiral sequence or mimic a beta turn, example of amino acids or analogs of amino acid of said sequence are nipecotic acid, isonipecotic acid, piperidine carboxylic acid, silaproline, thioproline and any other substituted derivative thereof (fluoro, methyl, bromo etc), pseudo proline, substituted proline, N-methyl amino acids, cyclopropyl amino acids (see Karoyan et al. Target in heterocyclic system, 2004 and Karoyan et al. ChemBioChem (2011), 12(7), 1039-1042 and Larregola et al.

Journal of Peptide Science (2011), 17(9), 632-643) or biaryl amino acids templates; in a preferred embodiment, $Z_1$ is D-Pro-L-Pro;

$B_2$ represents the peptidic sequence $X_1$-$X_2$-$X_3$-$X_4$-$X_5$-$X_6$-$X_7$-$X_8$-$X_9$-$X_{10}$ (SEQ ID NO: 2) derived from the beta-strand No 7 of TSP-1 (of sequence RFYVVMWK, SEQ ID NO: 3) and comprises between 6 and 10 amino acids, wherein:

$X_1$ refers to nothing or serine or any amino acid with similar properties such as glycine or alanine or threonine;

$X_2$ refers to nothing or arginine or any amino acid with similar properties such as homoarginine, lysine, ornithine, phenylalanine, naphtylalanine, N-methyl arginine (RNMe) or homophenylalanine or any other ring substituted analogues in ortho, meta or para position; for example for arginine, derivatives include any other side chain involving a guanido function and/or one or more than one amine function;

$X_3$ refers to phenylalanine or any amino acid with similar properties including naphtylalanine, homophenylalanine or any other ring substituted analogues in ortho, meta or para position such as para-fluoro-phenylalanine, para-amino-phenylalanine or para-nitro-phenylalanine; tyrosine or any amino acid with aromatic side chains;

$X_4$ refers to tyrosine or any amino acid with aromatic side chains, phenylalanine or any amino acid with similar properties including naphtylalanine, homophenylalanine or any other ring substituted analogues in ortho, meta or para position such as para-fluoro-phenylalanine, para-amino-phenylalanine or para-nitro-phenylalanine;

$X_5$ refers to valine or any amino acid with similar properties including leucine, isoleucine, terleucine, methionine;

$X_6$ refers to valine or any amino acid with similar properties including leucine, isoleucine, terleucine, methionine;

$X_7$ refers to methionine or lysine or any amino acid with similar properties including valine, methionine, norleucine, leucine or isoleucine or terleucine;

$X_8$ refers to tryptophan, tyrosine, phenylalanine, naphthyl-alanine, para-fluoro-phenylalanine, para-aminophenylalanine, para-nitro-phenylalanine, D-prolinotryptophane or D-prolino-homotryptophane;

$X_9$ refers to nothing or lysine or any amino acid with similar properties including arginine, homoarginine, ornithine, phenylalanine, naphtylalanine, N-methyl arginine or homophenylalanine or any other ring substituted analogues in ortho, meta or para position or histidine;

$X_{10}$ refers to nothing or glutamine or any amino acid with similar properties including asparagine; $X_{10}$ may also refers to alanine;

preferably, if $X_2$ is nothing then $X_1$ is nothing and/or if $X_9$ is nothing then $X_{10}$ is nothing; preferably, $B_2$ comprises at least the 6 amino acids -$X_3$-$X_4$-$X_5$-$X_6$-$X_7$-$X_8$-; more preferably, $B_2$ comprises at least the peptidic fragment -F-Y-V-V-M-W- (SEQ ID NO: 37);

$Z_2$ is nothing or an heterochiral sequence D-Pro-L-Pro (also designated p-P, p being a D-proline and P a L-proline) or any sequence of two amino acids or analogs of amino acid able to mimic said heterochiral sequence or mimic a beta turn, example of amino acids or analogs of amino acid of said sequence are nipecotic acid, isonipecotic acid, piperidine carboxylic acid, silaproline, thioproline and any other substituted derivative thereof (fluoro, methyl, bromo etc), pseudo proline, substituted proline, N-methyl amino acids, cyclopropyl amino acids (see Karoyan et al. Target in heterocyclic system, 2004 and Karoyan et al. ChemBioChem (2011), 12(7), 1039-1042 and Larregola et al. Journal of Peptide Science (2011), 17(9), 632-643) or biaryl amino acids templates; in a preferred embodiment, $Z_1$ is D-Pro-L-Pro;

$B_n$ represents $B_2$ or $B_3$;

$B_3$ is a peptidic sequence comprising between 6 and 10 amino acids derived from the beta-strand No 8 of TSP-1 (of sequence GLSVKVVNS, SEQ ID NO: 4); $B_3$ comprises the following sequence: -$X_{19}$-$X_{14}$-$X_{15}$-$X_{20}$-$X_{21}$-$X_{16}$-$X_{22}$-$X_{23}$-$X_{17}$-$X_{18}$- (SEQ ID NO: 36); preferably, $B_3$ comprises the following sequence: -$X_{19}$-$X_{14}$-$X_{15}$-S-V-$X_{16}$-V-V-$X_{17}$-$X_{18}$- wherein:

$X_{14}$ is nothing or glycine or alanine or any amino acid with similar properties including serine;

$X_{15}$ is isoleucine or leucine or alanine or any amino acid with similar properties including terleucine, valine, methionine;

$X_{16}$ is lysine or alanine or any amino acid with similar properties including arginine, homoarginine, homolysine, ornithine, phenylalanine, naphtylalanine, N-methyl arginine (RNMe) or homophenylalanine or any other ring substituted analogues (ortho, meta, para), histidine, or methionine or any amino acid with similar properties including valine, leucine, isoleucine, terleucine;

$X_{17}$ is nothing, asparagine or alanine or any amino acid with similar properties including glutamine or lysine or any amino acid with similar properties including arginine, homoarginine, homolysine, ornithine, phenylalanine, naphtylalanine, N-methyl arginine (RNMe) or homophenylalanine or any other ring substituted analogues (ortho, meta, para), histidine;

$X_{18}$ is nothing, serine or glycine or any amino acid with similar properties;

$X_{19}$ is nothing, serine or alanine or any amino acid with similar properties;

$X_{20}$ is serine or alanine or any amino acid with similar properties including leucine, isoleucine, terleucine;

$X_{21}$ is valine or alanine or any amino acid with similar properties including leucine, isoleucine, terleucine;

$X_{22}$ is valine or alanine or any amino acid with similar properties including leucine, isoleucine, terleucine; and $X_{23}$ is valine or alanine or any amino acid with similar properties including leucine, isoleucine, terleucine;

preferably, if $X_{14}$ is nothing then $X_{19}$ is nothing and/or if $X_{17}$ is nothing then $X_{18}$ is nothing; preferably $B_3$ comprises at least the 6 amino acids -$X_{15}$-S-V-$X_{16}$-V-V-; more preferably, $B_3$ comprises at least the peptidic fragment -L-S-V-K-V-V (SEQ ID NO: 38);

wherein said isolated cyclic peptide comprises an even number of aminoacids (that is to say $B_2$ and $B_n$ have the same number of amino acids and both consist in a fragment of 6, 7, 8, 9 or 10 amino acids) and wherein said isolated cyclic peptide comprises between 8 and 26 amino acids, preferably between 12 and 22 amino acids; more preferably, isolated cyclic peptides of the invention consist in 12, 14, 16, 18, 20 or 22 amino acids.

The present invention thus encompasses cyclic peptides of formula $B_2$-$B_3$, $Z_1$-$B_2$-$B_3$, $B_2$-$Z_2$-$B_3$, $B_2$-$B_2$ (each $B_2$ being identical or different) and $B_2$-$Z_2$-$B_2$ (each $B_2$ being identical or different).

In a preferred embodiment, $B_2$ and $B_3$ are arranged so that $X_5$ of $B_2$ faces $X_{16}$ of $B_3$ and $X_8$ of $B_2$ faces $X_{15}$ of $B_3$ as illustrated below:

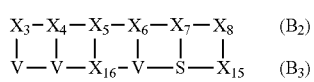

According to a particular embodiment, both $Z_1$ and $Z_2$ can be nothing; if $Z_1$ consists in two amino acids then $Z_2$ is nothing and if $Z_2$ consists in two amino acids then $Z_1$ is nothing.

Solutions of the cyclic peptides of the invention as free base or pharmacologically acceptable salts can be prepared.

The peptides thereof according to the invention can be formulated into a composition in a neutral or salt form.

Pharmaceutically acceptable salts include the acid addition salts (formed with the free amino groups of the peptide) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Examples of isolated cyclic peptide according to the present invention are as described in Table I:

TABLE I

| PEPTIDES | STRUCTURE/ AMINO: ACID SEQUENCE (linear representation) | FORMULA AND MW |
|---|---|---|
| PKPH12 (SEQ ID NO: 39) | 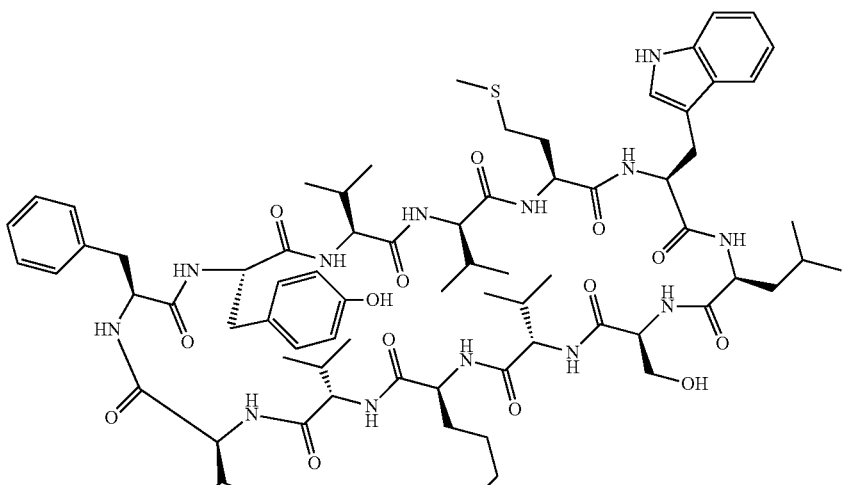 —F—Y—V—V—M—W—L—S—V—K—V—V— | |
| PKPH12P (SEQ ID NO: 40) | 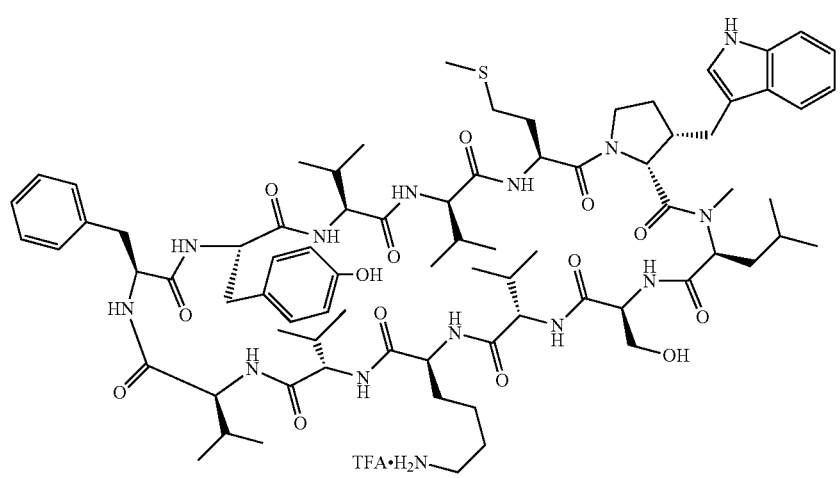 F—Y—V—V—M—P$_Z^3$hW—L—S—V—K—V—V— P$_Z^3$hW being D-prolino-homo-tryptophane (see Karoyan and Chassaing, Tetrahedron Letters, 1997, p84) | |

TABLE I-continued
| PEP-TIDES | STRUCTURE/ AMINO: ACID SEQUENCE (linear representation) | FORMULA AND MW |
|---|---|---|
| PKD8 (SEQ ID NO: 41) | 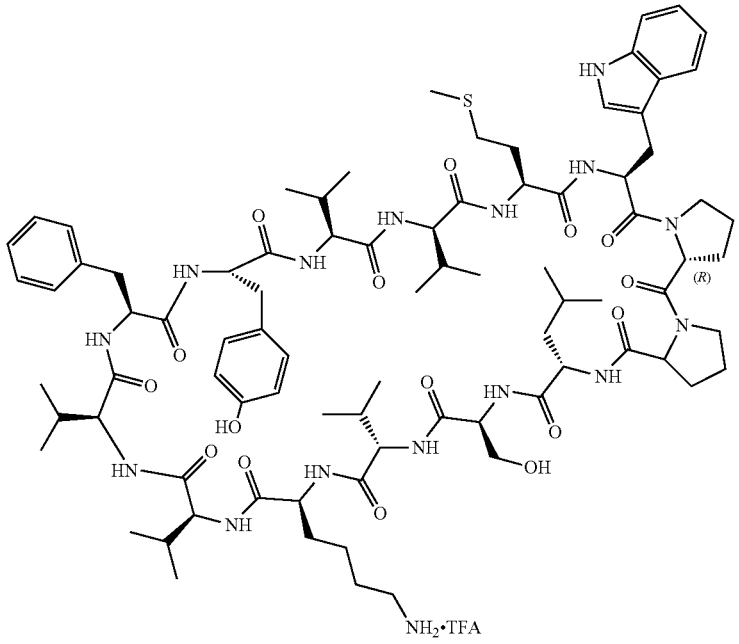 Chemical Formula: $C_{86}H_{124}F_3N_{16}O_{17}S$<br>Molecular Weight: 1743.09<br>—F—Y—V—V—M—W—p—P—L—S—V—K—V—V— | |
| PKD8FF (SEQ ID NO: 42) | 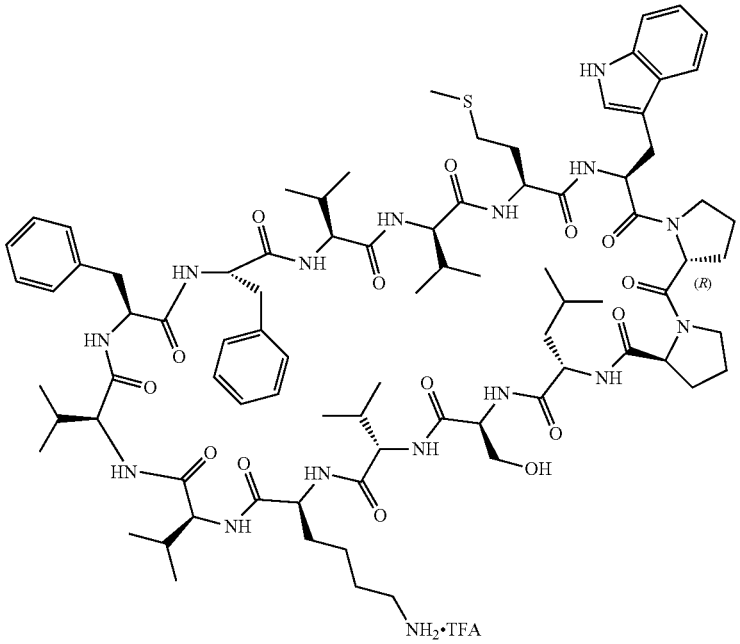 Chemical Formula: $C_{86}H_{124}F_3N_{16}O_{16}S$<br>Molecular Weight: 1727.09<br>—F—F—V—V—M—W—p—P—L—S—V—K—V—V— | |

TABLE I-continued
| PEP-TIDES | STRUCTURE/ AMINO: ACID SEQUENCE (linear representation) | FORMULA AND MW |
|---|---|---|
| PKD9 (SEQ ID NO: 43) | 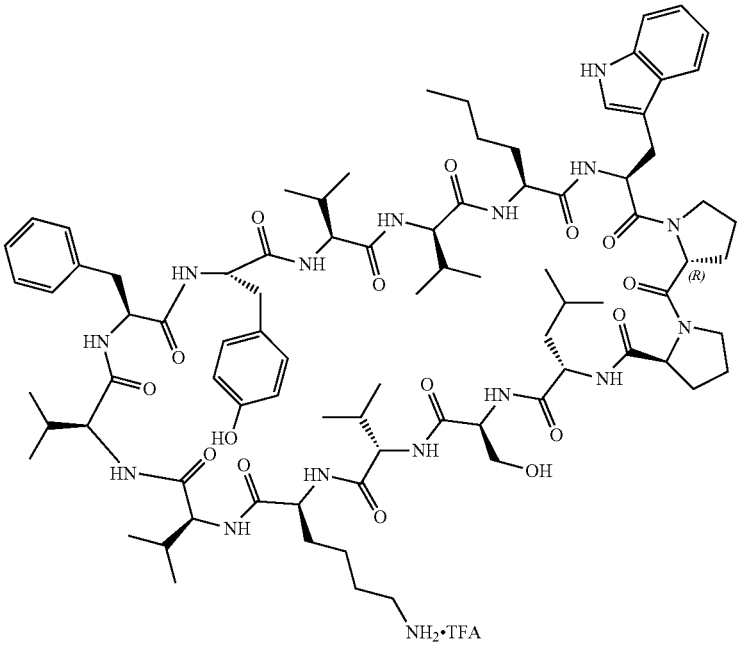 Chemical Formula: $C_{87}H_{126}F_3N_{16}O_{17}$<br>Molecular Weight: 1725.06<br>—F—Y—V—V—X—W—p—P—L—S—V—K—V—V—<br>X = NLe | |
| PKD10 (SEQ ID NO: 44) | 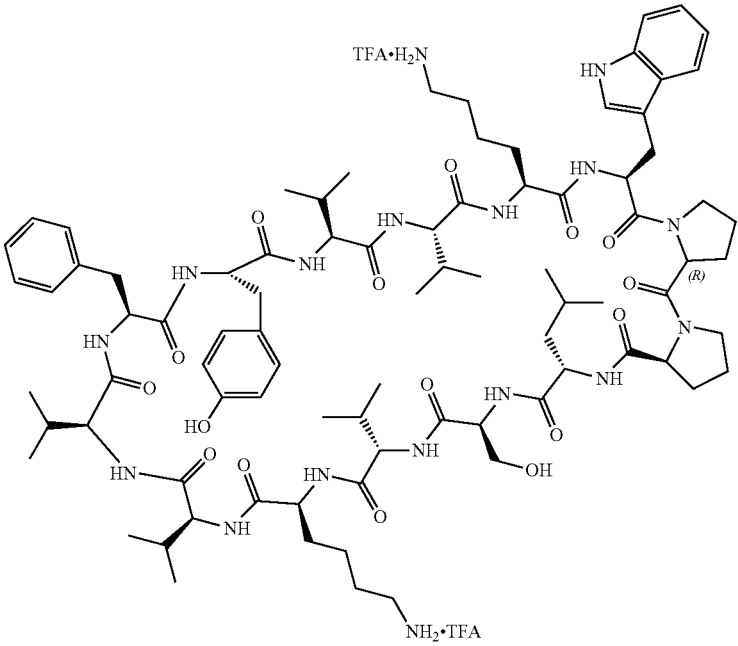 Chemical Formula: $C_{89}H_{127}F_6N_{17}O_{18}$<br>Molecular Weight: 1837.09<br>—F—Y—V—V—K—W—p—P—L—S—V—K—V—V— | |

TABLE I-continued
| PEP-TIDES | STRUCTURE/ AMINO: ACID SEQUENCE (linear representation) | FORMULA AND MW |
|---|---|---|
| PKD10FF (SEQ ID NO: 45) | 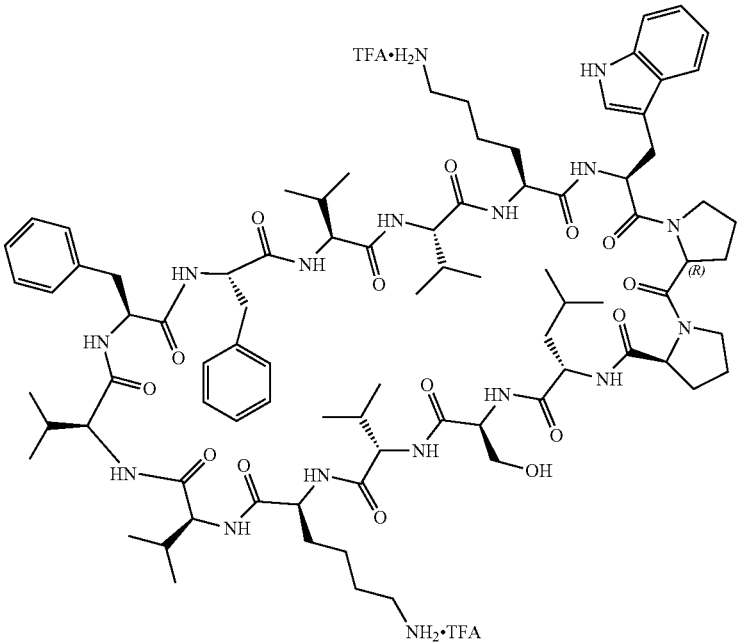 Chemical Formula: $C_{89}H_{127}F_6N_{17}O_{17}$<br>Molecular Weight: 1821.09<br>—F—F—V—V—K—W—p—P—L—S—V—K—V—V— | |
| PKTDi4 (SEQ ID NO: 46) | 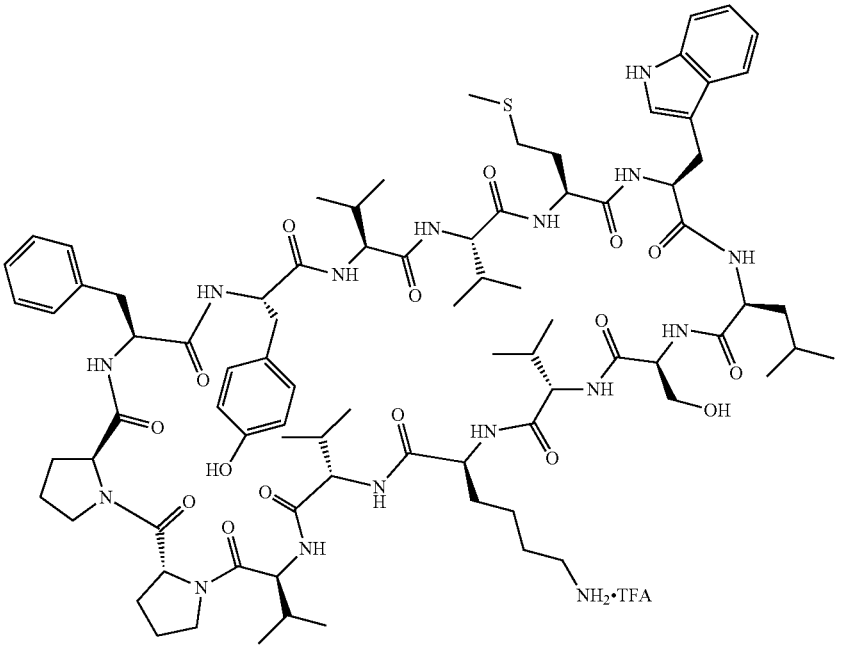 Chemical Formula: $C_{86}H_{124}F_3N_{16}O_{17}S$<br>Exact Mass: 1741.90<br>Molecular Weight: 1743.09<br>—p—P—F—Y—V—V—M—W—L—S—V—K—V—V— | |

TABLE I-continued
| PEPTIDES | STRUCTURE/ AMINO: ACID SEQUENCE (linear representation) | FORMULA AND MW |
|---|---|---|
PKD11
(SEQ ID NO: 47)
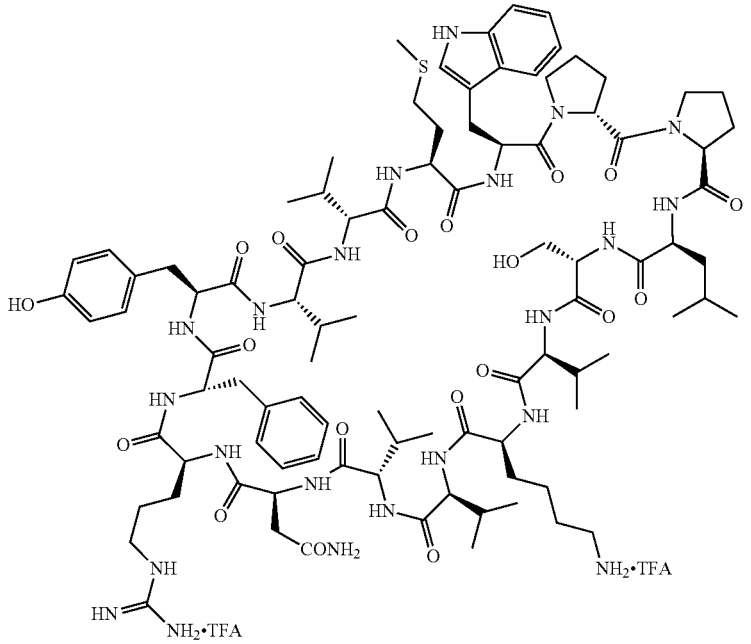
Chemical Formula: $C_{98}H_{142}F_6N_{22}O_{21}S$
Exact Mass: 2109.03
Molecular Weight: 2110.40
—R—F—Y—V—V—M—W—p—P—L—S—V—K—V—V—N—
PKD11RNMe
(SEQ ID NO: 48)
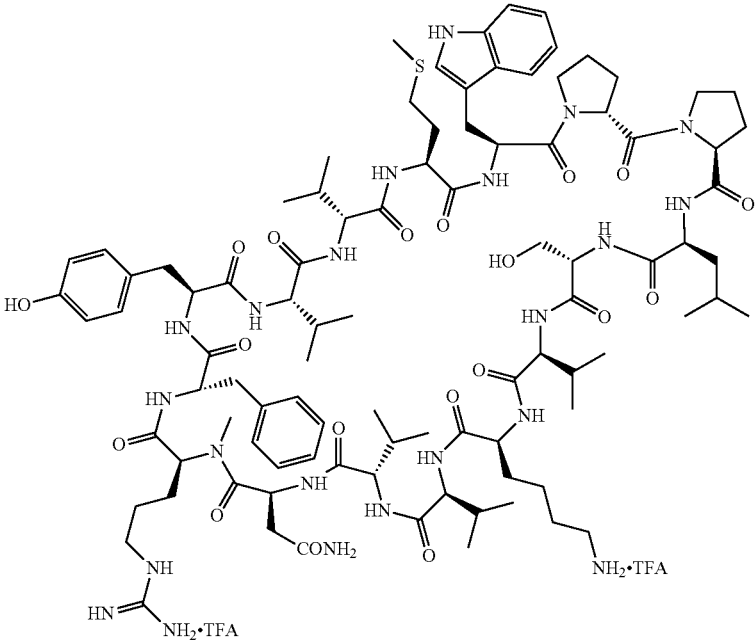
Chemical Formula: $C_{99}H_{144}F_6N_{22}O_{21}S$
Exact Mass: 2123.05
Molecular Weight: 2124.42
—R*—F—Y—V—V—M—W—p—P—L—S—V—K—V—V—N—
R* = NMethylarginine TABLE I-continued
| PEP-TIDES | STRUCTURE/ AMINO: ACID SEQUENCE (linear representation) | FORMULA AND MW |
|---|---|---|
| PKD12 (SEQ ID NO: 49) | 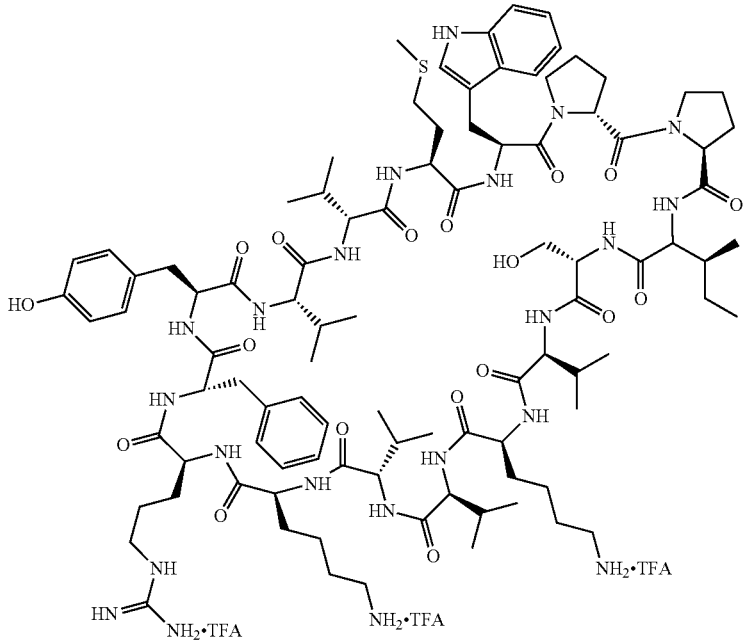<br>Chemical Formula: $C_{102}H_{148}F_9N_{22}O_{21}S$<br>Exact Mass: 2220.08<br>Molecular Weight: 2221.48<br>—R—F—Y—V—V—M—W—p—P—I—S—V—K—V—V—K— | |
| PKD12RNMe (SEQ ID NO: 50) | 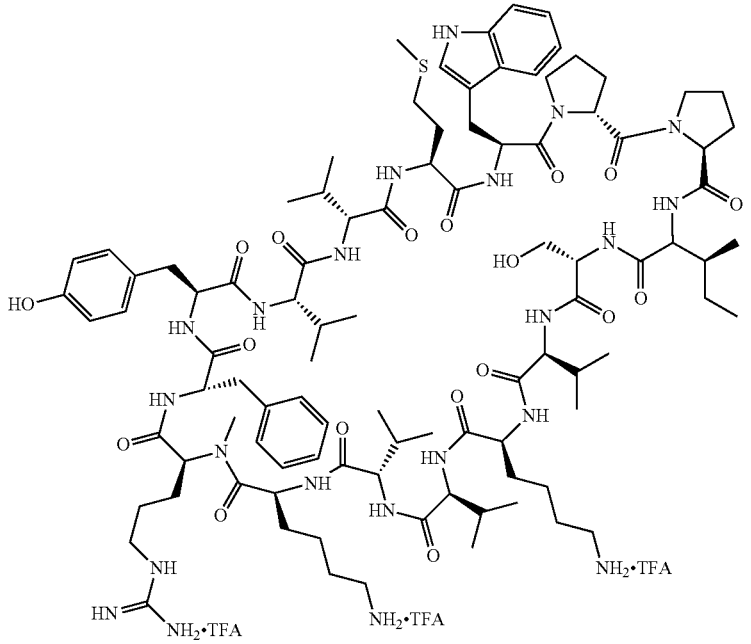<br>Chemical Formula: $C_{103}H_{150}F_9N_{22}O_{21}S$<br>Exact Mass: 2234.09<br>Molecular Weight: 2235.51<br>—R*—F—Y—V—V—M—W—p—P—I—S—V—K—V—V—K—<br>R* = NMethylarginine | |

TABLE I-continued
| PEPTIDES | STRUCTURE/ AMINO: ACID SEQUENCE (linear representation) | FORMULA AND MW |
|---|---|---|
| PKTDi3 (SEQ ID NO: 51) | 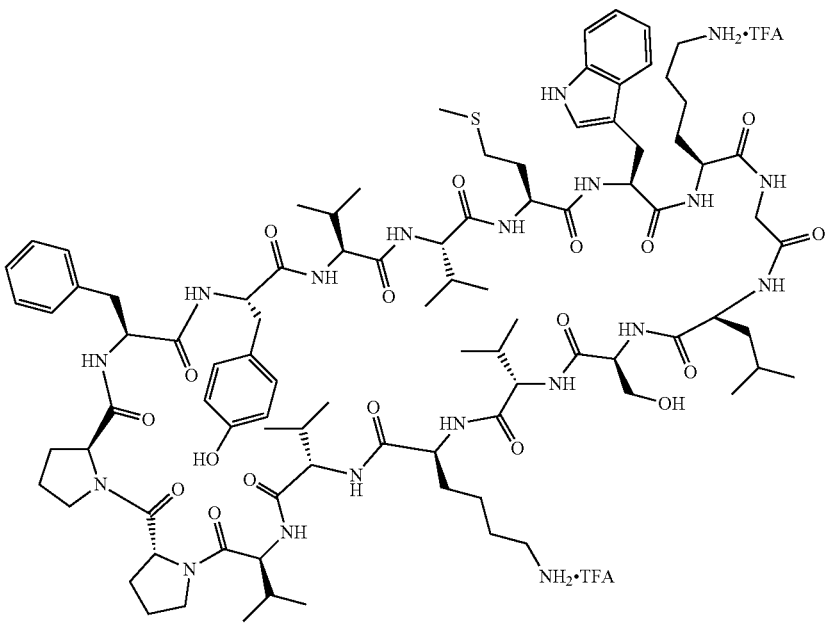 Chemical Formula: $C_{96}H_{139}F_6N_{19}O_{20}S$<br>Exact Mass: 2024.01<br>Molecular Weight: 2025.33<br>—p—P—F—Y—V—V—M—W—K—G—L—S—V—K—V—V— | |
| PKTDi5 (SEQ ID NO: 52) | 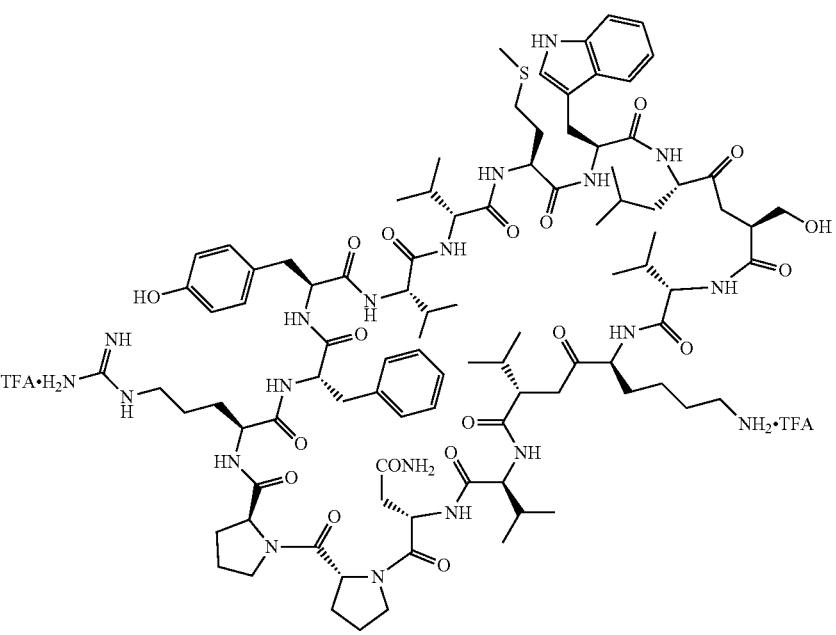 Chemical Formula: $C_{98}H_{142}F_6N_{22}O_{21}S$<br>Exact Mass: 2109.03<br>Molecular Weight: 2110.40<br>—p—P—R—F—Y—V—V—M—W—L—S—V—K—V—V—N— | |

TABLE I-continued
| PEP-TIDES | STRUCTURE/ AMINO: ACID SEQUENCE (linear representation) | FORMULA AND MW |
|---|---|---|
| PKTD7 (SEQ ID NO: 14) | 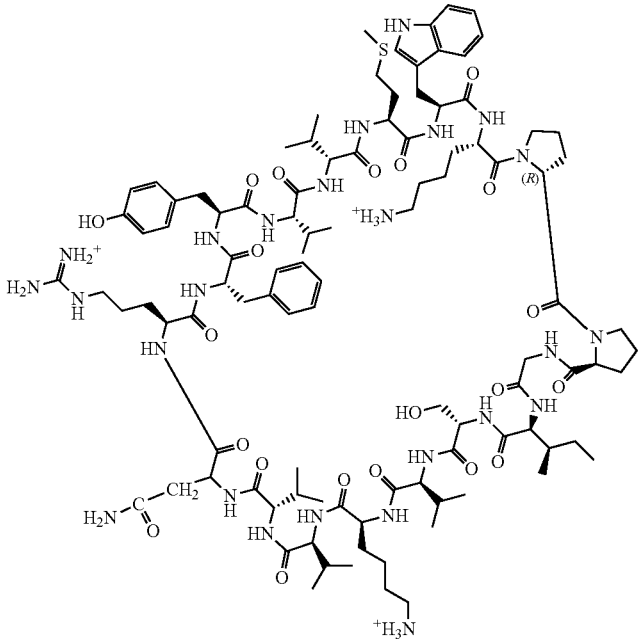<br>—R—F—Y—V—V—M—W—K—p—P—G—I—S—V—K—V—V—N— | Chemical Formula: $C_{102}H_{160}N_{25}O_{21}S_{3+}$ Molecular Weight: 2104.61 |
| PKTD14 (SEQ ID NO: 31) | 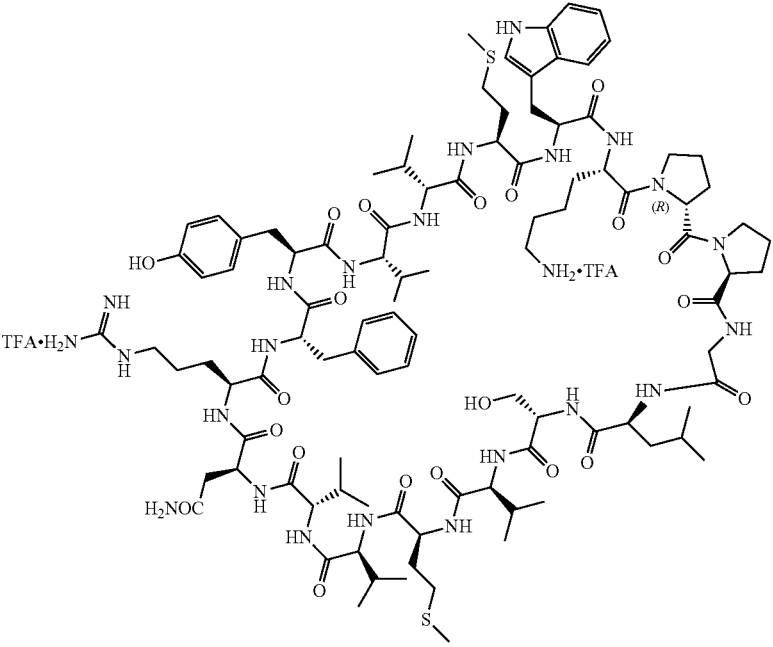<br>Chemical Formula: $C_{105}H_{154}F_6N_{24}O_{23}S_2$<br>Exact Mass: 2297.10<br>Molecular Weight: 2298.64<br>—R—F—Y—V—V—M—W—K—p—P—G—L—S—V—M—V—V—N— | |

TABLE I-continued
| PEP-TIDES | STRUCTURE/ AMINO: ACID SEQUENCE (linear representation) | FORMULA AND MW |
|---|---|---|
| PKTD15 (SEQ ID NO: 32) | 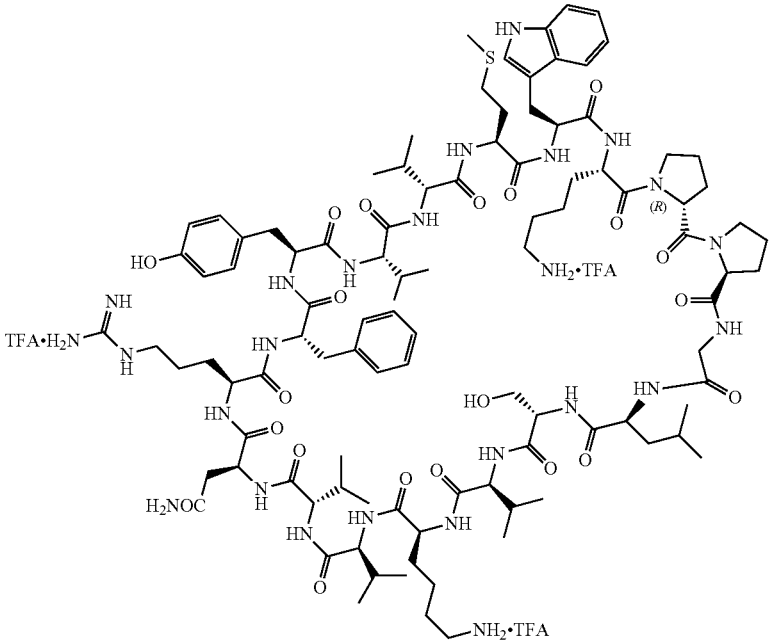Chemical Formula: $C_{108}H_{157}F_9N_{25}O_{24}S$<br>Exact Mass: 2391.14<br>Molecular Weight: 2392.64<br>—R—F—Y—V—V—M—W—K—p—P—G—L—S—V—K—V—V—N— | |
| PKTD17 (SEQ ID NO: 34) | 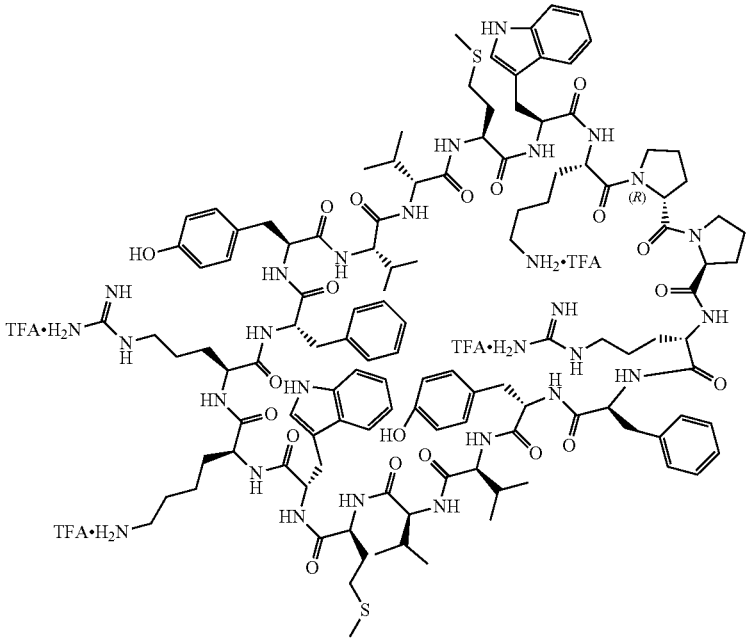Chemical Formula: $C_{130}H_{172}F_{12}N_{26}O_{24}S_2$<br>Exact Mass: 2801.23<br>Molecular Weight: 2803.08<br>—R—F—Y—V—V—M—W—K—p—P—R—F—Y—V—V—M—W—K— | |

TABLE I-continued
| PEP-TIDES | STRUCTURE/ AMINO: ACID SEQUENCE (linear representation) | FORMULA AND MW |
|---|---|---|
| PKTDi2 (SEQ ID NO: 53) | 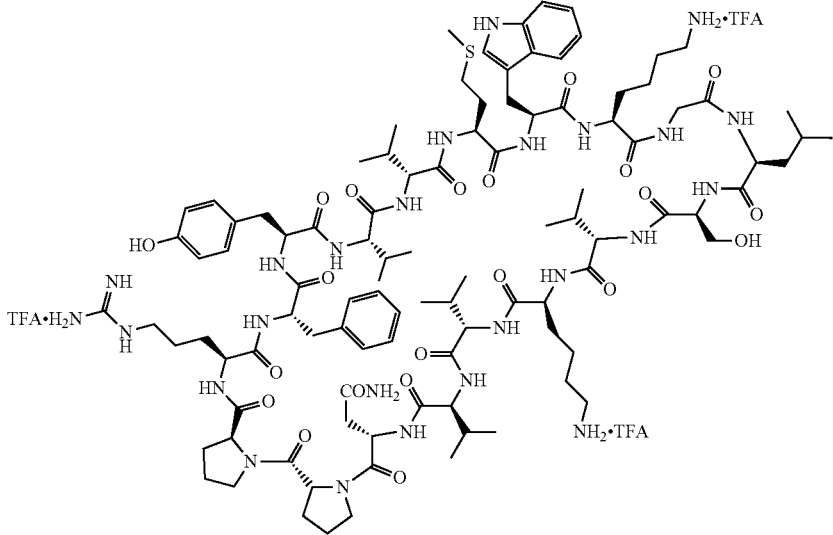 Chemical Formula: $C_{108}H_{157}F_9N_{25}O_{24}S$<br>Exact Mass: 2391.14<br>Molecular Weight: 2392.64<br>—p—P—R—F—Y—V—V—M—W—K—G—L—S—V—K—V—V—N— | |
| PKTD1 (SEQ ID NO: 9) | 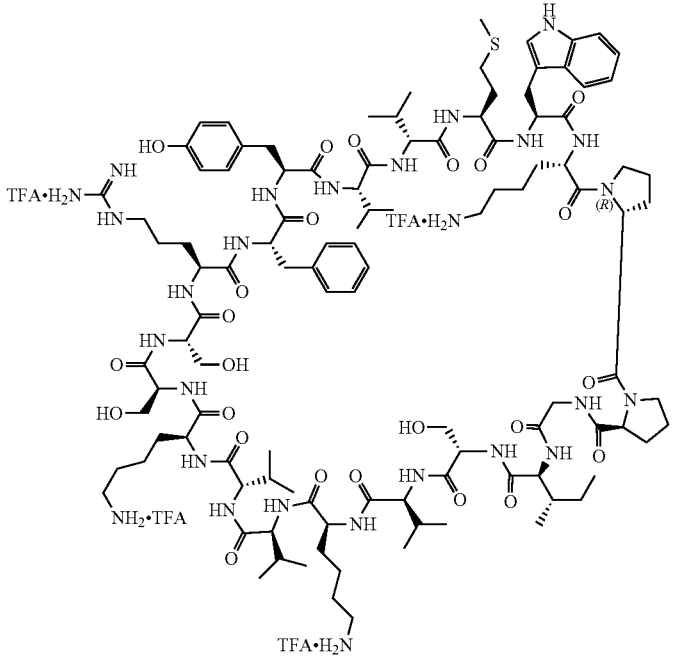 Chemical Formula: $C_{118}H_{173}F_{12}N_{27}O_{28}S$<br>Exact Mass: 2676.25<br>Molecular Weight: 2677.88<br>—S—R—F—Y—V—V—M—W—K—p—P—G—I—S—V—K—V—V—K—S— | |

TABLE I-continued
| PEP-TIDES | STRUCTURE/ AMINO: ACID SEQUENCE (linear representation) | FORMULA AND MW |
|---|---|---|
| PKTD3 (SEQ ID NO: 10) | 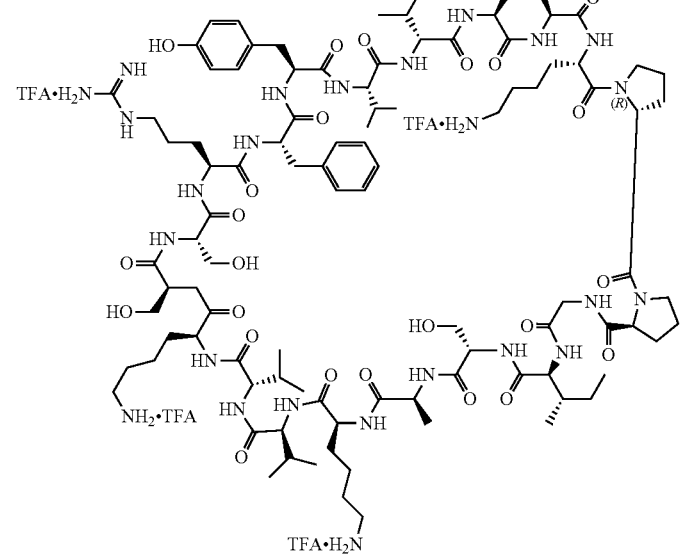<br>Chemical Formula: $C_{116}H_{169}F_{12}N_{27}O_{28}S$<br>Exact Mass: 2648.22<br>Molecular Weight: 2649.83<br>—S—R—F—Y—V—V—M—W—K—p—P—G—I—S—A—K—V—V—K—S— | |
| PKTD4 (SEQ ID NO: 11) | —D—Y—A—G—F—V—F—G—Y—p—P—R—F—Y—V—V—M—W—K—Q— | |
| PKTD5 (SEQ ID NO: 12) | —Y—A—G—F—V—F—G—Y—p—P—R—F—Y—V—V—M—W—K— | |
| PKTD6 (SEQ ID NO: 13) | 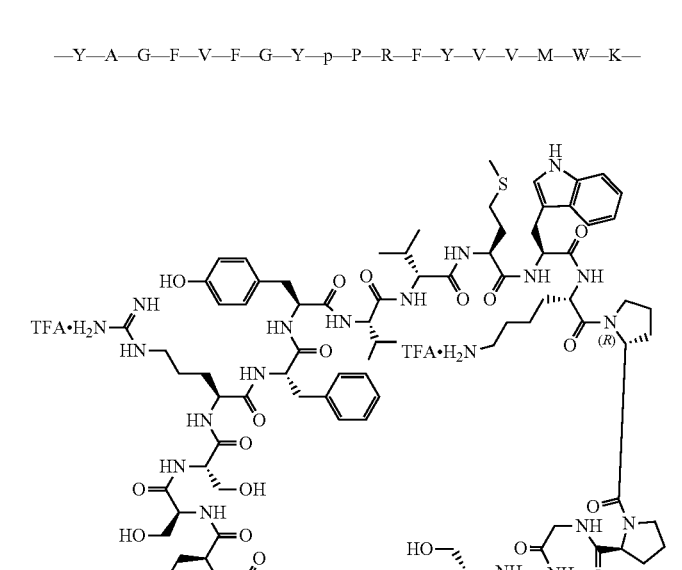 | |

TABLE I-continued
| PEP-TIDES | STRUCTURE/ AMINO: ACID SEQUENCE (linear representation) | FORMULA AND MW |
|---|---|---|
| | Chemical Formula: $C_{114}H_{167}F_9N_{27}O_{28}S$<br>Exact Mass: 2565.21<br>Molecular Weight: 2566.80<br>—S—R—F—Y—V—V—M—W—K—p—P—G—I—S—V—K—V—V—N—S— | |
| PKTD8 (SEQ ID NO: 15) | —D—Y—A—G—F—V—F—G—Y—Q—p—P—S—R—F—Y—V—V—M—W—K—Q— | |
| PKTD9 (SEQ ID NO: 16) | 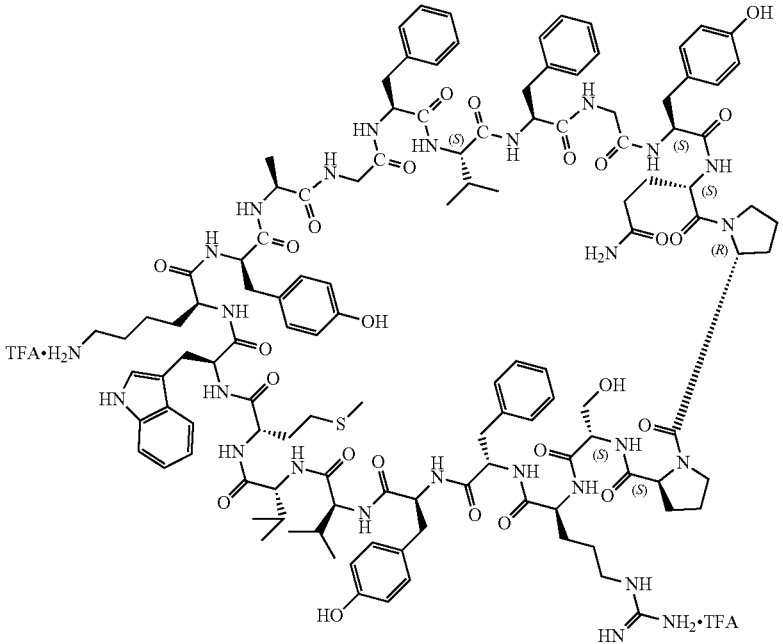<br>Chemical Formula: $C_{126}H_{162}F_6N_{26}O_{27}S$<br>Molecular Weight: 2618.89<br>—Y—A—G—F—V—F—G—Y—Q—p—P—S—R—F—Y—V—V—M—W—K— | |
| PKTD10 (SEQ ID NO: 17) | 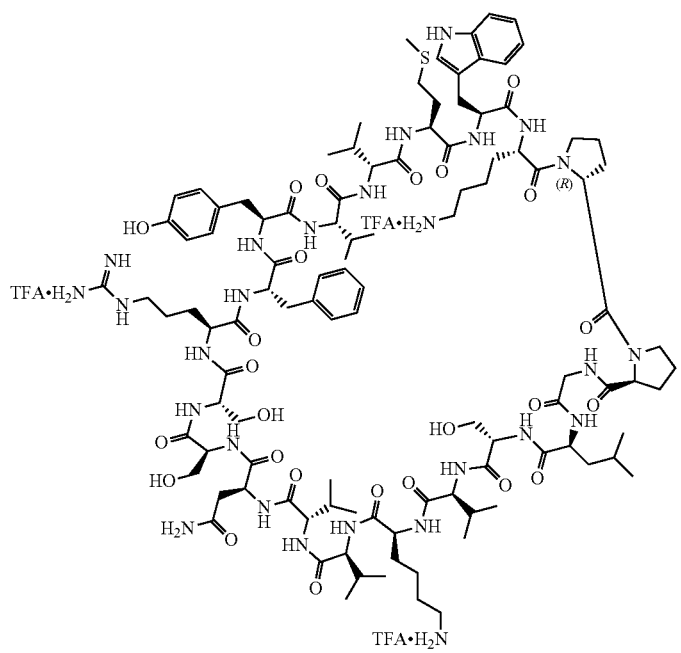 | |

TABLE I-continued

| PEP-TIDES | STRUCTURE/ AMINO: ACID SEQUENCE (linear representation) | FORMULA AND MW |
|---|---|---|
| | Chemical Formula: $C_{114}H_{167}F_9N_{27}O_{28}S$<br>Molecular Weight: 2566.80<br>—S—R—F—Y—V—V—M—W—K—p—P—G—L—S—V—K—V—V—N—S— | |
| PKTD10-1<br>(SEQ ID NO: 18) | 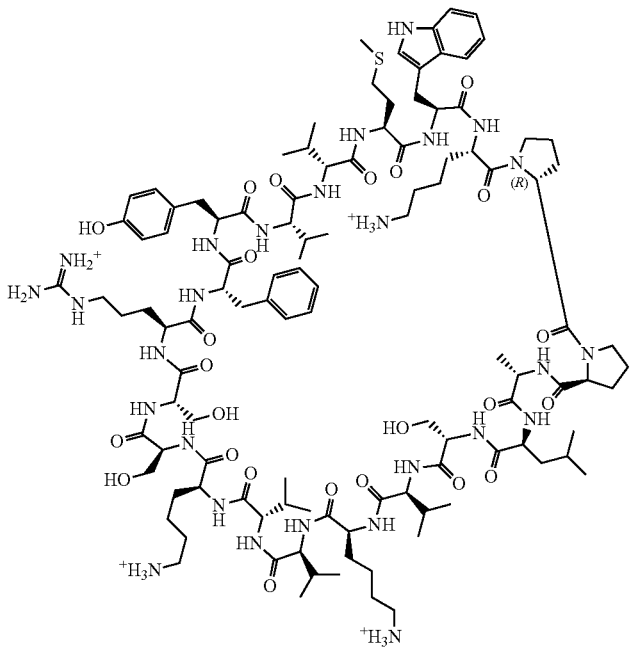 | Chemical Formula:<br>$C_{111}H_{179}N_{27}O_{24}S_{4+}$<br>Molecular Weight: 2307.88 |
| | —S—R—F—Y—V—V—M—W—K—p—P—A—L—S—V—K—V—V—N—S— | |
| PKTD10-2<br>(SEQ ID NO: 19) | 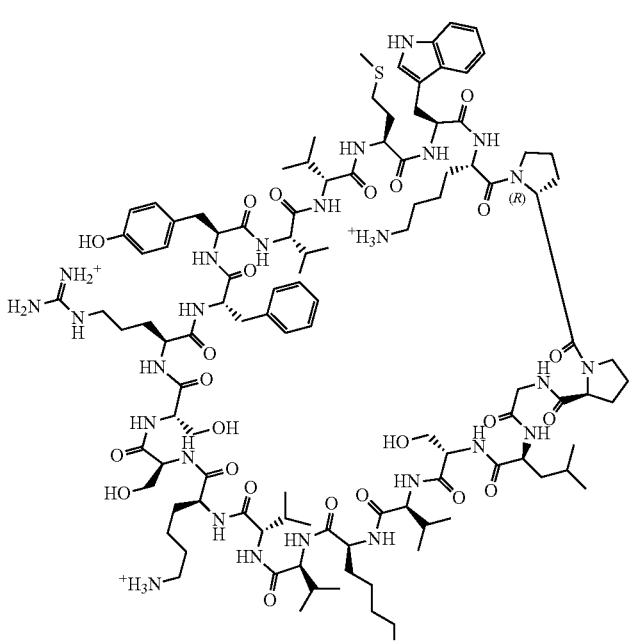 | Chemical Formula:<br>$C_{107}H_{171}N_{27}O_{24}S_{4+}$<br>Molecular Weight: 2251.77 |
| | —S—R—F—Y—V—V—M—W—K—p—P—G—A—S—V—K—V—V—N—S— | |

TABLE I-continued
| PEP-TIDES | STRUCTURE/ AMINO: ACID SEQUENCE (linear representation) | FORMULA AND MW |
|---|---|---|
| PKTD10-3 (SEQ ID NO: 20) | 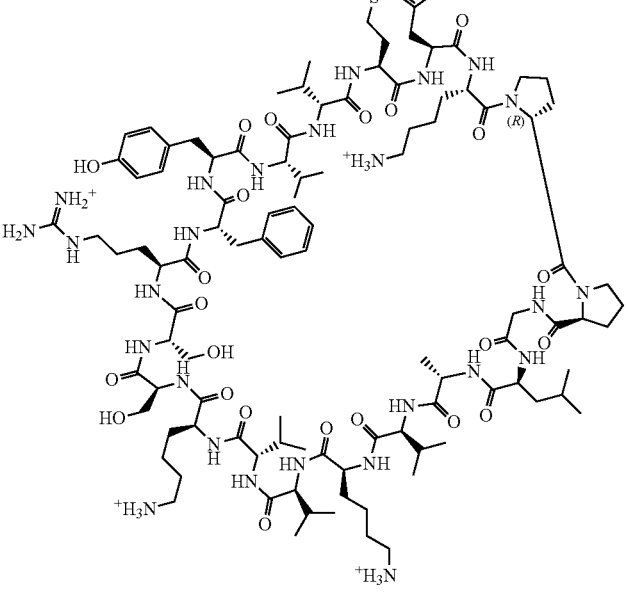<br><br>—S—R—F—Y—V—V—M—W—K—p—P—G—L—A—V—K—V—V—N—S— | Chemical Formula: $C_{110}H_{177}N_{27}O_{23}S_{4+}$<br>Molecular Weight: 2277.85 |
| PKTD10-4 (SEQ ID NO: 21) | 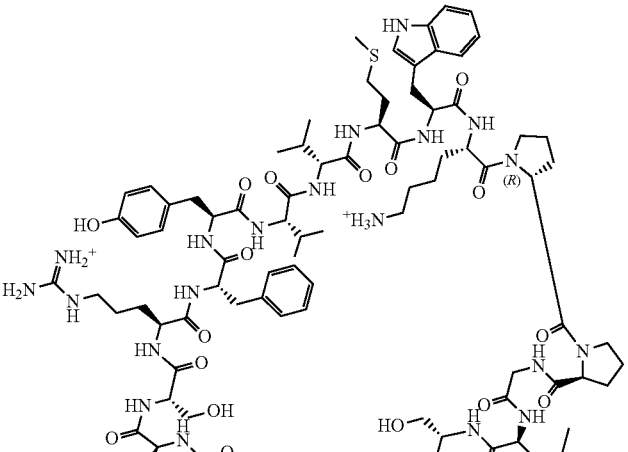<br><br>—S—R—F—Y—V—V—M—W—K—p—P—G—L—S—A—K—V—V—N—S— | Chemical Formula: $C_{108}H_{173}N_{27}O_{24}S_{4+}$<br>Molecular Weight: 2265.79 |

TABLE I-continued

| PEPTIDES | STRUCTURE/ AMINO: ACID SEQUENCE (linear representation) | FORMULA AND MW |
|---|---|---|
| PKTD10-5 (SEQ ID NO: 22) | —S—R—F—Y—V—V—M—W—K—p—P—G—L—S—V—A—V—N—S— | Chemical Formula: $C_{107}H_{169}N_{26}O_{24}S_{3+}$ Molecular Weight: 2235.75 |
| PKTD10-6 (SEQ ID NO: 23) | —S—R—F—Y—V—V—M—W—K—p—P—G—L—S—V—K—A—V—N—S— | Chemical Formula: $C_{108}H_{173}N_{27}O_{24}S_{4+}$ Molecular Weight: 2265.79 |

TABLE I-continued
| PEPTIDES | STRUCTURE/ AMINO: ACID SEQUENCE (linear representation) | FORMULA AND MW |
|---|---|---|
| PKTD10-7 (SEQ ID NO: 24) | 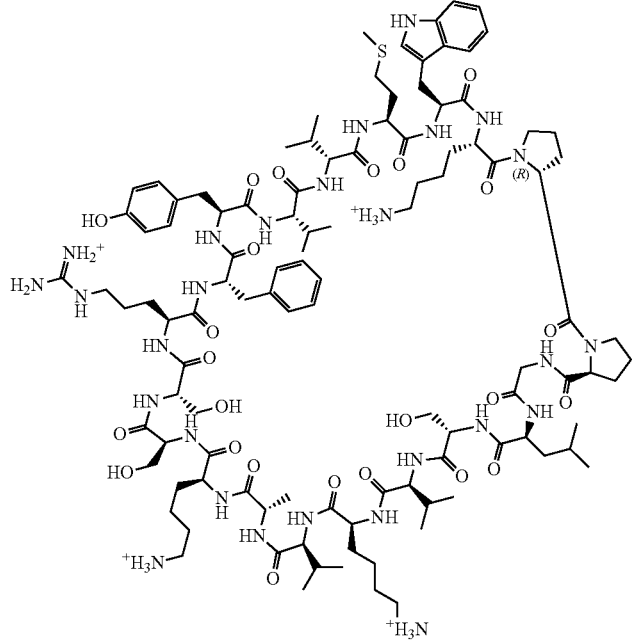<br>—S—R—F—Y—V—V—M—W—K—p—P—G—L—S—V—K—V—A—N—S— | Chemical Formula: $C_{108}H_{173}N_{27}O_{24}S_{4+}$<br>Molecular Weight: 2265.79 |
| PKTD10-8 (SEQ ID NO: 25) | 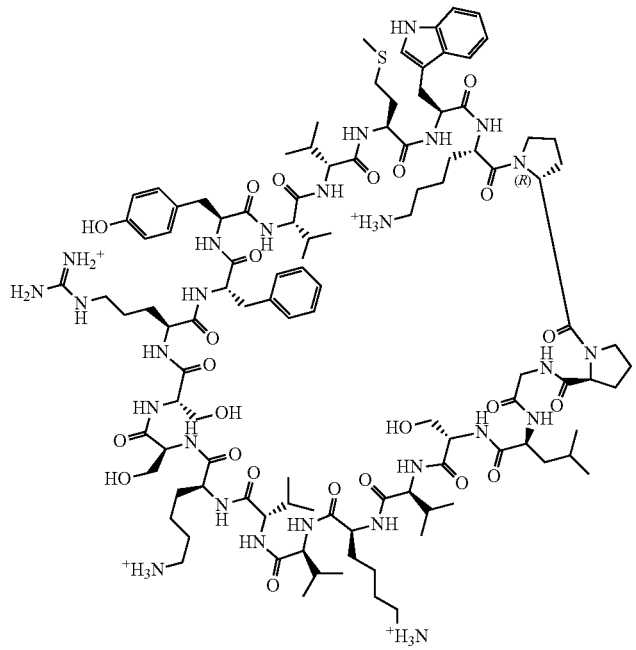<br>—S—R—F—Y—V—V—M—W—K—p—P—G—L—S—V—K—V—V—A—S— | Chemical Formula: $C_{107}H_{169}N_{26}O_{24}S_{3+}$<br>Molecular Weight: 2235.75 |

TABLE I-continued
| PEPTIDES | STRUCTURE/ AMINO: ACID SEQUENCE (linear representation) | FORMULA AND MW |
|---|---|---|
| PKTD10-9 (SEQ ID NO: 26) | 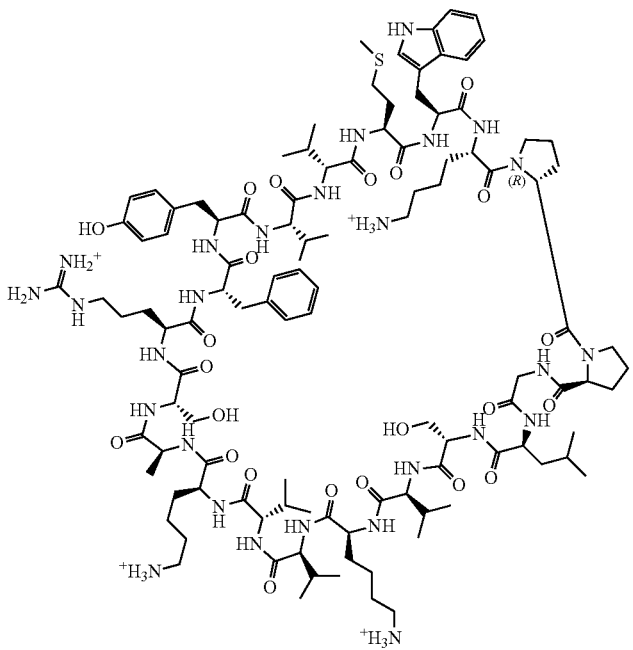<br>—S—R—F—Y—V—V—M—W—K—p—P—G—L—S—V—K—V—V—N—A— | Chemical Formula: $C_{110}H_{177}N_{27}O_{23}S_{4+}$<br>Molecular Weight: 2277.85 |
| PKTD10-RNMe (SEQ ID NO: 54) | 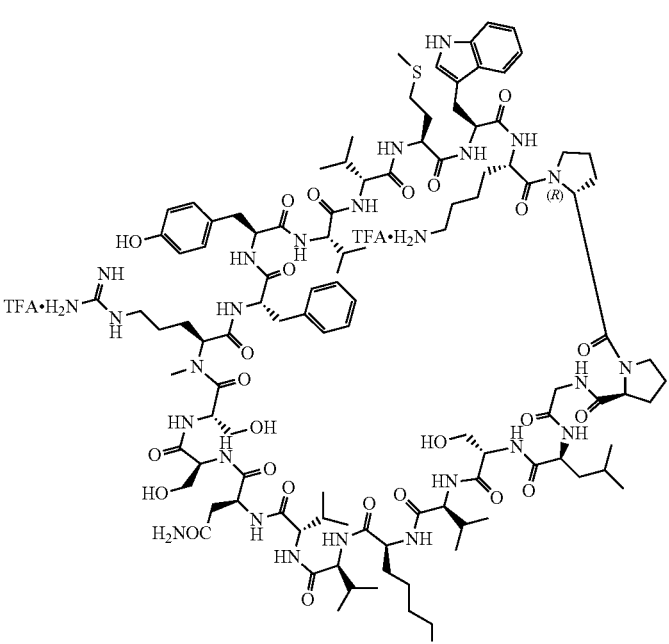<br>Chemical Formula: $C_{115}H_{169}F_9N_{27}O_{28}S$<br>Molecular Weight: 2580.82<br>—S—R*—F—Y—V—V—M—W—K—p—P—G—L—S—V—K—V—V—N—S—<br>R* = RNMe | |

TABLE I-continued

| PEP-TIDES | STRUCTURE/ AMINO: ACID SEQUENCE (linear representation) | FORMULA AND MW |
|---|---|---|
| PKTD10-X-RNMe (SEQ ID NO: 55) | Chemical Formula: $C_{116}H_{171}F_9N_{27}O_{28}$<br>Molecular Weight: 2562.79<br>—S—R*—F—Y—V—V—X—W—K—p—P—G—L—S—V—K—V—V—N—S—<br>R* = RNMe and X = NLe | |
| PKTD10-3-X-RNMe (SEQ ID NO: 56) | Chemical Formula: $C_{116}H_{171}F_9N_{27}O_{27}$<br>Molecular Weight: 2546.79<br>—S—R*—F—Y—V—V—X—W—K—p—P—G—L—A—V—K—V—V—N—S—<br>R* = RNMe and X = NLe | |

TABLE I-continued
| PEP-TIDES | STRUCTURE/ AMINO: ACID SEQUENCE (linear representation) | FORMULA AND MW |
|---|---|---|
| PKTD12 (SEQ ID NO: 29) | 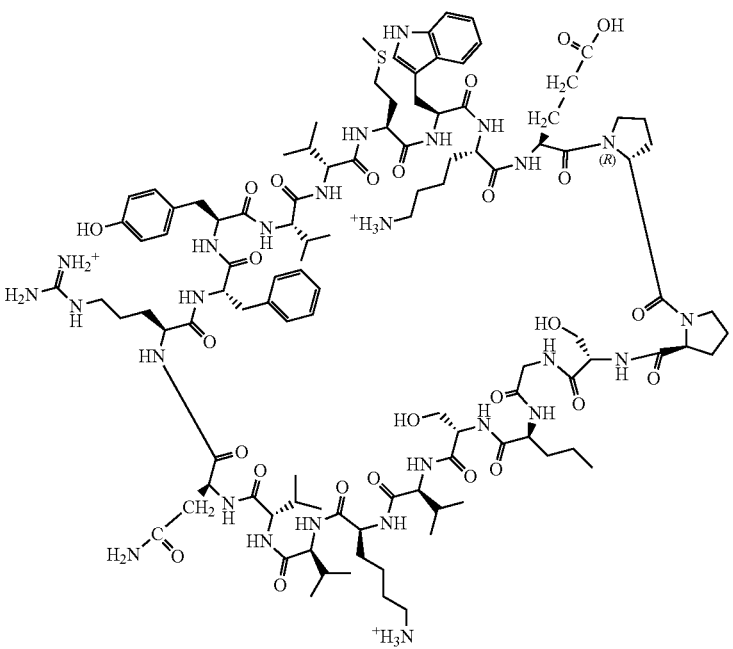<br>—R—F—Y—V—V—M—W—K—Q—p—P—S—G—L—S—V—K—V—V—N— | Chemical Formula: $C_{110}H_{177}N_{27}O_{24}S_{4+}$<br>Molecular Weight: 2293.85 |
| PKTD16 (SEQ ID NO: 33) | —S—R—F—Y—V—V—M—W—K—p—P—S—R—F—Y—V—V—M—W—K— | |
| PKTD18 (SEQ ID NO: 35) | 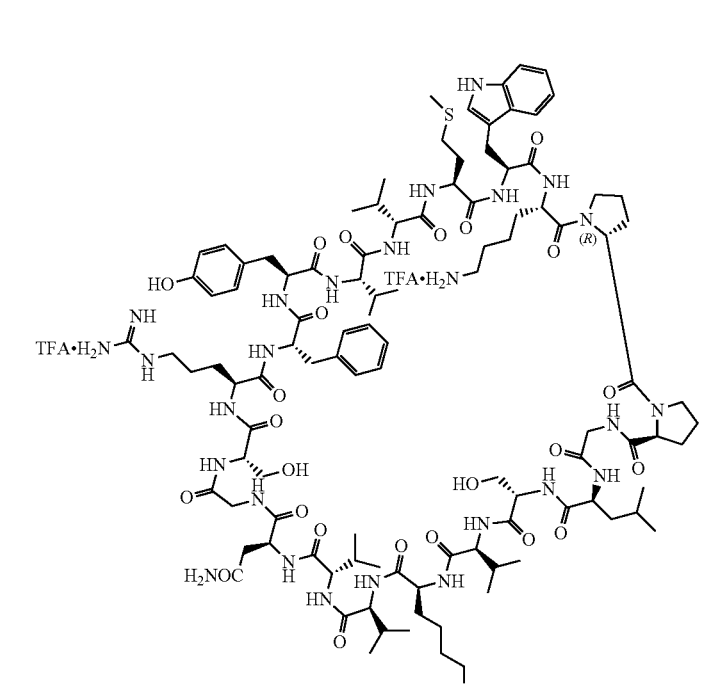<br>Chemical Formula: $C_{113}H_{165}F_9N_{27}O_{27}S$<br>Molecular Weight: 2536.77<br>—S—R—F—Y—V—V—M—W—K—p—P—G—L—S—V—K—V—V—N—G— | |

TABLE I-continued

| PEP-TIDES | STRUCTURE/ AMINO: ACID SEQUENCE (linear representation) | FORMULA AND MW |
|---|---|---|
| PKTDi1 (SEQ ID NO: 57) | [chemical structure]<br><br>Chemical Formula: $C_{109}H_{158}F_9N_{26}O_{27}S$<br>Exact Mass: 2466.14<br>Molecular Weight: 2467.66<br>—p—P—S—R—F—Y—V—V—M—W—K—G—L—S—V—K—V—V—N—S— | |
| PKTD11 (SEQ ID NO: 28) | [chemical structure]<br><br>—S—R—F—Y—V—V—M—W—K—Q—p—P—S—G—L—S—V—K—V—V—N—S— | Chemical Formula: $C_{115}H_{180}N_{29}O_{30}S_{3+}$<br>Molecular Weight: 2480.94 |

TABLE I-continued
| PEP-TIDES | STRUCTURE/ AMINO: ACID SEQUENCE (linear representation) | FORMULA AND MW |
|---|---|---|
| PKTD11Q (SEQ ID NO: 58) | 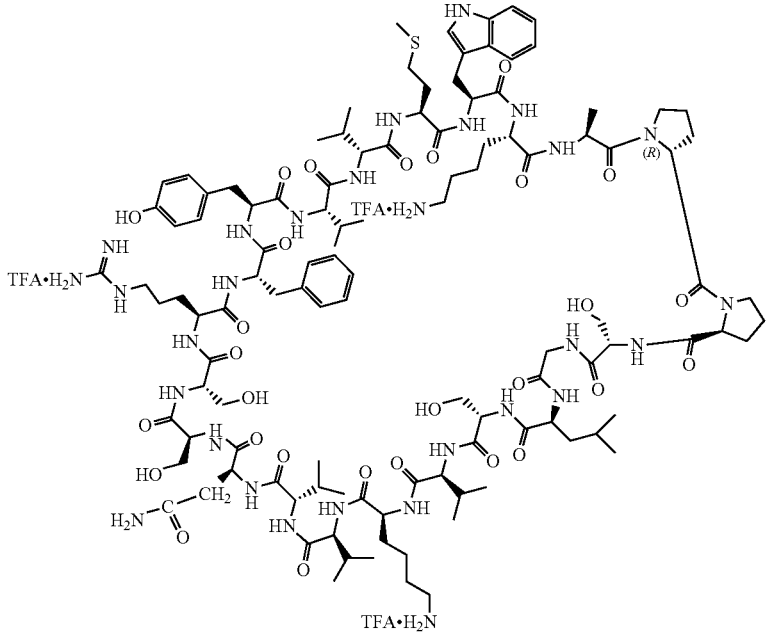 Chemical Formula: $C_{120}H_{177}F_9N_{29}O_{31}S$<br>Molecular Weight: 2724.95<br>—S—R—F—Y—V—V—M—W—K—A—p—P—S—G—L—S—V—K—V—V—N—S— | |
| PKTD11S (SEQ ID NO: 59) | 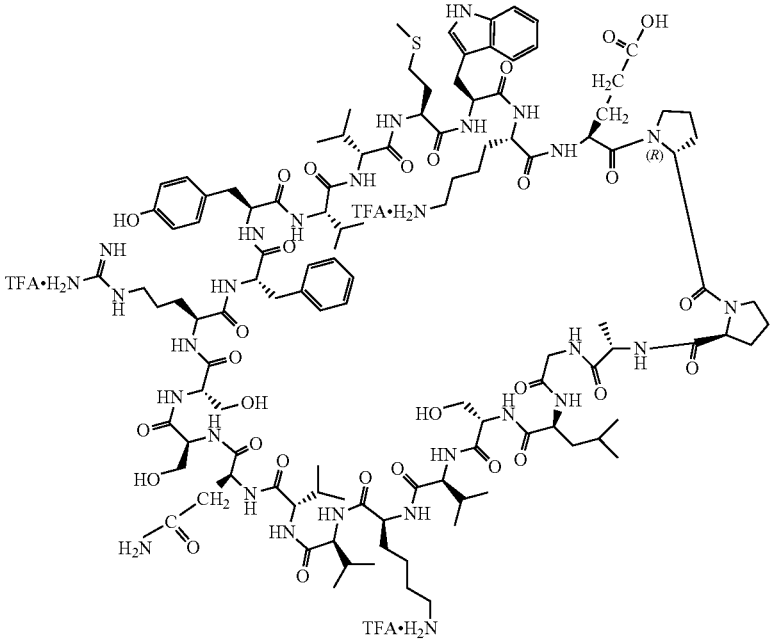 Chemical Formula: $C_{122}H_{179}F_9N_{29}O_{32}S$<br>Molecular Weight: 2766.99<br>—S—R—F—Y—V—V—M—W—K—Q—p—P—A—G—L—S—V—K—V—V—N—S— | |

TABLE I-continued
| PEP-TIDES | STRUCTURE/ AMINO: ACID SEQUENCE (linear representation) | FORMULA AND MW |
|---|---|---|
| PKTD11-RNMe (SEQ ID NO: 60) | 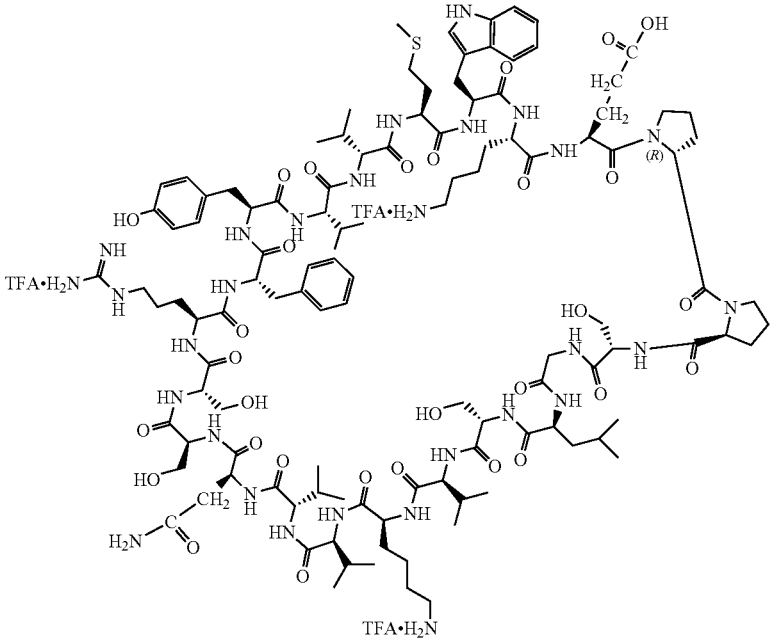 Chemical Formula: $C_{123}H_{181}F_9N_{29}O_{33}S$<br>Molecular Weight: 2797.02<br>—S—R*—F—Y—V—V—M—W—K—Q—p—P—S—G—L—S—V—K—V—V—N—S—<br>R* = RNMe | |
| PKTD11-X-RNMe (SEQ ID NO: 61) | 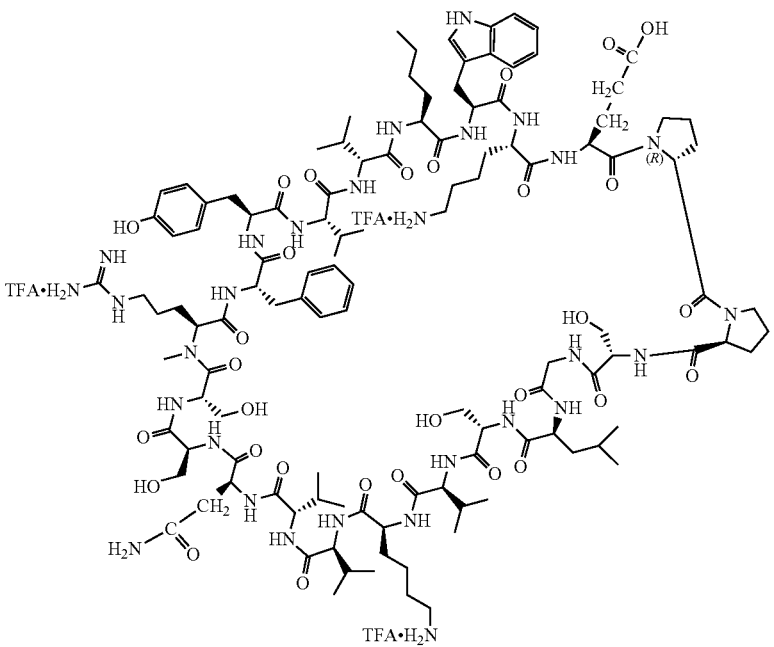 Chemical Formula: $C_{124}H_{183}F_9N_{29}O_{33}$<br>Molecular Weight: 2778.98<br>—S—R*—F—Y—V—V—X—W—K—Q—p—P—S—G—L—S—V—K—V—V—N—S—<br>R* = RNMe and X = NLe | |

Synthesis of the Cyclic Peptides of the Invention

The cyclic peptides of the invention are prepared as described in the experimental part.

Briefly, cyclic peptides of the invention are synthesized using a mixed solid/solution phase procedure leading to a linear peptide that is then cyclized. Cyclization include S—S bridges, thioether bridges, C—C bonds, C—N, ester bonds, carbon-heteroatom bonds, O—O, N—N, cyclization using scaffolds . . . .

Biologically Active Derivatives of the Cyclic Peptides of the Invention

As used herein, the term "biologically active derivatives" include the functional variants of the peptide to which it refers. More particularly, in the context of the invention, the derivative designates "biologically active derivative of the cyclic peptide of general formula (I)" are variants retaining the biological activity and the specificity of the parent peptide. Thus, in the context of the invention, said "biologically active derivatives" have are agonist of CD47 and able trigger PCD and to treat diseases associated with defects in PCD such as cancer and immunological disorders.

Preferably, the ability to trigger PCD and the antiproliferative effect of one biologically active derivative of a given cyclic peptide of general formula (I) has to be of at least about 70%, preferably between 80 and 90%, more preferably between 90 and 99% and even more preferably 100% of the antiproliferative effect, in particular to inhibit cell proliferation, of said given cyclic peptide of general formula (I) as assessed in vitro by conventional proliferation techniques.

Also, the biologically active derivatives have preferably the same specificity as the cyclic peptides of general formula (I) toward cell proliferation as assessed in vitro by conventional cellular experiments.

Said biologically active derivative can be either an allelic variant of the peptide, or a peptidomimetic variant of the peptide.

An "allelic variant of the peptide" has the same amino acid sequence as one cyclic peptide of general formula (I), except that one or more amino acids have been replaced by other amino acids or suppressed, the final peptide retaining the biological activity and specificity of the parent cyclic peptide of general formula (I). Preferably, such allelic variant has at least 50%, preferably 70%, preferably 80%, more preferably 90% and even more preferably 95% of identity as compared with the parent cyclic peptide of general formula (I).

As used herein, "percentage of identity" between two amino acid sequences denotes the percentage of amino acids residues that are identical between the two sequences to be compared, obtained after the best alignment (optimum alignment), this percentage being purely statistical and the differences between the two sequences being distributed randomly and along their entire length. Sequence comparisons between two amino acid sequences can be performed for example with the BLAST program available on the website ncbi.nlm.nih.gov/gorf/b12.html the parameters used being those given by default (in particular for the parameters "open gap penalty":5 and "extension gap penalty":2, the matrix selected being for example the "BLOSUM 62" matrix as suggested by the program, the percentage identity between the two sequences to be compared being calculated directly by the program).

Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid or another.

The biologically active derivative of the cyclic peptide of general formula (I) can also be a peptidomimetic variant, which is an organic molecule that mimics some properties of the parent peptide, including at least one or more properties of interest that preferably is its biological activity.

Preferred peptidomimetics are obtained by structural modification of cyclic peptides according to the invention, preferably using unnatural amino acids, D amino acid instead of L amino acids, conformational restraints, isosteric replacement or other modifications.

Other preferred modifications include, without limitation, those in which one or more amide bond is replaced by a non-amide bond, and/or one or more amino acid side chain is replaced by a different chemical moiety, or one or more side chain is protected by a protecting group, and/or double bonds and/or cyclization and/or stereo specificity is introduced into the amino chain to increase rigidity and/or binding affinity.

Still other preferred modifications include those intended to enhance resistance to enzymatic degradation, improvement in the bioavailability, and more generally in the pharmacokinetic properties, compared to the parent cyclic peptide of general formula (I).

Examples of such peptidomimetics include, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Chemical derivatives also include peptides that contain one or more naturally-occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. The term "conservative substitution" also includes the use of non-natural amino acids aimed to control and stabilize peptides or proteins secondary structures. These non-natural amino acids are chemically modified amino acids such as prolinoamino acids, beta-amino acids, N-methylamino acids, cyclopropylamino acids, alpha,alpha-substituted amino acids as describe here below. These non-natural amino acids may include also fluorinated, chlorinated, brominated- or iodinated modified amino acids.

Other examples of modifications include conjugation for example with lipids or carbohydrate.

All of these variations are well known in the art. Thus, given the peptide sequences of the cyclic peptide of general formula (I), those skilled in the art are enabled to design and produce peptidomimetics having biological characteristics similar to or superior to such peptides.

Preferred peptidomimetic variants of the cyclic peptide of general formula (I) retain at least the biological activity and specificity of said cyclic peptide of general formula (I).

The biologically active derivatives of the cyclic peptides of general formula (I) can be conveniently synthesized using art recognized techniques.

Therapeutic Use of the Cyclic Peptide and/or the Biologically Active Derivative Thereof of the Invention The present invention provides an isolated cyclic peptide of general formula (I) or a biologically active derivative thereof for its use as medicine.

The present invention also provides an isolated cyclic peptide of general formula (I) or a biologically active derivative thereof for use as agonist agent for triggering programmed cell death (PCD), as agent that activates CD47 and as agonist agent of CD47. More specifically, an isolated cyclic peptide of general formula (I) or a biologically active derivative thereof is useful for the treatment of diseases involving interaction of TSP1 and CD47, in particular for the treatment of diseases associated with defects in PCD; example of diseases involving apoptosis are described by Favoloro et al. (Role of apoptosis in disease, AGING, May 2012, vol. 4, No 5, pp. 330-349), importance of cell death in disease is also described by R A Knight and G Melino (Cell death in disease: from 2010 onwards, Cell Death and Disease (2011) 2, e202; doi:10.1038/cddis.2011.89); carcinogenesis is also associated with inflammation that is a defensive process against tissue injury, example of TSP-1 role in the modulation of the inflammatory process and its resolution are given by Zenaida Lopez-Dee et al. ("Thrombospondin-1: Multiple Path to inflammation, Mediators of Inflammation, Volume 2011, Article ID 296069, 10 pages doi: 10.1155/2011/296069). Once this self-protective strategy is initiated, an effective resolution of the process is crucial to avoid major and unnecessary tissue damage. If the underlying event inducing inflammation is not addressed and homeostasis is not restored, the inflammation process become chronic and lead to angiogenesis, carcinogenesis and diseases associated with immunological disorders (see Favoloro et al.) including chronic inflammation (See Lopez-Dee et al.), such as for example, multiple sclerosis, Crohn disease, psoriasis, ulcerative colitis, arthritis and asthma.

In a particular embodiment, isolated cyclic peptide of general formula (I) or a biologically active derivative thereof may be useful in the treatment of a cancer selected form the group consisting of adrenal cortical cancer, anal cancer, bile duct cancer, multiple myeloma, bladder cancer, bone cancer, brain and central nervous system cancer, breast cancer, Castleman disease, cervical cancer, colorectal cancer, endometrial cancer, esophagus cancer, gallbladder cancer, gastrointestinal carcinoid tumors, Hodgkin's disease, non-Hodgkin's lymphoma, Kaposi's sarcoma, kidney cancer, laryngeal and hypopharyngeal cancer, leukemia, liver cancer, lung cancer, mesothelioma, plasmacytoma, nasal cavity and paranasal sinus cancer, nasopharyngeal cancer, neuroblastoma, oral cavity and oropharyngeal cancer, ovarian cancer, pancreatic cancer, penile cancer, pituitary cancer, prostate cancer, retinoblastoma, rhabdomyosarcoma, salivary gland cancer, skin cancer, melanoma, stomach cancer, testicular cancer, thymus cancer, thyroid cancer, vaginal cancer, vulvar cancer, and uterine cancer.

In another particular embodiment, isolated cyclic peptide of general formula (I) or a biologically active derivative thereof may be useful in the treatment of diseases associated with chronic inflammation, including immunological diseases, selected from the group consisting of multiple sclerosis, Crohn disease, psoriasis, ulcerative colitis, arthritis and asthma.

In another embodiment, the present invention relates to a method of therapeutically treating cancer and diseases associated with chronic inflammation by administering to a subject in need thereof an effective amount of a pharmaceutical composition comprising at least an isolated cyclic peptide of general formula (I) or a biologically active derivative thereof.

Pharmaceutical Composition Comprising a Cyclic Peptide and/or a Biologically Active Derivative Thereof of the Invention The present invention also relates to pharmaceutical composition comprising an isolated cyclic peptide of general formula (I) or a biologically active derivative thereof and a pharmaceutically acceptable carrier.

In a particular embodiment of the invention, the isolated cyclic peptide of general formula (I) to be incorporated in the pharmaceutical composition of the invention is selected in group consisting of PKTD1 (SEQ ID NO: 9), PKTD3 (SEQ ID NO: 10), PKTD4 (SEQ ID NO: 11), PKTD5 (SEQ ID NO: 12), PKTD6 (SEQ ID NO: 13), PKTD7 (SEQ ID NO: 14), PKTD8 (SEQ ID NO: 15), PKTD9 (SEQ ID NO: 16), PKTD10 (SEQ ID NO: 17), PKTD10-1 (SEQ ID NO: 18), PKTD10-2 (SEQ ID NO: 19), PKTD10-3 (SEQ ID NO: 20), PKTD10-4 (SEQ ID NO: 21), PKTD10-5 (SEQ ID NO: 22), PKTD10-6 (SEQ ID NO: 23), PKTD10-7 (SEQ ID NO: 24), PKTD10-8 (SEQ ID NO: 25), PKTD10-9 (SEQ ID NO: 26), PKTD11 (SEQ ID NO: 27), PKTD12 (SEQ ID NO: 29), PKTD14 (SEQ ID NO: 31), PKTD15 (SEQ ID NO: 32), PKTD16 (SEQ ID NO: 33), PKTD17 (SEQ ID NO: 34) and PKTD18 (SEQ ID NO: 35), PKPH12 (SEQ ID NO: 39), PKPH12P (SEQ ID NO: 40), PKD8 (SEQ ID NO: 41), PKD8FF (SEQ ID NO: 42), PKD9 (SEQ ID NO: 43), PKD10 (SEQ ID NO: 44), PKD10FF (SEQ ID NO: 45), PKTDi4 (SEQ ID NO: 46), PKD11 (SEQ ID NO: 47), PKD11RNMe (SEQ ID NO: 48), PKD12 (SEQ ID NO: 49), PKD12RNMe (SEQ ID NO: 50), PKTDi3 (SEQ ID NO: 51), PKTDi5 (SEQ ID NO: 52), PKTDi2 (SEQ ID NO: 53), PKTD10-RNMe (SEQ ID NO: 54), PKTD10-X-RNMe (SEQ ID NO: 55), PKTD10-3-X-RNMe (SEQ ID NO: 56), PKTDi1 (SEQ ID NO: 57), PKTD11Q (SEQ ID NO: 58), PKTD11S (SEQ ID NO: 59), PKTD11-RNMe (SEQ ID NO: 60), PKTD11-X-RNMe (SEQ ID NO: 61) or a pharmacologically acceptable salt thereof or a biologically active derivative thereof.

For the purpose of the invention, suitable pharmaceutically acceptable carriers include, but are not limited to: water, salt solutions (e.g., NaCl), alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxymethylcellulose, and polyvinyl pyrolidone, lipids such as but not limited to: phospholipids, sphinglipids, glycerol-fatty acid esters . . . .

The pharmaceutical composition of the invention can be sterilized and if desired, mixed with auxiliary agents, e. g., lubricants, preservatives, stabilizers, wetting agents, emulsifiers, salts for influencing osmotic pressure, buffers, coloring, flavoring and/or aromatic substances and the like which do not deleteriously react with the active compounds. The pharmaceutical composition of the invention, if desired, can also contain minor amounts of wetting or emulsifying agents, or pH buffering agents.

The pharmaceutical composition of the invention can be a liquid solution, suspension, emulsion, tablet including sterile lyophilized formulation, pill, capsule, sustained release formulation, or powder. Oral formulation can include standard carriers such as pharmaceutical grades of mannitol, lactose, starch, magnesium stearate, polyvinyl pyrolidone, sodium saccharine, cellulose, magnesium carbonate, etc. Some appropriate precise formulations are described, for example, in Remington, The Science and Practice of Pharmacy, 19th edition, 1995, Mack Publishing Company.

The pharmaceutical composition of the invention can be formulated in accordance with the routine procedures as a composition adapted for intravenous administration to an individual. Typically, compositions for intravenous administration are solutions in sterile isotonic aqueous buffer or a sterile lyophilized formulation to be reconstituted prior injection, such injection can be intravenous, intramuscular, subcutaneous, intrathecal, such pharmaceutical composition can also be inhaled through nasal and/or pulmonary delivery. In a preferred embodiment the pharmaceutical composition of the invention is a liquid composition that is dedicated to be administered by injection, and for example, by intratumoral injection. Said intratumoral injection can be obtained for example by using stereotactic neurosurgery. This administration can be performed prior to or after a surgical operation intended to remove the tumor. In the first case, the composition enables to inhibit the growth of the tumor and avoid dissemination of the tumor cells and the occurrence of dramatic symptoms on the subject; in the second case, the composition can be used to destroy all the tumor cells that have not be removed during the surgical operation.

The effective dose of an isolated cyclic peptide of general formula (I) varies in function of numerous parameters such as, for example, the chosen administration method, the weight, age, sex, and the sensitivity of the individual to be treated. Consequently, the optimal dose must be determined individually, in function of the relevant parameters, by a medical specialist. In order to predict the expected active doses in human from the first animal studies presented hereunder, one can also use the $fc_2$ and $C_T$ values as described by Rocchetti et al (2007).

The following examples describe the high specificity and therapeutic efficiency of the cyclic peptides of general formula (I). They are however not limitative, in particular concerning the nature of amino acid sequence of the invention, and the experimental conditions to use it.

EXAMPLES

1. Synthesis and Characterization of the Cyclic Peptides of the Invention
General Methods:

All commercial chemicals and solvents were reagent grade and were used without further purification unless otherwise specified. All reactions except those in aqueous media were carried out with the use of standard techniques for the exclusion of moisture. All reactions were performed under argon or nitrogen in oven-dried glassware using anhydrous solvents and standard syringe techniques. Protected amino acid derivatives, HATU, HBTU, HFIP, pseudoproline dipeptides and 2-CTC resin were purchased from Iris Biotech (Marktredwitz, Germany) DIPEA, NMP, piperidine solution, DMF, IPA, TFA, PyBOP were obtained from Sigma-Aldrich. Preloaded 2-CTC resins, Dmb-amino acid, PyOxim, and Oxyma Pure were from Merck Novabiochem.

Solid-phase peptide syntheses were performed in polypropylene Torviq syringes fitted with a polyethylene porous disc at the bottom and closed with an appropriate piston. Solvent and soluble reagents were removed through back and forth movements. Removal of the Fmoc group was carried out with piperidine/DMF (20%, v/v) (1×1 min, 1×10 min). Washings between deprotection, coupling, and final deprotection steps were carried out with NMP (3×1 min), IPA (3×1 min) and NMP (3×1 min). Peptide synthesis transformations and washes were performed at 20° C. Supported coupling reactions were monitored by classical Kaiser test (directly prepared solution kit from Sigma-Aldrich). Compounds molecular weights were calculated using ChemBioDraw® Ultra 12. All final products were of >95% purity unless otherwise indicated (determined by analytical reverse phase LCMS). Analytical data are given in Table II.

Five methods were conducted for LC-MS analysis:

Method A: analytical HPLC was conducted on a X-Select CSH C18 XP column (2.5 µm 30×4.6 mm id) eluting with 0.1% formic acid in water (solvent A) and 0.1% formic acid in acetonitrile (solvent B), using the following elution gradient 0-3.20 minutes: 5% to 100% B, 3.20-4 minutes 100% B, at a flow rate of 1.8 ml/minute at 40° C. The mass spectra (MS) were recorded on a Waters ZQ mass spectrometer using electrospray positive ionisation [ES+ to give MH$^+$ molecular ions] or electrospray negative ionisation [ES$^-$ to give (M-H)$^-$ molecular ions] modes. The cone voltage was 20V.

Method B: analytical HPLC was conducted on a X-Select CSH C18 XP column (2.5 µm 30×4.6 mm id) eluting with 0.1% formic acid in water (solvent A) and 0.1% formic acid in acetonitrile (solvent B), using the following elution gradient 0-10 minutes: 40% to 100% B, 10-11 minutes 100% B, at a flow rate of 1.8 ml/minute at 40° C. The mass spectra (MS) were recorded on a Waters ZQ mass spectrometer using electrospray positive ionisation [ES$^+$ to give MH$^+$ molecular ions] or electrospray negative ionisation [ES– to give (M-H)– molecular ions] modes. The cone voltage was 20V.

Method C: analytical HPLC was conducted on a X-Select CSH C18 XP column (2.5 µm 30×4.6 mm id) eluting with 0.1% formic acid in water (solvent A) and 0.1% formic acid in acetonitrile (solvent B), using the following elution gradient 0-3.20 minutes: 0% to 50% B, 3.20-4 minutes 100% B, at a flow rate of 1.8 ml/minute at 40° C. The mass spectra (MS) were recorded on a Waters ZQ mass spectrometer using electrospray positive ionisation [ES+ to give MH+ molecular ions] or electrospray negative ionisation [ES– to give (M-H)– molecular ions] modes. The cone voltage was 20V.

Method D: analytical HPLC was conducted on a X-Select CSH C18 XP column (2.5 µm 30×4.6 mm id) eluting with 0.1% formic acid in water (solvent A) and 0.1% formic acid in acetonitrile (solvent B), using the following elution gradient 0-6 minutes: 0% to 50% B, 6-7 minutes 100% B, at a flow rate of 1.8 ml/minute at 40° C. The mass spectra (MS) were recorded on a Waters ZQ mass spectrometer using electrospray positive ionisation [ES+ to give MH+ molecular ions] or electrospray negative ionisation [ES– to give (M-H)– molecular ions] modes. The cone voltage was 20V.

Method E: Analytical HPLC was conducted on a X-Select CSH C18 XP column (2.5 µm 30×4.6 mm id) eluting with 0.1% formic acid in water (solvent A) and 0.1% formic acid in acetonitrile (solvent B), using the following elution gradient 0-3 minutes: 5% to 100% B, 3-4 minutes 100% B, at a flow rate of 1.8 ml/minute at 40° C. The high resolution mass spectra (MS) were recorded on a Waters LCT mass spectrometer using electrospray positive ionisation [ES+ve to give MH+ molecular ions] or electrospray negative ionisation [ES–ve to give (M-H)– molecular ions] modes.

Purifications were performed by reverse phase HPLC on either a Waters semi-preparative HPLC-system connected to a Breeze software or a Dionex semi-preparative HPLC-system connected to a Chromeleon softwares, using a C18 semi-preparative columns from AIT using as eluent A, H$_2$O containing 0.1% of TFA and as eluent B, CH$_3$CN containing 0.1% of TFA, at a flow rate of 5 mL/min. UV detection was done at 220 nm and at 280 nm. Purification gradients were chosen to get a ramp of approximately 1% solution B per minute in the interest area.

Cyclic Peptide Synthesis:

Cyclic peptides were synthesized using a mixed solid/solution phase procedure. A typical supported synthesis is reported as described earlier (see Peptidomimetic Antibiotics Target Outer-Membrane Biogenesis in *Pseudomonas aeruginosa*, Nityakalyani Srinivas et al. published 19 Feb. 2010, *Science* 327, 1010 (2010)). 2-Chlorotritylchloride resin was previously swelled in anhydrous $CH_2Cl_2$ for 2 h. Fmoc-Aa-OH (0.32 mmol) was coupled to 2-CTC resin (400 mg, loading=1.6 mmol/g) in the presence of diisopropyethylamine (DIPEA, 4 eq.) in $CH_2Cl_2$ (4 mL). The unreacted sites on the resin were capped by washing with a mixture of $CH_2Cl_2$/MeOH/DIPEA (7:2:1) followed by MeOH. After removal of the Fmoc-group using 20% piperidine in N,N-dimethylformamide (DMF), chain elongation was performed with standard Fmoc-protected amino acids (Bachem, Switzerland), using 20% piperidine/DMF for Fmoc deprotection, 2-(1H-benzotriazole-1-yl)-1,1,3,3-tetramethyluronium hexafluorophosphate/1-hydroxybenzotriazole (HBTU/HOBt) for activation, DIPEA as base and N-methyl-2-pyrrolidinone (NMP) as solvent. When assembly of the linear peptide chain was complete, additional MeOH wash was carried for final washing step (1×1 min, 1×15 min) in order to shrink the resin.

Linear peptides were cleaved from the resin by 2 times treatment with $HFIP/CH_2Cl_2$ cocktail (1:4, v/v) for 15 min each. The reaction mixture is filtered and the resin is sequentially rinsed with $CH_2Cl_2$ and MeOH. The filtrates are pooled and the solvents were subsequently evaporated under reduced pressure. At the end, the crude linear peptide was precipitated 3 times using dry-ice cold $EtO_2$ and recovered after centrifugations (3×5 min, 7800 rpm) and drying (under nitrogen flow). The latter system is especially suitable for the cleavage of fully protected fragments to be cyclized in solution, as it eliminates the use of a carboxylic acid in the cleavage step.

For cyclization, the resulting linear peptide (1 eq.) was dissolved in DMF (1 mg/mL concentration), PyBOP (2 eq.), and HOBt (2 eq.) were added to the solution. The pH was adjusted to 8 by adding DIPEA (1% v/v) and the mixture was stirred until LC-MS analysis indicated the completion of the reaction (between 2 and 20 h). The solvent was removed under reduced pressure. In order to remove excess of coupling agents the crude peptide was redissolved in $CH_2Cl_2$ or Me-THF (50 mL) and organic layer was extracted with saturated $NaHCO_3$ (2×20 mL) and brine (2×20 mL), dried with $Na_2SO_4$ and then evaporated under vacuum. After evaporation, $TFA/H_2O/TIS$ final deprotection cocktail (95/2.5/2.5, 20 mL) was smoothly added. The resulting mixture was stirred for 3 h and then precipitated 3 times using dry-ice cold $EtO_2$ (3×30 mL) and recovered after centrifugations (3×5 min, 7800 rpm) and drying (under nitrogen flow).

The resulting crude cyclic peptide was dissolved in aqueous (11% (v/v) TFA. Purification was conducted on reversed-phase HPLC Prep C18 column, eluting with 0.1% TFA in water (solvent A) and 0.1% TFA in acetonitrile (solvent B), using the following elution gradient of 15% to 35% B in 30 min, at a flow rate of 14 ml/min at 20° C. Peptide fractions from purification were analysed by analytical LC-MS (method C or D), pooled according to their purity and lyophilized on an Alpha 2/4 freeze dryer from Bioblock Scientific to get the expected macrocyclic peptide (mg, µmol) as a white powder with an overall yield of 7%.

TABLE II (Peptides Molecular Weights given as free ammonium)

| Peptide | Mw (g · mol$^{-1}$) | m/z (ESI) | $t_R$ (method) |
|---|---|---|---|
| PKTD1 | 2289.8 | 764.2 $[M + 3H]^{3+}$ | 2.33 (C) |
|  |  | 573.5 $[M + 4H]^{4+}$ |  |
| PKTD3 | 2261.7 | 1131.8 $[M + 2H]^{2+}$ | 2.25 (C) |
|  |  | 754.9 $[M + 3H]^{3+}$ |  |
|  |  | 566.4 $[M + 4H]^{4+}$ |  |
| PKTD6 | 2275.7 | 1138.7 $[M + 2H]^{2+}$ | 2.50 (C) |
|  |  | 749.4 $[M + 3H]^{3+}$ |  |
| PKTD7 | 2101.6 | 701.5 $[M + 3H]^{3+}$ | 2.94 (D) |
| PKTD9 | 2424.8 | 809.3 $[M + 3H]^{3+}$ | 4.69 (D) |
| PKTD10 | 2275.8 | 1138.7 $[M + 2H]^{2+}$ | 2.35 |
|  |  | 759.4 $[M + 3H]^{3+}$ |  |
| PKTD10-NMe | 2289.8 | 1145.6 $[M + 2H]^{2+}$ | 2.52 |
|  |  | 764.0 $[M + 3H]^{3+}$ |  |
| PKTD10-X-NMe | 2271.7 | 1136.6 $[M + 2H]^{2+}$ | 2.62 |
|  |  | 758.0 $[M + 3H]^{3+}$ |  |
| PKTD11 | 2491.0 | 1246.3 $[M + 2H]^{2+}$ | 2.45 |
|  |  | 831.1 $[M + 3H]^{3+}$ |  |
| PKTD11-NMe | 2505.0 | 1253.1 $[M + 2H]^{2+}$ | 2.40 |
|  |  | 838.5 $[M + 3H]^{3+}$ |  |
| PKTD11-Q | 2433.9 | 1217.7 $[M + 2H]^{2+}$ | 2.59 |
|  |  | 812.1 $[M + 3H]^{3+}$ |  |
| PKTD11-S | 2475.0 | 1238.4 $[M + 2H]^{2+}$ | 2.46 |
|  |  | 825.9 $[M + 3H]^{3+}$ |  |
| PKTD12 | 2316.8 | 1159.3 $[M + 2H]^{2+}$ | 2.40 |
|  |  | 773.1 $[M + 3H]^{3+}$ |  |
| PKTD16 | 2589.2 | 1295.3 $[M + 2H]^{2+}$ | 2.38 |
|  |  | 863.9 $[M + 3H]^{3+}$ |  |
|  |  | 648.1 $[M + 4H]^{4+}$ |  |
| PKTD18 | 2245.7 | 1123.6 $[M + 2H]^{2+}$ | 2.51 |
|  |  | 749.3 $[M + 3H]^{3+}$ |  |
| PKTDi1 | 2275.8 | 1138.7 $[M + 2H]^{2+}$ | 2.37 |
|  |  | 759.4 $[M + 3H]^{3+}$ |  |
| PKTDi2 | 2101.6 | 1151.6 $[M + 2H]^{2+}$ | 2.28 |
|  |  | 701.3 $[M + 3H]^{3+}$ |  |
| PKTDi3 | 1831.3 | 1831.9 $[M + 2H]^{2+}$ | 2.85 |
|  |  | 916.4 $[M + 3H]^{3+}$ |  |
| PKTDi4 | 1646.1 | 1646.7 $[M + 2H]^{2+}$ | 3.26 |
|  |  | 823.8 $[M + 3H]^{3+}$ |  |
| PKD8 | 1646.1 | 1646.7 $[M + 2H]^{2+}$ | 3.57 |
|  |  | 823.8 $[M + 3H]^{3+}$ |  |
| PKD9 | 1628.0 | 1628.7 $[M + 2H]^{2+}$ | 3.64 |
|  |  | 814.7 $[M + 3H]^{3+}$ |  |
| PKD10 | 1643.1 | 1643.8 $[M + 2H]^{2+}$ | 3.12 |
|  |  | 822.3 $[M + 3H]^{3+}$ |  |
| L-PKD10 | 1661.1 | 1661.7 $[M + 2H]^{2+}$ | 2.65 |
|  |  | 831.1 $[M + 3H]^{3+}$ |  |
| PKD10-FF | 1627.1 | 1627.8 $[M + 2H]^{2+}$ | 3.33 |
|  |  | 814.3 $[M + 3H]^{3+}$ |  |

2. In Vitro Activity of Cyclic Peptides According to the Invention

The effects of several cyclic peptides of the invention on the proliferation of tumor cells were evaluated on 5 cell lines (MCF-7, human breast cancer cells; HCT-116, human colon cancer cells; BxPC3, human pancreas cancer cells and A549, human lung cancer cells) by cytotoxic assay and by counting directly the number of cells.

2.1. Materials

The cyclic peptides of general formula (I), PKTD1, PKTD7, PKTD9, PKTD10, PKTD10-3, PKTD10-RNMe, PKTD10-X-RNMe, PKTD10-4, PKTD11, PKTD11RNMe, PKTD12, PKTD16, PKTD18, PKD8, PKD10 and PKD10-FF were synthesized as described in the experimental part.

Those cyclic peptides were dissolved in DMSO at the following concentrations: 0, 5, 10, 25, 50 and 100 µM.

PKC1 is a cyclic peptide that only comprise fragment of beta-strand No 7 of TSP-1 (SEQ ID NO:8); its structure is as follows:

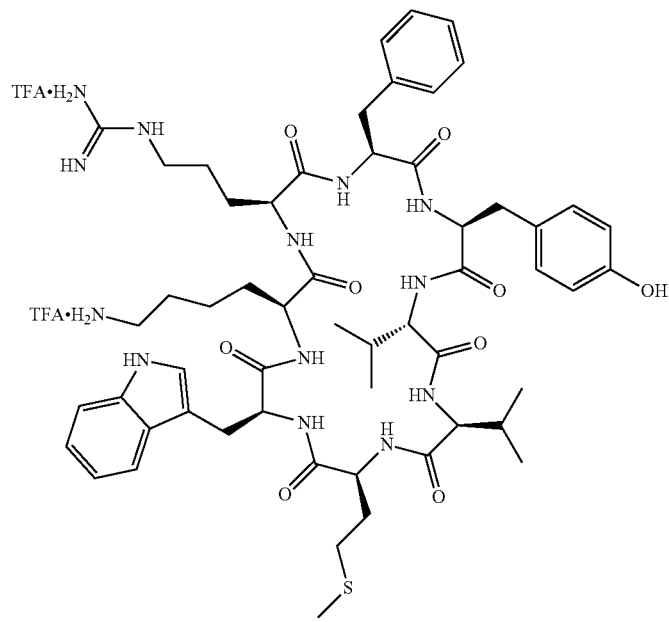
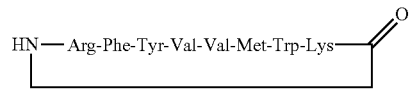

Chemical Formula: $C_{60}H_{79}F_6N_{13}O_{11}S$
Molecular Weight: 1304,42

Linear PKT16 peptide [(D)Lys-(N-Me)Arg-Phe-Tyr-Val-Val-Nle-Trp-Lys-(D)Lys] (SEQ ID NO:66) was used as positive control.

Compound CTGG (also called 4NGG, a linear peptide of sequence KRFYGGMWKK) was used as negative control.

Culture media used for these assays are: EMEM=10% SVF for MCF-7 and Wi38; RPMI 1640=10% SVF for HCT-116 and BxPC3 and F-12K=10% SVF for A549.

2.2. Methods 2.2.1. Analysis of Cell Viability and Proliferation 500 cells were seeded in 96-well plates, incubated at 37° C. for 24 hours, and treated by the cyclic peptides at the different concentrations and controls for 2 h.

2.2.2. Cell Death Analysis by Flow Cytometry

To detect possible apoptotic processes, cells were seeded in 35 mm dishes and cultured in media containing each tested cyclic peptide for 2 hours following procedure A or B.

Procedure A: Etopiside (40 nM) was used as a positive control to induce apoptosis. Cells were then trypsinized, washed in cold PBS, and stained with Annexin V-FrrC (BD Pharmingen) in Annexin buffer for 15 min at room temperature. Finally, they were counterstained with 50 µg/mL propidium iodide (Sigma) and analyzed with a FACSCalibur flow cytometer. Experiment on each cell type was repeated three times. 20,000 events per sample were analyzed in each experiment.

Procedure B: Peptides were incubated for 2 hours on HCT-116 cells. Superkiller Trail (ALX-201-115C-010) was used as a positive pro-apoptotic control. Cells were analyzed by cytofluorometry using FITC Annexin V apoptosis detection kit with 7-AAD from BIOLEGEND (BLE640922).

2.3. Results

Results of these assays are presented in FIGS. 7A to 7F and in the tables III to VI below:

TABLE III

| | | Mean (%) | | |
|---|---|---|---|---|
| | | Late apoptosis | Early Apoptosis | Viable |
| Superkiller | 100 ng/mL | 1.79 | 52.55 | 45.59 |
| PKTD10-3 | 0 | 2.04 | 2.83 | 94.96 |
| | 12.5 | 4.35 | 8.17 | 86.83 |
| | 25 | 7.06 | 13.16 | 79.30 |
| | 50 | 6.85 | 13.13 | 79.67 |
| PKTD10-4 | 0 | 2.04 | 2.83 | 94.96 |
| | 12.5 | 4.39 | 9.27 | 85.90 |
| | 25 | 5.54 | 11.91 | 82.41 |
| | 50 | 7.53 | 15.68 | 76.52 |
| PKTD10-RNMe | 0 | 2.04 | 2.83 | 94.96 |
| | 12.5 | 2.17 | 5.97 | 91.72 |
| | 25 | 2.77 | 6.04 | 91.10 |
| | 50 | 8.10 | 14.95 | 76.73 |
| PKTD12 | 0 | 2.04 | 2.83 | 94.96 |
| | 12.5 | 3.11 | 5.78 | 90.87 |
| | 25 | 3.26 | 7.15 | 89.42 |
| | 50 | 6.80 | 19.16 | 73.78 |

TABLE IV

| | | Mean (%) | | |
|---|---|---|---|---|
| | | Late apoptosis | Early Apoptosis | Viable |
| Superkiller | 100 ng/mL | 2.06 | 41.42 | 56.39 |
| DMSO | 0 | 7.41 | 5.72 | 86.35 |
| PKD10 | 12.5 | 15.76 | 18.30 | 65.66 |
| | 25 | 24.58 | 43.67 | 31.50 |
| | 50 | 39.02 | 32.70 | 27.55 |
| PKTD1 | 0 | 7.41 | 5.72 | 86.35 |
| | 12.5 | 11.60 | 11.42 | 76.44 |
| | 25 | 18.77 | 17.24 | 63.51 |
| | 50 | 36.99 | 24.68 | 37.56 |
| PKTD9 | 0 | 7.41 | 5.72 | 86.35 |
| | 12.5 | 7.83 | 9.78 | 82.19 |
| | 25 | 8.58 | 11.40 | 79.38 |
| | 50 | 14.94 | 13.32 | 70.52 |

TABLE V

| | | Mean (%) | | |
|---|---|---|---|---|
| | | Late apoptosis | Early Apoptosis | Viable |
| Superkiller | 100 ng/mL | 1.79 | 52.55 | 45.59 |
| PKD10 | 0 | 2.04 | 2.83 | 94.96 |
| | 12.5 | 10.07 | 40.48 | 49.30 |
| | 25 | 16.97 | 59.50 | 23.28 |
| | 50 | 56.90 | 28.42 | 12.74 |
| PKTD10-X-NMe | 0 | 2.04 | 2.83 | 94.96 |
| | 12.5 | 5.15 | 11.92 | 82.76 |
| | 25 | 6.96 | 17.66 | 75.17 |
| | 50 | 20.43 | 30.86 | 48.31 |
| PKTD11RNMe | 0 | 2.04 | 2.83 | 94.96 |
| | 12.5 | 3.17 | 7.80 | 88.71 |
| | 25 | 3.99 | 9.39 | 86.38 |
| | 50 | 9.58 | 23.06 | 67.03 |
| PKTD18 | 0 | 2.04 | 2.83 | 94.96 |
| | 12.5 | 5.21 | 12.14 | 82.45 |
| | 25 | 8.59 | 15.95 | 75.12 |
| | 50 | 9.60 | 22.48 | 67.48 |

TABLE VI

| | | Mean (%) | | |
|---|---|---|---|---|
| | | Late apoptosis | Early Apoptosis | Viable |
| Superkiller | 100 ng/mL | 1.54 | 48.43 | 49.92 |
| DMSO | 0 | 1.60 | 2.94 | 95.35 |
| PKD10 | 12.5 | 5.14 | 11.41 | 83.31 |
| | 25 | 7.36 | 45.90 | 46.71 |
| | 50 | 24.87 | 50.77 | 23.93 |
| PKD10-FF | 0 | | 6.79 | 93.2 |
| | 12.5 | | 74.66 | 25.225 |
| | 25 | | 69.29 | 30.445 |
| | 50 | | 67.35 | 31.97 |
| PKC1 | 12.5 | 2.25 | 4.54 | 92.95 |
| | 25 | 2.56 | 4.55 | 92.72 |
| | 50 | 2.75 | 4.98 | 92.15 |

All tested cyclic peptides PKTD1, PKTD7, PKTD9, PKTD10, PKTD10-3, PKTD10-RNMe, PKTD10-X-RNMe, PKTD10-4, PKTD11, PKTD11RNMe, PKTD12, PKTD16, PKTD18, PKD10 and PKD10-FF show a dose-dependent viability decrease in all cell strains (from 20 to 80% of PCD induction in 2 hours from 10 to 50 µM peptide concentration). This activity is significantly higher than positive control (PKT16) which is not efficient at the concentrations tested here (efficacy to induce PCD not observed at 100 µM).

Cyclic peptide PKC1 shows no efficacy in triggering PCD whatever the concentration used (from 12.5 to 50 µM, same results are observed); this result demonstrates the importance of the cyclic hairpin structure involving the beta strands 6 and 7 or 7 and 8 of TSP-1, highlighting the fact that the simple cyclisation of the 4N1 CD47-binding epitope of TSP-1 is not sufficient to improve its potency.

Figure 7F:
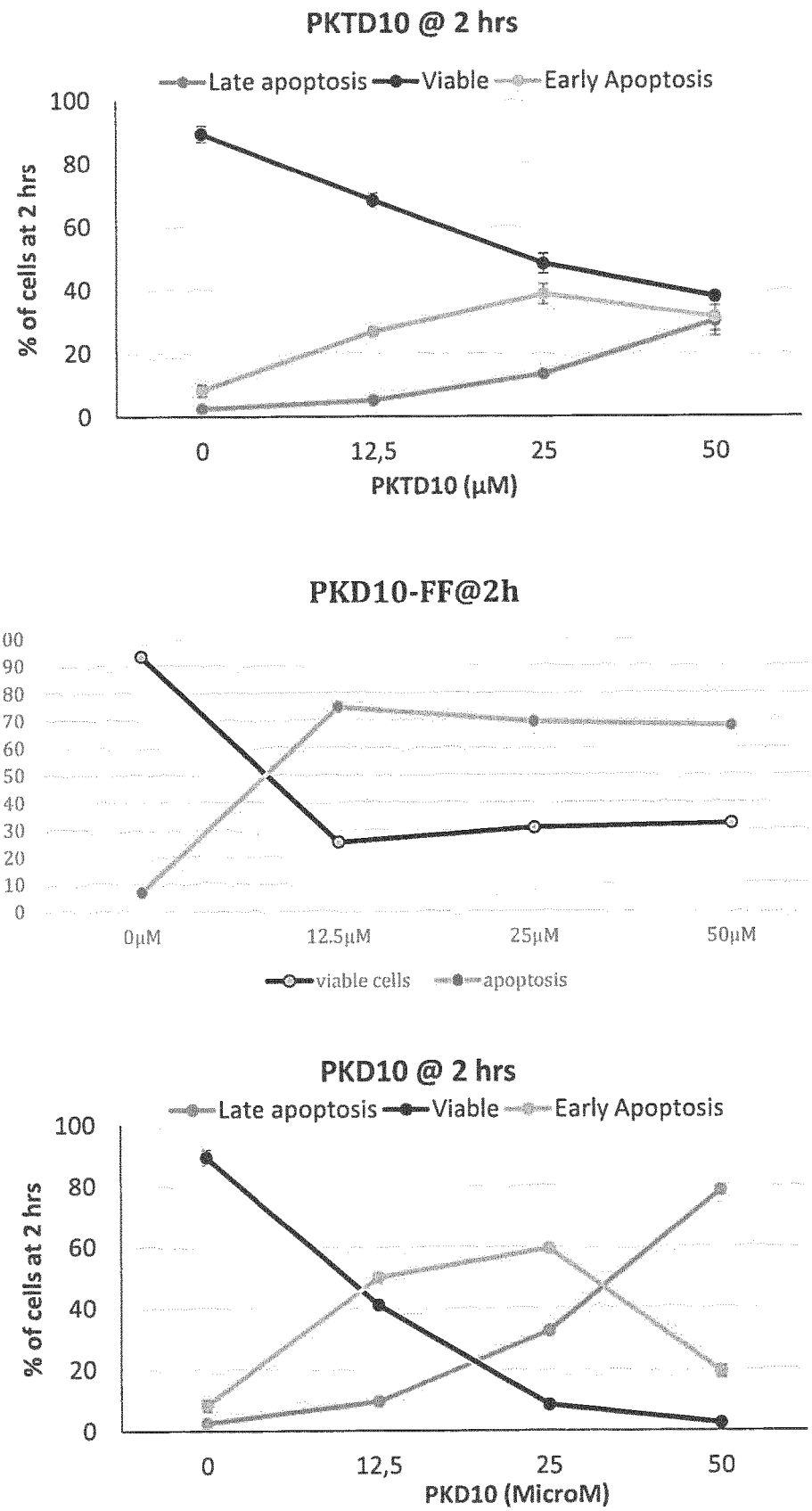

Cyclic peptide PKD10 induces a very significant decrease of cell viability at a low dose (25 µM) after 2 hours of incubation (FIG. 7F).

These results thus allow considering cyclic peptide of the invention as very promising tools for treating diseases associated with defects in PCD such as tumors and immunological diseases (including diseases associated with chronic inflammation), either in animals or in human beings. Besides its therapeutic efficiency in reducing tumor size, those cyclic peptides do not show strong toxicity usually associated with cytotoxic drugs. It is therefore embodied as being the future therapeutic agent for treating patients suffering from tumors.

3. Binding Experiments

Binding affinity measurements. The binding affinities of peptides, here PKT16, PKTD1, PKTD10, PKTD10-1, PKTD10-3, PKTD10-5, PKDT10-7 and PKTD10-8 for a membrane preparation from Jurkat and/or MEC-1 cells were measured by Microscale Thermophoresis[xlv] on a Monolith NT115-pico system (Nanotemper Technologies, Munich, Germany).

Figure 5:
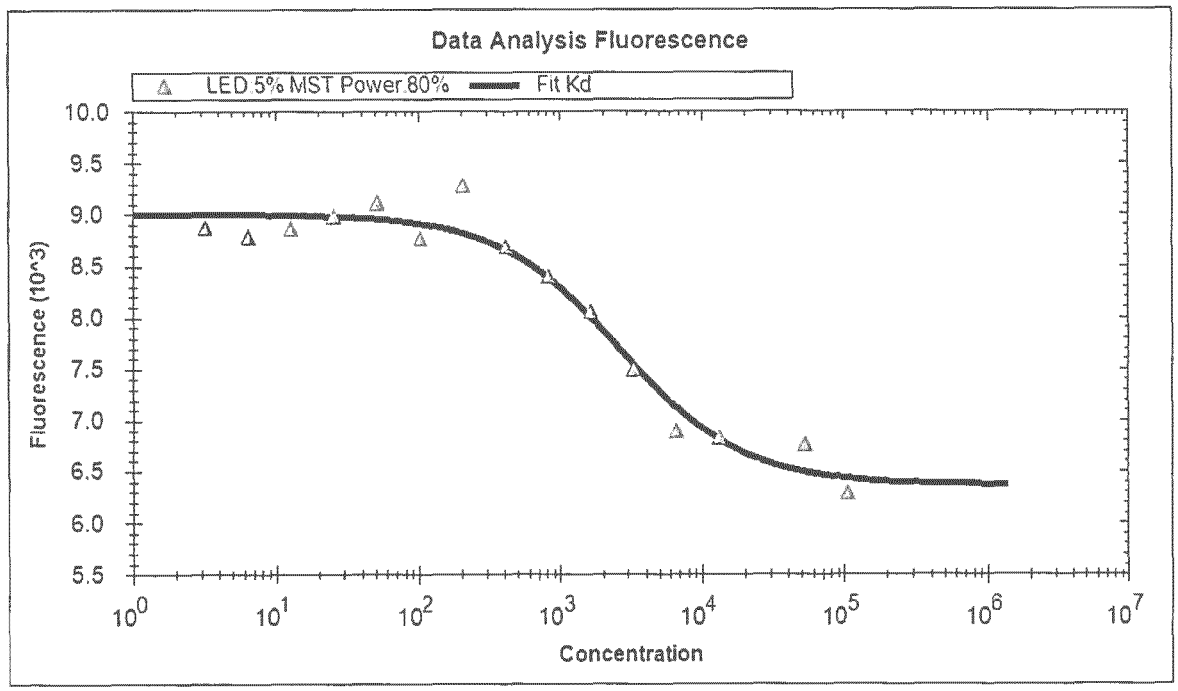
Figure 6A:
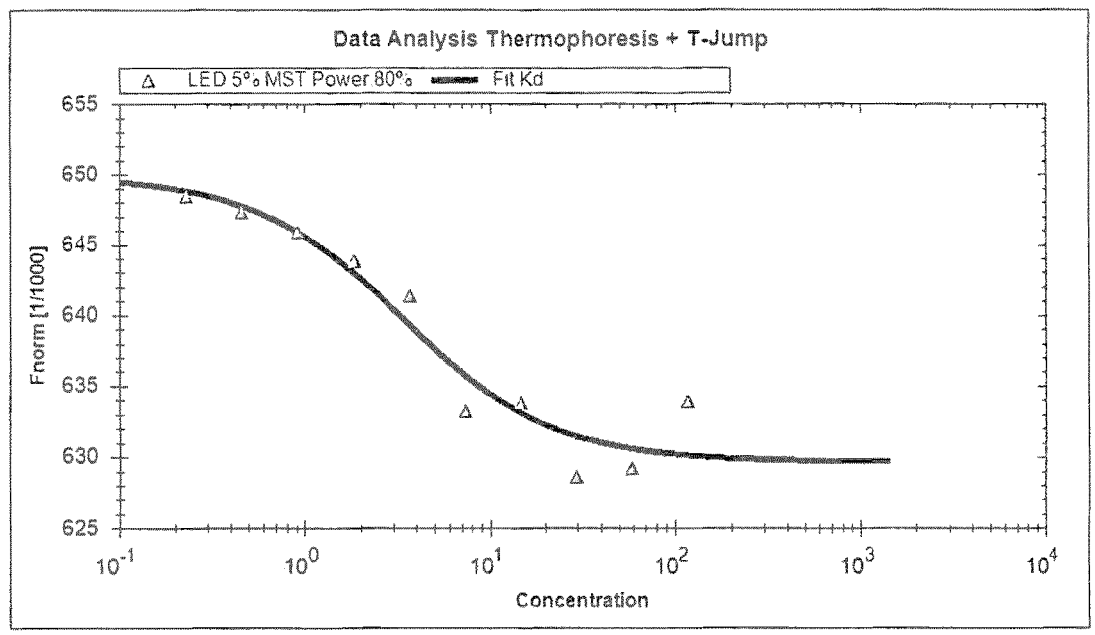
Figure 6B:
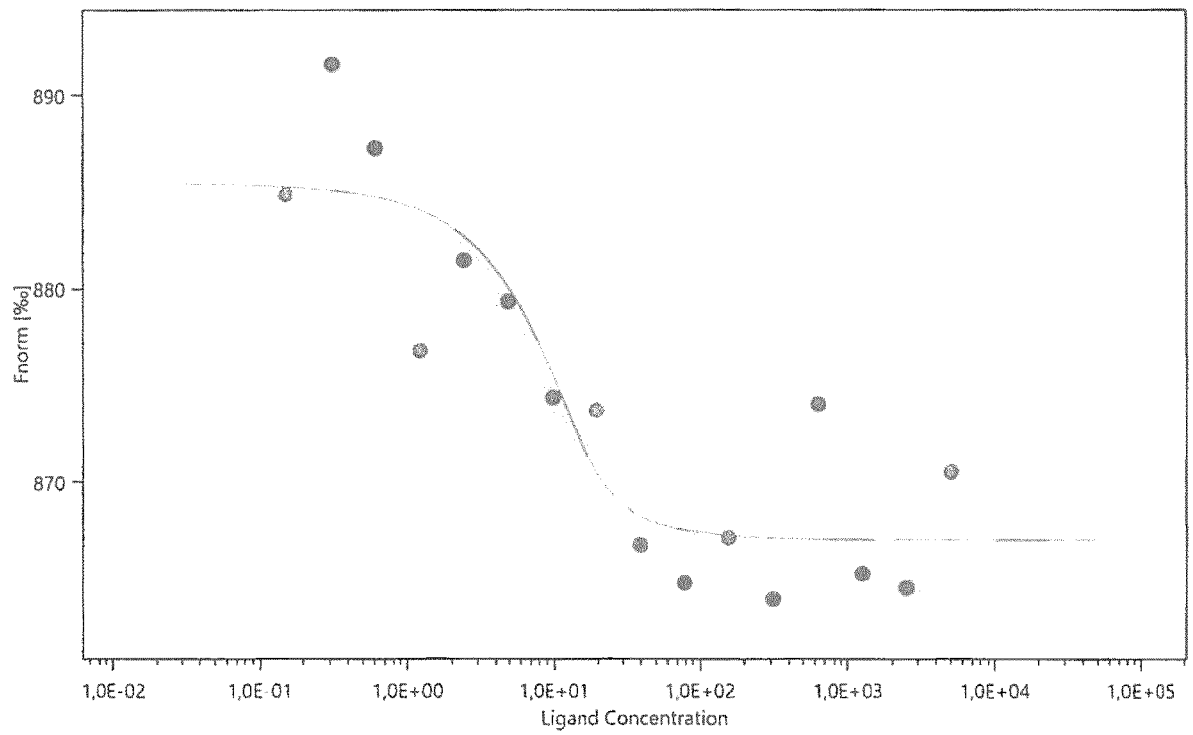

Binding curve measured by MST. The measurement method is based on the directed movement of molecules along a temperature gradient, an effect termed "thermophoresis". A local temperature difference $\Delta T$ leads to a local change in molecule concentration (depletion or enrichment), quantified by the Soret coefficient $S_T$: $c_{hot}/c_{cold}=\exp(-S_T\Delta T)$. MEC-1 or Jurkat membrane preparation is labeled using the Nanotemper NT-647 labeling kit as described elsewhere.[xlvi] The labeled preparation is eluted with PBS and stored at 4° C. A stock solution of each peptide is prepared in DMSO (5 mM) and then diluted with PBS. For the peptides evaluated by MST, we have kept the concentration of the NT.115-labeled membrane constant, while the concentration of the ligand (peptide) was varied. After a short incubation the samples were loaded into MST premium glass capillaries and the MST analysis was performed using the Monolith NT.115-pico. FIG. 5: MST curve observed for PKT16 [(D)Lys-(N-Me)Arg-PheTyr-Val-Val-Nle-Trp-Lys-(D)Lys] (SEQ ID NO:66) a linear peptide derived from the C-terminal binding domain of TSP-1. The Kd=1600 nM. FIG. 6A to 6H: MST curve observed for PKTD1, PKTD10, PKTD10-1, PKTD10-3, PKTD10-4, PKTD10-5, PKTD10-7, PKTD10-8 [see table II] all cyclic peptide analogues of the C-terminal binding domain of TSP-1. The Kd (from 0.1 to 505 nM). The Kd ratio highlights the fact that these cyclic analogues are all much more efficient in CD47 ligation than the linear analogues designed from the beta-strand 7. Kd of these cyclic peptides is comprised between 2.8 and 50 nM; this value is highly variable depending the tumor cells and their preparation.

4. Stability Assays

Proteolytic stability studies were performed by peptides incubation with proteases (such as Trypsin, Chymotrypsin and Proteinase K) or in Human Serum as described earlier (See Karoyan et al. J. Med. Chem. 2016). In these conditions, peptides such as PKD8, PKD9 or PKD10 appeared to be fully stable toward proteases whereas PKC1 is degraded by Trypsin in less than 2 hours like the linear analogue of PKD10, i.e L-PKD10: cyclisation is not sufficient to improve the metabolic stability (PKC1) neither to improve the pharmacological profil (PKC1) but the development of a stable harpin mimetic of the C-terminal binding domain of TSP-1 led to stable analogues (at least PKD8, PKD9 and PKD10) with improved pharmacological properties and ability to induce programmed Cell death (PKD8, PKD10, PKD10-FF at least).

REFERENCES

[i] Fuchs, Y.; Steller, H. Programmed Cell Death in Animal Development and Disease. Cell, 2011, 147 (4), 742-748.

[ii] Favaloro, B.; Allocati, N.; Graziano, V.; Di Ilio, C.; De Laurenzi, V. Role of Apoptosis in disease. AGING, 2012, 4, 5, 330-349.

[iii] Hanahan D and Weinberg R A. Cell, 2000, 100, 57-70.

[iv] a) Lobo, I. Chromosome abnormalities and cancer cytogenetics. *Nature Education* 2008, 1(1):68. b) Calin, G. A.; Croce, C. M. MicroRNAs and chromosomal abnormalities in cancer cells, *Oncogene* 2006, 25, 6202-6210. For more information, see http://cgap.nci.nih.gov/Chromosomes/Mitelman

[v] Delavallée, L.; Cabon, L.; Galàn-Malo, P.; Lorenzo, H. K.; Susin, S-A. AIF-mediated Caspase-independent Necroptosis: A New Chance for Targeted Therapeutics. *Life,* 2011, 63(4): 221-232.

[vi] Susin, S-A, Merle-Beral, H., Launay, P., Karoyan, P. Method and pharmaceutical composition for use in treatment of cancer. PCT Int. Appl. (2013), WO 2013182650 A1 20131212.

[vii] Lopez-Dee Z, Pidcock K, Gutierrez L-S. "Thrombospondin-1: Multiple Path to inflammation, Mediators of Inflammation, Volume 2011, doi:10.1155/2011/296069

[viii] a) Nagata S. Apoptosis and autoimmune diseases. *IUBMB Life.* 2006; 58:358-362. b) Nagata S. Autoimmune diseases caused by defects in clearing dead cells and nuclei expelled from erythroid precursors. *Immunological reviews.* 2007; 220:237-250.

[ix] Madkaikar M, Mhatre S, Gupta M and Ghosh K. Advances in autoimmune lymphoproliferative syndromes. *Eur J Haematol.* 2011; 87:1-9.

[x] Tischner D, Woess C, Ottina E and Villunger A. Bcl-2-regulated cell death signalling in the prevention of autoimmunity. *Cell Death Dis.* 2010; 1:e48.

[xi] a) Fadeel B and Orrenius S. Apoptosis: a basic biological phenomenon with wide-ranging implications in human disease. *J Intern Med.* 2005; 258:479-517. b) Bouillet P, Metcalf D, Huang D C, Tarlinton D M, Kay T W, Kontgen F, Adams J M and Strasser A. Proapoptotic Bcl-2 relative Bim required for certain apoptotic responses, leukocyte homeostasis, and to preclude autoimmunity. *Science.* 1999; 286:1735-1738.

[xii] See ref. 6. Tischner D, 2010.

[xiii] Secchiero, P.; di Lasio, M. G.; Gonelli, A.; Zauli, G. The MDM2 inhibitor Nutlins as an innovative therapeutic tool for the treatment of haematological malignancies. *Curr. Pharm. Des.* 2008, 14 (21), 2100-2110.

[xiv] Gandhi, L.; Camidge, D. R.; de Oliveira, M. R.; Bonomi, P.; Gandara, D.; Khaira, D., Hann, C. L.; McKeegan, E. M.; Litvinovich, E.; Hemken, P. M.; Dive, C.; Enschede, S. H.; Nolan, C.; Chiu, Y-L.; Busman, T.; Xiong, H.; Krivoshik, A. P.; Humerickhouse, R. H.; Shapiro, G. I.; Rudin, C. M. Phase I study of Navitoclax (ABT-263), a novel Bcl-2 family inhibitor, in patients with small-cell lung cancer and other solid tumors. *Journal of clinical oncology,* 2011, 29(7), 909-916.

[xv] Sun, H.; Nikolovska-Coleska, Z.; Yang, C-H.; Qian, D.; Lu, J.; Qiu, S.; Bai, L.; Peng, Y.; Cai, Q.; Wang, S. Design of Small-Molecule Peptidic and Non-Peptidic Smac Mimetics. *Acc. Chem. Res.* 2008, 41(10), 1264-1277.

[xvi] Murray, J. K.; Gellman, S. H. Targeting Protein-Protein Interactions: Lessons from p53/MDM2. *PeptideScience* 2008, 657-684.

[xvii] Stilgenbauer, S.; Benner, A.; Leupolt, E.; Kröber, A.; Bullinger, L.; Döhner, K.; Bentz, M.; Lichter, P. *Genomic aberrations and survival in chronic lymphocytic leukemia.* N. Engl. J. Med. 2000, 343, 1910-1916.

[xviii] Wilson, F. H.; Johannessen, C. M.; Piccioni, F.; Tamayo, P.; Kim, J. W.; Van Allen, E. M.; Corsello, S. M.; Capelletti, M.; Calles, A.; Butaney, M.; Sharifnia, T.; Gabriel, S. B.; Mesirov, J. P.; Hahn, W. C.; Engelman, J. A.; Meyerson, M.; Root D. E.; Jänne, P. A.; Garraway L A. A functional landscape of resistance to ALK inhibition in lung cancer. *Cancer Cell,* 2015 27, 397-408. doi: 10.1016/j.ccell.2015.02.005

[xix] Lawler, J. W., Slayter, H. S. & Coligan, J. E. Isolation and characterization of a high molecular weight glycoprotein from human blood platelets. *J Biol Chem* 253, 8609-16 (1978).

[xx] Gao, A. G. & Frazier, W. A. Identification of a receptor candidate for the carboxyl-terminal cell binding domain of thrombospondins. *J Biol Chem* 269, 29650-7 (1994).

[xxi] Gao, A. G. et al. Integrin-associated protein is a receptor for the C-terminal domain of thrombospondin. *J Biol Chem* 271, 21-4 (1996).

[xxii] Kosfeld, M. D. & Frazier, W. A. Identification of a new cell adhesion motif in two homologous peptides from the COOH-terminal cell binding domain of human thrombospondin. *J Biol Chem* 268, 8808-14 (1993).

[xxiii] Chao M. P.; Weissman, I. L.; Majeti R. Curr. Opin. Immunol. 2012, 24 (2): 225-32

[xxiv] Floquet, N., Dedieu, S., Martiny, L., Dauchez, M. & Perahia, D. Human thrombospondin's (TSP-1) C-terminal domain opens to interact with the CD-47 receptor: a molecular modeling study. *Arch Biochem Biophys* 478, 103-9 (2008).

[xxv] Lamy, L. et al. CD47 and the 19 kDa interacting protein-3 (BNIP3) in T cell apoptosis. *J Biol Chem* 278, 23915-21 (2003).

[xxvi] Brooke, G., Holbrook, J. D., Brown, M. H. & Barclay, A. N. Human lymphocytes interact directly with CD47 through a novel member of the signal regulatory protein (SIRP) family. *J Immunol* 173, 2562-70 (2004).

[xxvii] Manna, P. P., Dimitry, J., Oldenborg, P. A. & Frazier, W. A. CD47 augments Fas/CD95-mediated apoptosis. *J Biol Chem* 280, 29637-44 (2005).

[xxviii] Mateo, V. et al. CD47 ligation induces caspase-independent cell death in chronic lymphocytic leukemia. *Nat Med* 5, 1277-84 (1999).

[xxix] Pettersen, R. D., Hestdal, K., Olafsen, M. K., Lie, S. O. & Lindberg, F. P. CD47 signals T cell death. *J Immunol* 162, 7031-40 (1999).

[xxx] Uno, S. et al. Antitumor activity of a monoclonal antibody against CD47 in xenograft models of human leukemia. *Oncol Rep* 17, 1189-94 (2007).

[xxxi] Manna, P. P. & Frazier, W. A. CD47 mediates killing of breast tumor cells via Gi-dependent inhibition of protein kinase A. *Cancer Res* 64, 1026-36 (2004).

[xxxii] Kikuchi, Y. et al. Apoptosis inducing bivalent single-chain antibody fragments against CD47 showed antitumor potency for multiple myeloma. *Leuk Res* 29, 445-50 (2005).

[xxxiii] Saumet, A., Slimane, M. B., Lanotte, M., Lawler, J. & Dubernard, V. Type 3 repeat/Cterminal domain of thrombospondin-1 triggers caspase-independent cell death through CD47/alphavbeta3 in promyelocytic leukemia NB4 cells. *Blood* 106, 658-67 (2005).

[xxxiv] Mateo, V. et al. Mechanisms of CD47-induced caspase-independent cell death in normal and leukemic cells: link between phosphatidylserine exposure and cytoskeleton organization. *Blood* 100, 2882-90 (2002).

[xxxv] Roue, G. et al. Mitochondrial dysfunction in CD47-mediated caspase-independent cell death: ROS production in the absence of cytochrome c and AIF release. *Biochimie* 85, 741-6 (2003).

[xxxvi] Bras, M. et al. Drp1 mediates caspase-independent type III cell death in normal and leukemic cells. *Mol Cell Biol* 27, 7073-88 (2007).

[xxxvii] Manna, P. P. & Frazier, W. A. The mechanism of CD47-dependent killing of T cells: heterotrimeric Gi-dependent inhibition of protein kinase A. *J Immunol* 170, 3544-53 (2003).

[xxxviii] Barbier, S. et al. Caspase-independent type III programmed cell death in chronic lymphocytic leukemia: the key role of the F-actin cytoskeleton. *Haematologica* 94, 507-17 (2009).

[xxxix] Merle-Beral, H. et al. Caspase-independent type III PCD: a new means to modulate cell death in chronic lymphocytic leukemia. *Leukemia* 23, 974-7 (2009).

[xl] Bras, M. et al. Drp1 mediates caspase-independent type III cell death in normal and leukemic cells. *Mol Cell Biol* 27, 7073-88 (2007).

[xli] Mateo, V. et al. Mechanisms of CD47-induced caspase-independent cell death in normal and leukemic cells: link between phosphatidylserine exposure and cytoskeleton organization. *Blood* 100, 2882-90 (2002).

[xlii] Floquet & al. Human thrombospondin's (TSP-1) C-terminal domain opens to interact with the CD-47 receptor: A molecular modeling study (2008). Archives of Biochemistry and Biophysics 478 (2008) 103-109

[xliii] Chao, M. P., Weissman, I. L. & Majeti, R. The CD47-SIRPalpha pathway in cancer immune evasion and potential therapeutic implications. *Curr Opin Immunol* 24, 225-32.

[xliv] helsinkifi/biosciences/corefacilities/microscalethermophoresis/Protein_Labeling_Manual_V012-RED-NHS.pdf

[xlv] Jerabek-Willemsen, M.; Wienken, C. J.; Braun, D.; Baaske, P.; Duhr, S. Molecular Interaction Studies Using Microscale Thermophoresis. *ASSAY and Drug Development Technologies*, 2011, 9, 342-353.

[xlvi] helsinki.fi/biosciences/corefacilities/microscalethermophoresis/Protein_Labeling_Manual_V012-RED-NHS.pdf

The invention claimed is:

1. An isolated cyclic peptide of general formula (Ia):

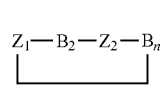

(Ia)

or a pharmacologically acceptable salt thereof, wherein:

$Z_1$ is nothing or an heterochiral sequence D-Pro-L-Pro or any sequence of two amino acids or analogs of amino acid able to mimic said heterochiral sequence or mimic a beta turn;

$B_2$ represents the peptidic sequence $X_1$-$X_2$-$X_3$-$X_4$-$X_5$-$X_6$-$X_7$-$X_8$-$X_9$-$X_{10}$ (SEQ ID NO: 2) and comprises between 6 and 10 amino acids, wherein:

$X_1$ refers to nothing or serine;
$X_2$ refers to nothing, arginine, or N-methyl arginine;
$X_3$ refers to phenylalanine;
$X_4$ refers to tyrosine;
$X_5$ refers to valine;
$X_6$ refers to valine;
$X_7$ refers to methionine, lysine, or norleucine;
$X_8$ refers to tryptophan;
$X_9$ refers to nothing or lysine;
$X_{10}$ refers to nothing or glutamine;

$Z_2$ is nothing or an heterochiral sequence D-Pro-L-Pro or any sequence of two amino acids or analogs of amino acid able to mimic said heterochiral sequence or mimic a beta turn;

$B_3$ is a peptidic sequence of between 6 and 10 amino acids comprising the following sequence: -$X_{19}$-$X_{14}$-$X_{15}$-$X_{20}$-$X_{21}$-$X_{16}$-$X_{22}$-$X_{23}$-$X_{17}$-$X_{18}$- (SEQ ID NO: 36) wherein:

$X_{14}$ is nothing, glycine, alanine, or serine;
$X_{15}$ is isoleucine or leucine;
$X_{16}$ is lysine or alanine;
$X_{17}$ is nothing, asparagine, alanine, glutamine or lysine;
$X_{18}$ is nothing, serine, or glycine;
$X_{19}$ is nothing or serine;
$X_{20}$ is serine, alanine or leucine;
$X_{21}$ is valine or alanine;
$X_{22}$ is valine; and
$X_{23}$ is valine or alanine;

wherein said isolated cyclic peptide comprises an even number of amino acids and wherein said isolated cyclic peptide comprises between 8 and 26 amino acids.

2. A pharmaceutical composition comprising the isolated cyclic peptide of claim 1 and a pharmaceutically acceptable carrier.

3. The isolated cyclic peptide according to claim 1, wherein both $Z_1$ and $Z_2$ are nothing.

4. The isolated cyclic peptide according to claim 1, wherein $Z_1$ or $Z_2$ is D-Pro-L-Pro.

5. A method of treating a disease associated with defects in PCD in a subject in need thereof comprising administering a therapeutically effective amount of the isolated cyclic peptide of claim 1 to the subject.

6. The method of claim 5, wherein the disease is cancer selected from the group consisting of adrenal cortical cancer, anal cancer, bile duct cancer, multiple myeloma, bladder cancer, bone cancer, brain and central nervous system cancer, breast cancer, Castleman disease, cervical cancer, colorectal cancer, endometrial cancer, esophagus cancer, gallbladder cancer, gastrointestinal carcinoid tumors, Hodgkin's disease, non-Hodgkin's lymphoma, Kaposi's sarcoma, kidney cancer, laryngeal and hypopharyngeal cancer, leukemia, liver cancer, lung cancer, mesothelioma, plasmacytoma, nasal cavity and paranasal sinus cancer, nasopharyngeal cancer, neuroblastoma, oral cavity and oropharyngeal cancer, ovarian cancer, pancreatic cancer, penile cancer, pituitary cancer, prostate cancer, retinoblastoma, rhabdomyosarcoma, salivary gland cancer, skin cancer, melanoma, stomach cancer, testicular cancer, thymus cancer, thyroid cancer, vaginal cancer, vulvar cancer, and uterine cancer.

7. The method of claim 5, wherein the disease is an immunological disorder.

8. The method of claim 5, wherein the disease is chronic inflammation.

9. The isolated cyclic peptide according to the claim 1 wherein said peptide is selected from a group consisting of PKTD1 (SEQ ID NO: 9), PKTD10 (SEQ ID NO: 17), PKTD10-1 (SEQ ID NO: 18), PKTD10-3 (SEQ ID NO: 20), PKTD10-4 (SEQ ID NO: 21), PKTD10-5 (SEQ ID NO: 22), PKTD10-7 (SEQ ID NO: 24), PKTD10-8 (SEQ ID NO: 25), PKTD12 (SEQ ID NO: 29), PKTD18 (SEQ ID NO: 35), PKD8 (SEQ ID NO: 41), PKD9 (SEQ ID NO: 43), PKD10 (SEQ ID NO: 44), PKTD10-RNMe (SEQ ID NO: 54), PKTD10-X-RNMe (SEQ ID NO: 55), PKTD11-RNMe (SEQ ID NO: 60).

* * * * *

UNITED STATES PATENT AND TRADEMARK OFFICE
CERTIFICATE OF CORRECTION

PATENT NO. : 11,306,124 B2
APPLICATION NO. : 16/099997
DATED : April 19, 2022
INVENTOR(S) : P. Karoyan Page 1 of 1

It is certified that error appears in the above-identified patent and that said Letters Patent is hereby corrected as shown below:

On the Title Page

| Column | Line | |
|---|---|---|
| Abstract | 5 | change "relate" to -- relates --. |

Signed and Sealed this
Twenty-first Day of March, 2023

*Katherine Kelly Vidal*
Katherine Kelly Vidal
*Director of the United States Patent and Trademark Office*